United States Patent [19]
Wang et al.

[11] Patent Number: 5,796,476
[45] Date of Patent: Aug. 18, 1998

[54] METHOD OF OPTICALLY MEASURING COMPONENT IN SOLUTION

[75] Inventors: Yung Xiang Wang; Xiaoming Dou, both of Kyoto, Japan

[73] Assignee: Kyoto Dai-Ichi Kagaku Co., Ltd., Kyoto, Japan

[21] Appl. No.: 672,026

[22] Filed: Jun. 26, 1996

[30] Foreign Application Priority Data

Jun. 28, 1995 [JP] Japan .................................. 7-186341
Sep. 13, 1995 [JP] Japan .................................. 7-262338

[51] Int. Cl.$^6$ ...................................................... G01J 3/44
[52] U.S. Cl. ............... 356/301; 250/339.01; 250/339.07
[58] Field of Search ........................... 356/317, 318, 356/301; 250/461.2, 339.01–339.15

[56] References Cited

U.S. PATENT DOCUMENTS

| | | | |
|---|---|---|---|
| 4,427,889 | 1/1984 | Muller .................. | 250/339.12 |
| 4,832,483 | 5/1989 | Verma ...................... | 356/39 |
| 4,847,198 | 7/1989 | Nelson et al. .............. | 356/301 |
| 4,855,243 | 8/1989 | Simic-Glavaski ......... | 356/301 |
| 4,957,366 | 9/1990 | Koshi et al. ............... | 356/318 |
| 5,047,639 | 9/1991 | Wong ......................... | 356/318 |
| 5,115,137 | 5/1992 | Andersson-Engles et al. | |
| 5,459,317 | 10/1995 | Small ........................ | 250/341.1 |
| 5,481,113 | 1/1996 | Dou et al. .................. | 356/301 |
| 5,553,616 | 9/1996 | Ham et al. ................. | 140/339.07 |
| 5,596,196 | 1/1997 | Cooper et al. ............. | 250/339.12 |

OTHER PUBLICATIONS

Tuma et al.,Cysteine Conformation and Sulfhydryl Interactions in Proteins and Viruses. 3. Quantitative Measurement of the Raman S–H Band Intensity and Frequency. Biophysical Journal, vol. 65, Sep. 1993, pp. 1066–1072.

Goetz, Jr. et al. IEEE Transactions on Biomedical Engineering. Jul. 1995, pp. 728–731.

Goetz Jr., et al., Detection of Glucose Using Raman Spectroscopy, IEEE, USA, Mar. 11, 1994, pp. 816–817.

Berjot et al., Determination of the Secondary Structure of Proteins from the Raman Amide I Band: The Reference Intensity Profiles Method. Journal of Raman Spectroscopy. vol. 18, 1987, pp. 289–300.

*Primary Examiner*—F. L. Evans
*Assistant Examiner*—Zandra V. Smith
*Attorney, Agent, or Firm*—Nikaido Marmelstein Murray & Oram LLP

[57] ABSTRACT

A sample solution containing protein is irradiated with excitation light of a single wavelength which is emitted from a light source, so that light scattered from the sample solution is received and separated into its spectral components in a spectroscope, thereby obtaining light scattering spectra. Protein is quantitatively measured through intensity of a light scattering spectrum in a shift wavenumber of 100 to 3100 cm$^{-1}$ with respect to the excitation wavelength among the light scattering spectra or an integral value in a proper range therein. As to a body fluid sample, the sample is irradiated with excitation light and Raman scattering spectral intensity values are measured at a plurality of wavenumbers in an arbitrary wavenumber range, and a plurality of components in the sample are analyzed simultaneously by multivariate regression analysis.

8 Claims, 41 Drawing Sheets

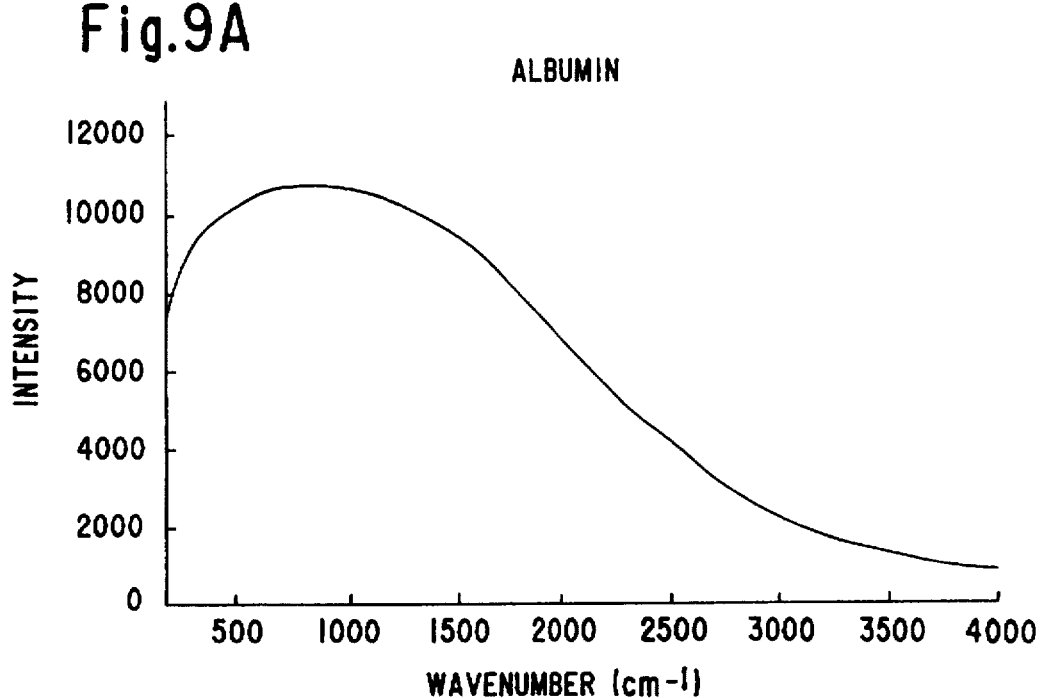
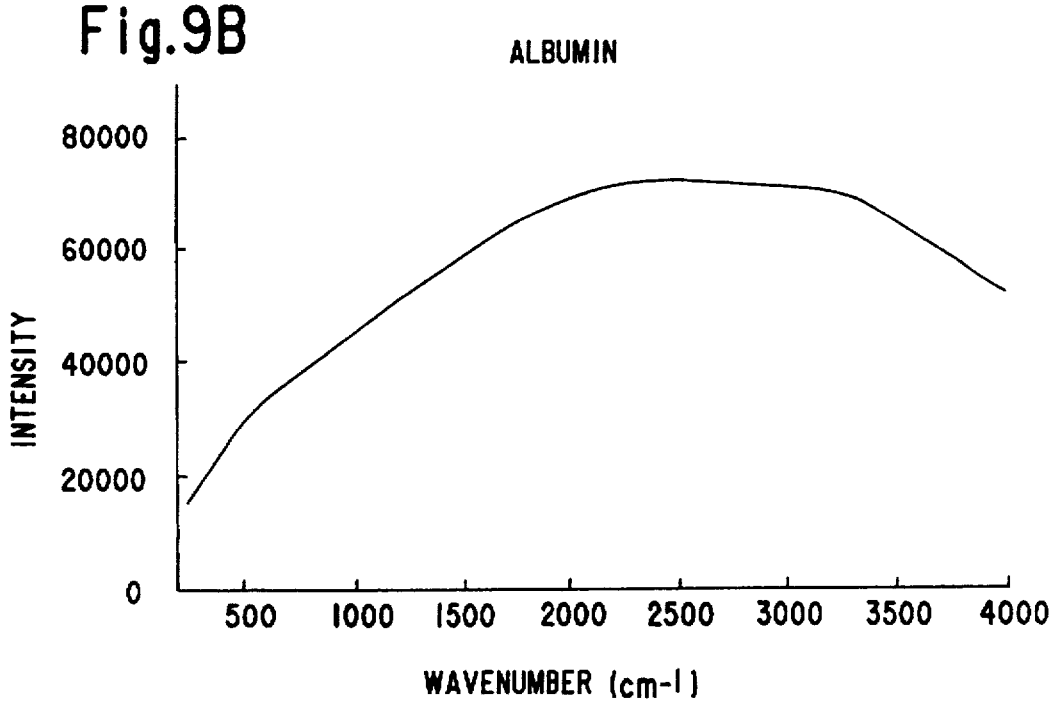

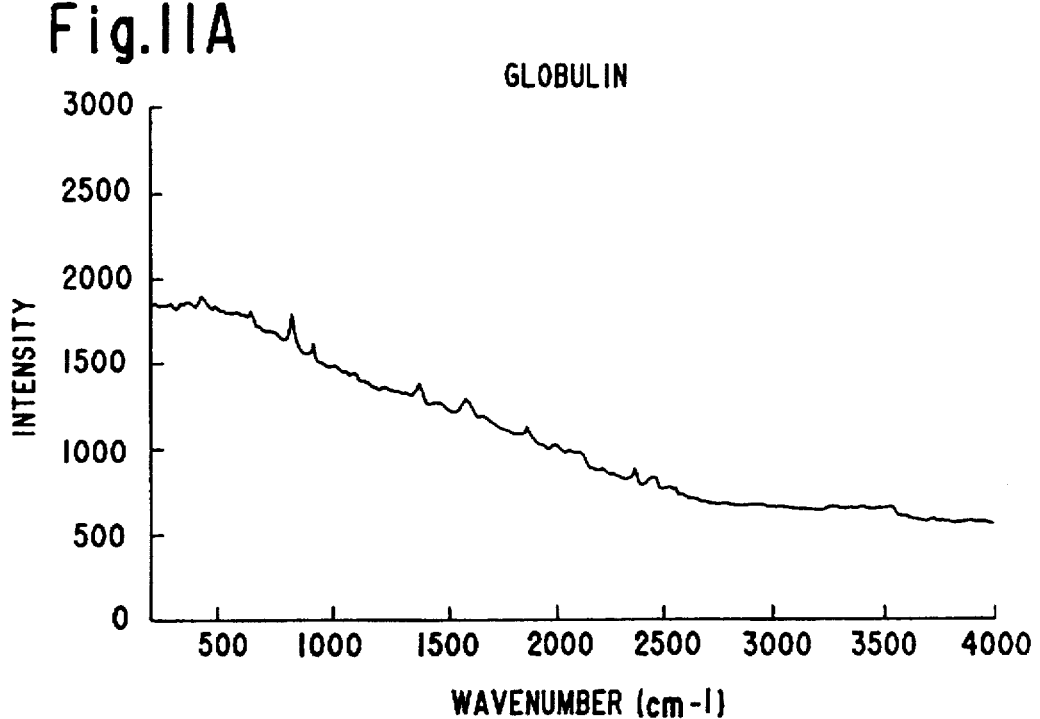
Fig.11A GLOBULIN
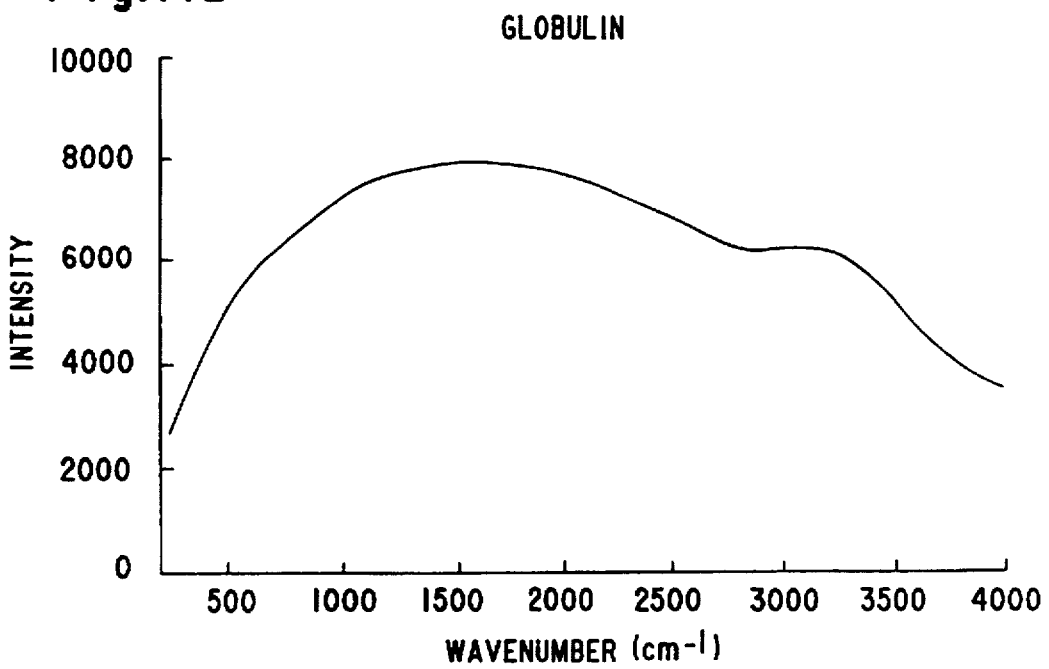
Fig.11B GLOBULIN

ACETONE (17%(V/V))
NORMAL URINE + UREA (50mg/ml)
GLUCOSE (1.17mg/ml)

RAMAN URINE TEST (INTRA-URINARY COMPONENT DETECTION WAVENUMBERS)

| COMPONENT \ cm⁻¹ | 0~1000 | 1000~1500 | 1500~2000 | 2000~2500 | 2500~ |
|---|---|---|---|---|---|
| ALBUMIN | 188, 620;830 | | | | |
| GLOBULIN | 432,653;837;852 | 1383 | 1592, 1877 | 2370 | |
| HEMOGLOBIN | 837;923 | 1383;1592 | 1870 | 2125;2370;2433 | 2900;2924 |
| GLUCOSE | 405,524,648,779,840,914 | 1054,1076,1276,1346,1426 | 1640 | 2125;2370;2433 | 2937 |
| LITHIUM ACETOACETATE | 829 | 1383 | 1870 | 2377 | 2900;2941 |
| β-HYDROXYBUTYRIC ACID | | 1450 | | | 2941 |
| ACETONE | 805 | 1237, 1429 | 1587;1630 | | |
| DITAUROBILIRUBIN | 957 | 1263 | 1710 | | |
| UROBILIN | 813 | 1008;1063,1168 | 1616 | 2370 | |
| SODIUM NITRITE | | 1348 | 1613 | | |
| UREA | 531,597 | | | | |
| URIC ACID | 570 | | | | |
| FOLIC ACID | 661 | | 1592, 1877 | 2123,2369,2430 | |
| ASCORBIC ACID | 846,931 | 1385 | 1703 | | |
| VITAMIN B2 | 830 | 1347 | 1576, 1864 | 2136,2390,2449 | |
| CREATINE MONOHYDRATE | 434, 656,825;890 | | 1593 | | |
| CREATININE | 830 | | 1576,1593 | | 2898;2932,2966 |
| α-AMYLASE | 423;661,822,895 | 1363 | 1576, 1864 | 2364 | 2949 |
| β-AMYLASE | 406,652,813,898 | 1364 | 1576, 1864 | | 2595 |
| AMMONIA | 568,610,695,847,898 | | | | 3220,3322,3407 |

Fig.63
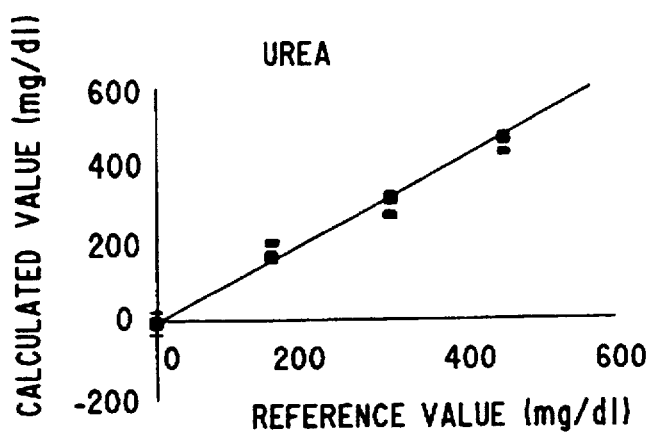
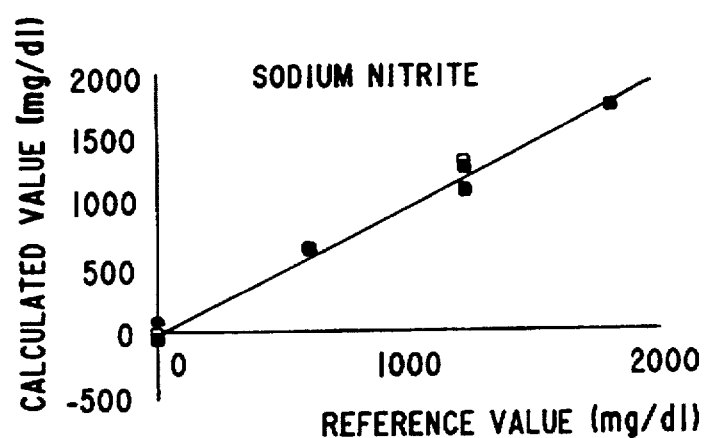
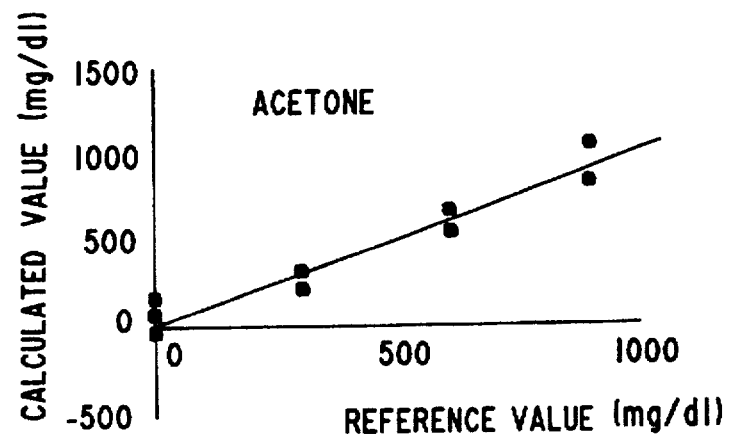

METHOD OF OPTICALLY MEASURING COMPONENT IN SOLUTION

BACKGROUND OF THE INVENTION

1. Field of the Invention

The present invention relates to a method of optically measuring protein in a sample solution and various components in body fluids such as urine, blood, blood serum, blood plasma, saliva and sweat.

2. Description of the Background Art

While urine protein is discharged by 20 to 80 mg a day in a normal state, the amounts of protein discharged in urine fluctuate in various pathosises. Namely, the amount of intra-urinary protein serves as an index of pathologic diagnosis, and hence measurement accuracy and likelihood thereof must be at high levels. Further, it is necessary to recognize various protein components discharged in urine, which serve as indices of different diseases, independently of each other by an examination having specificity.

While Esbach method employing picric acid and Sueyoshi test employing mercuric chloride which are adapted to add protein precipitation reagents to urine for estimating protein concentrations from the thicknesses of resulting precipitation layers have been employed as old methods of measuring urine protein amounts, these methods have been problematic in specificity and accuracy. At present, nephelometry of nephelometrically analyzing turbidity by salicylsulfonic acid or trichloroacetic acid and colorimetry utilizing bonding between protein and a pigment are employed.

In the nephelometry, turbidity varies with the type of protein. It is insufficient in specificity. A strong alkaline target substance completely neutralizes an acidic precipitation reagent, to cause false negativeness. Further, observation of turbidity is not standardized, disadvantageously leading to personal equation.

In the colorimetry, on the other hand, hemoglobin and globulin do not so sharply react as albumin, while a highly buffered alkaline target substance causes false positiveness. Further, it is difficult to discriminate color tones.

Properties of active principles forming urine are changed with time and hence urine analysis must be quickly carried out. However, urine is made to react with a pH indicator for determination through its changed color tone in the colorimetry, while protein is precipitated by heating or addition of acid for determination of its turbidity in the nephelometry. Namely, the colorimetry and nephelometry are complicated and insufficient in quickness since these reactions are necessary.

There are a reagent method, a test paper method, a chemiluminescence method, an immunoassay method, an enzyme method and a chromatography method as methods of measuring components in body fluids.

A test paper employed in the test paper method is generally prepared by fixing a reacting part consisting of cellulose containing a reaction reagent to a plastic holder by an adhesive or the like and drying the same. When the reacting part contains moisture, reaction is caused between reagents, and the same is also denatured by a high temperature or light to be reduced in sensitivity, and hence a container for storing the test paper must be sealed, preserved to avoid a high temperature, and used within the period of validity. While the test paper method of urine analysis is capable of simultaneously measuring a number of items such as pH, protein, glucose, a ketone body, bilirubin, occult blood, urobilinogen, microbism and specific gravity within one minute, reaction of a reagent part is influenced by reaction temperature, moisture and the like in addition to an intrinsic accelerator or inhibitor, and only semiquantitative analysis can be performed. A determination method in the test paper method is mainly the colorimetry, and chemical reaction such as enzyme reaction or oxidation-reduction reaction is principal in its reaction mechanism. In the reagent method, on the other hand, the colorimetry through an indicator or enzyme/chemical reaction or the nephelometry employed for protein measurement is principal.

While an enzyme method is simple with a target substance having high specificity, there is such an apprehension that positive reaction is concealed by the color tone of a body fluid itself, and reaction may be suppressed by various intrinsic and extrinsic oxidation and reduction reaction substances when the method is through oxidation-reduction reaction, leading to such an apprehension that false negativeness or positiveness is recognized.

Every method is an indirect measuring method for making measurement through mediational reaction, and hence there are potential errors. In case of making determination by the colorimetry, errors are readily caused in determination of the results, while that through chemical reaction has low specificity. Further, a number of substances interfering with the test are present in the body fluid, and hence reaction is inhibited, false positive reaction is caused, or a color tone different from that of positive reaction is presented to conceal the positive reaction. A system employing an enzyme is essentially instable, while a system through chemical reaction is readily influenced by a coexistent substance. While it is useful to simultaneously test a number of items for making total determination when clinical meanings of test items are in mutual relation to each other (bilirubin and urobilinogen, protein and occult blood, and glucose and a ketone body), it is troublesome to test the respective items independently of each other, and influences are readily exerted by interfering substances. A multi-item test paper tends to be kept away at a distance since the same is high-priced and hard to determine.

The reagent method, the test paper method and the enzyme method require reagents, test paper pieces and enzymes which are expendable items, and there are also problems of preservation stability of the reagents etc. before employment and disposal thereof after employment. Further, errors may be caused in the amounts of the reagents and samples by mistakes in operation, the operations are troublesome, and interfering actions are disadvantageously applied by other components such as ascorbic acid. While the reagent method and the enzyme method are capable of quantitative measurement of single components, it is impossible to simultaneously measure a number of components. On the other hand, the test paper method can merely make semiquantitative analysis, although the same can simultaneously measure a number of components.

The chemiluminescence method requires a light emitting substance, while the immunoassay method through antigen-antibody reaction generally requires washing, comprises a large number of steps, and has apprehensions for influences by interfering substances and non-specific absorption.

The chromatography method requires pretreatments such as separation, and it is imposible to directly determine target substances in a sample of mixture.

SUMMARY OF THE INVENTION

A first object of the present invention is to provide a method of determining protein in a solution which can simply and quickly make the measurement without through the aforementioned mediational reaction.

A second object of the present invention is to provide a method of simultaneously quantitatively measuring a number of components in a body fluid by making reagents, test paper pieces or enzymes which are expendable items unnecessary and eliminating problems such as preservation stability of these expendable items before employment and disposal after employment, troublesome operations causing errors and interfering actions by other components.

The inventors have discovered that protein and other components in a target substance have specific light scattering spectra. The present invention is adapted to quantitatively measure respective main component concentrations from the peak intensity values of the light scattering spectra or cumulative intensity values over a proper wavenumber range.

According to a first aspect of the present invention, a method of measuring a protein concentration in a solution is adapted to irradiate a sample solution containing protein with excitation light, receive light scattered from the sample solution, and separate the same into its spectral components for obtaining light scattering spectra, thereby quantitatively measuring protein through the peak intensity of a spectrum in a shift wavenumber of 100 to 3100 $cm^{-1}$ with respect to the excitation wavelength among the light scattering spectra or an integral value in a proper range within the same.

While a principal one of light scattering spectra from an aqueous protein sample is a broad fluorescence spectrum, a sharp Raman scattering spectrum appears in superposition with the fluorescence spectrum depending on the type of the protein and an excitation wavelength. Accordingly, light scattering spectra to which the first aspect of the present invention is applied include both of fluorescence and Raman scattering spectra.

When the protein is albumin, it is preferable to employ the peak intensity of a spectrum shifted from the excitation wavelength to 810 to 840 $cm^{-1}$, or an integral value of a proper range of a spectrum shifted from an excitation wavelength of 632.8 nm to 256 to 1620 $cm^{-1}$ or from an excitation wavelength of 514.5 nm to 837 to 3060 $cm^{-1}$.

When the protein is γ-globulin, it is preferable to employ the peak intensity of a spectrum shifted from the excitation wavelength to 175 to 195 $cm^{-1}$, 425 to 450 $cm^{-1}$, 640 to 670 $cm^{-1}$, 820 to 845 $cm^{-1}$, 845 to 870 $cm^{-1}$, 1370 to 1400 $cm^{-1}$, 1575 to 1620 $cm^{-1}$, 1850 to 1900 $cm^{-1}$, 2000 to 2200 $cm^{-1}$, 2350 to 2400 $cm^{-1}$, or 2400 to 2460 $cm^{-1}$.

When the protein is hemoglobin, it is preferable to employ the peak intensity of a spectrum shifted from the excitation wavelength to 640 to 670 $cm^{-1}$, 820 to 845 $cm^{-1}$, 1370 to 1400 $cm^{-1}$, 1575 to 1620 $cm^{-1}$, 1850 to 1900 $cm^{-1}$, 2000 to 2200 $cm^{-1}$, 2350 to 2400 $cm^{-1}$, or 2400 to 2460 $cm^{-1}$.

According to a second aspect of the present invention, a method of simultaneously quantitatively measuring a number of components in a body fluid is adapted to obtain a specific Raman scattering spectrum from each body fluid component in a target substance for qualitatively/quantitatively measuring each component from its spectral intensity or spectral cumulative intensity or Raman scattering spectral intensity values at a plurality of wavenumbers in an arbitrary wavenumber range.

According to a first mode of the second aspect, a wavenumber having an excellent correlation between the concentration of a component and the Raman scattering spectral intensity is previously selected as a measuring wavenumber which is specific to the component as to each component of a body fluid to be measured, a body fluid sample is irradiated with excitation light for measuring Raman scattering spectral intensity at each measuring wavenumber as to each component to be measured, and the respective components in the body fluid are simultaneously qualitatively/quantitatively analyzed through a calibration curve which is previously prepared as to the Raman scattering spectral intensity at each measuring wavenumber and the concentration of the component. The Raman scattering spectral intensity at the measuring wavenumber indicates the height of a peak of the Raman scattering spectrum. Alternatively, the area of a Raman scattering spectral peak in a measuring wavenumber range including the measuring wavenumber may be measured in place of the peak height, for making qualification/determination.

According to a second mode of the second aspect, on the other hand, a body fluid sample is irradiated with excitation light for measuring Raman scattering spectral intensity values at wavenumbers having excellent correlations between concentrations of a plurality of components in the body fluid to be measured and Raman scattering spectral intensity values as measuring wavenumbers as specific to the respective components or Raman scattering spectral intensity values at a plurality of wavenumbers in an arbitrary wavenumber range, thereby simultaneously qualitatively/quantitatively analyzing a plurality of components in the body fluid sample by multivariate regression analysis.

As to each body fluid component to be measured, a wavenumber having a correlation coefficient R of at least 0.8, preferably at least 0.9, between the concentration of a single component aqueous solution and this specific Raman scattering spectral intensity is selected as a measuring wavenumber which is specific to the component. The correlation coefficient R is expressed as follows:

$$R = \frac{\sum_{i=1}^{n} \{(xi - X)(yi - Y)\}}{\sqrt{\left[\sum_{i=1}^{n}(xi - X)^2\right]\left[\sum_{i=1}^{n}(yi - Y)^2\right]}}$$

where xi represents the concentration of each point of the body fluid component, yi represents the Raman scattering spectral intensity with respect to xi, X represents an average value of the concentration of each point of the body fluid component, and Y represents an average value of the Raman scattering spectral intensity.

Preferable measuring wavenumbers or measuring wavenumber ranges for the respective components are selected from around 590 to 650 $cm^{-1}$, around 800 to 860 $cm^{-1}$, and around 2342 to 2402 $cm^{-1}$, for albumin (see FIG. 17), selected from around 158 to 218 $cm^{-1}$, around 402 to 462 $cm^{-1}$, around 623 to 683 $cm^{-1}$, around 807 to 867 $cm^{-1}$, around 822 to 862 $cm^{-1}$, around 1353 to 1413 $cm^{-1}$, around 1562 to 1622 $cm^{-1}$, around 1847 to 1907 $cm^{-1}$, around 2095 to 2155 $cm^{-1}$, around 2340 to 2400 $cm^{-1}$ and around 2403 to 2463 $cm^{-1}$ for globulin (see FIG. 47), selected from around 807 to 867 $cm^{-1}$, around 893 to 953 $cm^{-1}$, around 1353 to 1413 $cm^{-1}$, around 1562 to 1622 $cm^{-1}$, around 1840 to 1900 $cm^{-1}$, around 2095 to 2155 $cm^{-1}$, around 2340 to 2400 $cm^{-1}$, and around 2403 to 2463 $cm^{-1}$ for hemoglobin (see FIG. 48), selected from around 200 to 554 $cm^{-1}$, around 810 to 944 $cm^{-1}$, and around 2590 to 2940 $cm^{-1}$ for glucose (see FIG. 19), selected from around 799 to 859 $cm^{-1}$, around 1353 to 1413 $cm^{-1}$, around 1840 to 1900 $cm^{-1}$, around 2347 to 2407 cm⁻¹, and around 2907 to 2967 cm⁻¹ for lithium acetoacetate (see FIG. 45), selected from around 1420 to 1480 cm⁻¹, around 1557 to 1617 cm⁻¹, around 1600 to 1660 cm⁻¹, and around 2870 to 2971 cm⁻¹ for β-hydroxybutyric acid (see FIG. 46), selected from around 775 to 845 cm⁻¹, around 1050 to 1110 cm⁻¹, around 1207 to 1267 cm⁻¹, around 1399 to 1459 cm⁻¹, 1680 to 1740 cm⁻¹, and around 2911 to 2971 cm⁻¹ for acetone (see FIG. 25), selected from around 927 to 987 cm⁻¹, around 1233 to 1293 cm⁻¹, and around 1586 to 1616 cm⁻¹ for ditaurobilirubin (see FIG. 49), selected as an arbitrary position from 332 to 2900 cm⁻¹ for urobilin, selected from around 783 to 843 cm⁻¹, and around 1318 to 1378 cm⁻¹ for sodium nitrite (see FIG. 50), selected from around 501 to 561 cm⁻¹, around 567 to 627 cm⁻¹, around 978 to 1048 cm⁻¹, around 1033 to 1093 cm⁻¹, around 1138 to 1198 cm⁻¹, and around 1583 to 1643 cm⁻¹ for urea (see FIG. 21), selected from around 640 to 700 cm⁻¹ for uric acid (see FIG. 51), selected from around 631 to 691 cm⁻¹, around 816 to 876 cm⁻¹, around 901 to 961 cm⁻¹, around 1355 to 1415 cm⁻¹, around 1562 to 1622 cm⁻¹, around 1847 to 1907 cm⁻¹, around 2093 to 2153 cm⁻¹, around 2339 to 2399 cm⁻¹, and around 2400 to 2460 cm⁻¹ for folic acid (see FIG. 52), selected from around 800 to 860 cm⁻¹, around 1673 to 1733 cm⁻¹, and around 2919 to 2979 cm⁻¹ for ascorbic acid (see FIG. 53), selected from around 404 to 464 cm⁻¹, around 626 to 686 cm⁻¹, around 798 to 858 cm⁻¹, around 860 to 920 cm⁻¹, around 1317 to 1377 cm⁻¹, around 1546 to 1606 cm⁻¹, around 1834 to 1894 cm⁻¹, around 2106 to 2166 cm⁻¹, around 2360 to 2420 cm⁻¹, and around 2419 to 2479 cm⁻¹ for vitamin $B_2$ (see FIG. 54), selected from around 800 to 860 cm⁻¹, and around 1563 to 1623 cm⁻¹ for creatine monohydrate (see FIG. 55), selected from around 538 to 598 cm⁻¹, 580 to 640 cm⁻¹, around 665 to 725 cm⁻¹, around 817 to 877 cm⁻¹, around 868 to 928 cm⁻¹, around 1021 to 1081 cm⁻¹, around 1550 to 1610 cm⁻¹, around 2868 to 2900 cm⁻¹, around 2900 to 2950 cm⁻¹, and around 2950 to 2996 cm⁻¹ for creatinine (see FIG. 56), selected from around 393 to 453 cm⁻¹, around 631 to 691 cm⁻¹, around 792 to 852 cm⁻¹, around 868 to 928 cm⁻¹, around 1333 to 1393 cm⁻¹, around 1546 to 1606 cm⁻¹, around 1834 to 1894 cm⁻¹, and around 2334 to 2394 cm⁻¹ for α-amylase (see FIG. 57), selected from around 376 to 436 cm⁻¹, around 622 to 682 cm⁻¹, around 783 to 843 cm⁻¹, around 868 to 928 cm⁻¹, around 1334 to 1394 cm⁻¹, around 1546 to 1606 cm⁻¹, around 1834 to 1894 cm⁻¹, and around 2665 to 2725 cm⁻¹ for β-amylase (see FIG. 58), selected from around 3190 to 3250 cm⁻¹, around 3292 to 3350 cm⁻¹, and 3377 to 3437 cm⁻¹ for ammonia (see FIG. 59), selected from around 404 to 464 cm⁻¹, around 805 to 865 cm⁻¹, around 1014 to 1074 cm⁻¹, around 1438 to 1498 cm⁻¹, and around 2966 to 3026 cm⁻¹ for inositol (see FIG. 60), selected from around 466 to 526 cm⁻¹, 835 to 895 cm⁻¹, around 1032 to 1092 cm⁻¹, 1237 to 1297 cm⁻¹, around 1332 to 1392 cm⁻¹, around 1438 to 1498 cm⁻¹, and around 2946 to 3006 cm⁻¹ for galactose (see FIG. 61), and selected from around 569 to 629 cm⁻¹, around 772 to 832 cm⁻¹, around 1044 to 1106 cm⁻¹, around 1237 to 1297 cm⁻¹, around 1438 to 1498 cm⁻¹, and around 2966 to 2996 cm⁻¹ for fructose (see FIG. 62).

When a body fluid specimen contains at least two of the aforementioned components, it is preferable to irradiate the body fluid specimen with excitation light of a single wavelength, receive light scattered from the body fluid specimen for obtaining Raman scattering spectra, and calculate the respective component concentrations on the basis of spectral intensity values in wavenumber regions which are set in the aforementioned manner for the respective components and not superposed with each other.

A multivariate regression analysis operation is adapted to make data analysis through a multivariate regression analysis method such as a principal component regression analysis method (PCR) or a partial least square method (PLS). In the multivariate regression analysis, regression analysis can be made while simultaneously employing a number of spectral intensity values, thereby enabling quantitative analysis of higher accuracy as compared with single regression analysis. While multiple regression analysis is most generally used, a number of samples are necessary, and quantitative analytical accuracy is reduced when the correlation between spectral intensity values at each wavenumber is high. On the other hand, the PCR method which is multivariate regression analysis can intensify spectral intensity values in a plurality of wavenumber ranges to principal components which are irrelevant to each other and eliminate unnecessary noise data, whereby high quantitative analytical accuracy can be attained. Further, the PLS method can also utilize data of sample concentrations in extraction of principal components, whereby high quantitative analytical accuracy can be attained similarly to the PCR method. "Tahenryo Kaiseki" (by Kazuo Nakatani, Shinyo-Sha, Japan) can be referred to as to the multivariate regression analysis.

In order to draw out necessary information from spectra which complicatedly fluctuate due to various fluctuation factors, data processing by a computer is highly useful. Typical processing methods are stored in processing software which is provided in a commercially available near-infrared apparatus or the like. An example of such commercially available software is "Unscramber" by COMO Company. Typical processing methods are the aforementioned multiple regression analysis, PLS, the principal component regression analysis etc.

Large streams of data processing which is applied to quantitative analysis are (1) formation of a calibration model, (2) evaluation of the calibration model, and (3) determination of an unknown sample.

In order to perform calibration, it is necessary to measure a proper number of samples for forming a calibration curve in sufficient accuracy. Obtained spectra are subjected to preprocesses at need. Typical preprocesses are smoothing, differentiation and normalization of the spectra, which are general processes.

The calibration is processing of constructing mathematical relational expressions between spectral data and analytical values of target characteristics, i.e., models. Formation of models is performed by a statistical technique by employing analytical values of samples for forming a calibration curve and spectral data. In order to correctly evaluate accuracy of prediction of the prepared calibration curve with respect to an unknown sample, measurement errors with respect to the unknown sample are obtained through an evaluation sample. When the accuracy of the calibration curve is decided as being insufficient, the type of the processing method or parameters are changed at need, to correct the calibration curve.

A calibration curve which is recognized as having sufficient accuracy is employed as a relational expression for predicting values of target characteristics from spectral data in analysis of the unknown sample, to be used for determination of the unknown sample concentration.

FIG. 1 illustrates a general procedure of multivariate regression analysis as a flow chart. Raman scattering spectral measurement of a sample (having known analytical value) for preparing a calibration curve is performed, and preprocesses such as smoothing and normalization are performed at need, for thereafter forming a calibration model from obtained Raman scattering spectral data (Raman scattering spectral intensity at each wavenumber) by performing calibration through multivariate regression analysis.

Then, Raman scattering spectral measurement of an evaluation sample (having known analytical value) for evaluating this calibration model is performed and preprocesses such as smoothing and normalization are performed at need, for thereafter substituting obtained Raman scattering spectral data in the calibration model and comparing a measured value of the evaluation sample and a calculated value from the calibration model with each other, thereby evaluating accuracy of the calibration model. The process returns to the stages of the spectral measurement of the sample for preparing a calibration curve, preprocesses and formation of a calibration model for correcting the calibration model and repeating evaluation by Raman scattering spectral data of the evaluation sample if the accuracy is insufficient. If it is decided that sufficient accuracy is attained, on the other hand, Raman scattering spectral data obtained by Raman scattering spectral measurement of an unknown sample (having unknown analytical value) is substituted in this calibration model, for calculating the concentration.

The present invention is utilized as a technique of a clinical test with a specimen of a body fluid such as urine or blood. Albumin and globulin serve as indices of a nephrosis syndrome and glomerulonephritis, hemoglobin serves as an index for inflammation of an urinary tract system or a tumor, glucose serves as an index of diabetes mellitus, lithium acetoacetate, β-hydroxybutyric acid and acetone serve as indices of ketoacidoses, bilirubin serves as an index of a hepatic/biliary affection, urobilinogen serves as an index of a hepatic/biliary affection or a cythemolytic affection, and sodium nitrite serves as an index of microbism of a urinary tract system respectively. Intra-urinary urea is useful for recognizing internal protein metabolism, a liver/renal function, and sthenia of body protein catabolism or taking of a drug such as quinine is conceivable if the same is increased, while a hepatic parenchymal disease or renal insufficiency is apprehended if the same is reduced. It is been recognized that the amount of intra-urinary urea serves as an index of urine specific gravity ("Shintei Rinsho-Kensa Kenshu Handbook 3" by Nozomu Kosakai, Yakuji-Nippo-Sha, Japan). An osmotic pressure, a refractive index and urine specific gravity are generally excellent in correlation, and determination of these is substituted by the specific gravity ("Rinsho Kensaho Teiyo" by Masamitsu Kanai, Kinbara Shuppan Kabushiki Kaisha, Japan). Further, uric acid serves as an index of urinary calculus and hyperuricemia, folic acid serves as an index of a malabsorption syndrome or a malignant tumor following gastrotomy or enterotomy, creatine serves as an index of a steroid myopathic crisis, creatinine serves as an index of myopathy or nephropathy, and ammonia serves as an index of dysbolism or critical hepatopathy respectively.

Since bilirubin is insoluble in water, ditaurobilirubin was employed in experiments. Ditaurobilirubin is taurine conjugation bilirubin, in which two carbonyl groups are dehydration-bonded with taurine in a common basic chain. As compared with an SERS (surface reinforced Raman spectroscopy) spectrum of bilirubin made by You-Zing Hsieh et al. (Langmuir 1987, 3, 1141–1146), a Raman spectrum obtained this time is substantially identical except a peak around 690.065 $cm^{-1}$, and those other than the same can be regarded as peaks derived from bilirubin. Further, since a peak around 957. 5 $cm^{-1}$ which seems to be $CH_2$ rocking vibration includes vibration of $CH_2$ of a taurine part, it is predictable that relative intensity of bilirubin is slightly lower.

As to urobilin, urobilinogen is so instable that the same is readily converted to urobilin by air oxidation, and hence measurement was made with urobilin. In urobilin, one of —NH— of urobilinogen is oxidized to be —N=. The peak positions of this —NH— are 3530 to 3480 $cm^{-1}$ and concealed by superposition with the position of 0—H stretching vibration (3650 to 3400 $cm^{-1}$) of water which is a solvent, and hence it is predictable that spectra of these are substantially identical to each other.

It is conceivable that peaks of albumin around 2372.8 $cm^{-1}$ result from $NH^+$ stretching vibration.

As to globulin, it is conceivable that peaks around 188.232 $cm^{-1}$ and 423.919 $cm^{-1}$ result from vibration from CCC, those around 653.937 $cm^{-1}$ result from vibration from $CH_2$ or CH, those around 837 $cm^{-1}$ result from vibration from $CH_2$, those around 852 $cm^{-1}$ result from vibration from $CH_2$ CH, those around 1383.49 result from vibration of amide III, those around 1592.41 $cm^{-1}$ result from vibration of amide II, those around 1877.64 $cm^{-1}$ result from vibration from $CH_2$, those around 2125.39 $cm^{-1}$ result from vibration from CC, those around 2370 $cm^{-1}$ result from vibration from $NH^+$, and those around 2433 $cm^{-1}$ result from vibration from SH.

As to hemoglobin, it is conceivable that peaks around 837 $cm^{-1}$ result from vibration from $CH_2$, those around 923. 373 $cm^{-1}$ result from vibration from $CH_3$, those around 1383. 49 result from vibration of amide III, those around 1592. 41 $cm^{-1}$ result from vibration of amide II, those around 1870.82 $cm^{-1}$ result from vibration from $CH_2$, those around 2125.39 $cm^{-1}$ result from vibration from CC, those around 2370 $cm^{-1}$ result from vibration from $NH^+$, and those around 2433 $cm^{-1}$ result from vibration from SH. A spectrum of oxyhemoglobin by resonance Raman spectroscopy is described in "Raman Spectroscopy" (by P. R. Carey), and hence it was referred to.

As to D-glucose, it is conceivable that peaks around 405 $cm^{-1}$ result from vibration from CCO, those around 524 $cm^{-1}$ are basic chain vibration, those around 648 $cm^{-1}$ result from vibration from CC, those around 779 $cm^{-1}$ and around 840 $cm^{-1}$ result from vibration from CH, those around 914 $cm^{-1}$ result from vibration from CH and COH, those around 1054 $cm^{-1}$ result from vibration from CH, those around 1076 $cm^{-1}$ result from vibration from CH and COH, those around 1276 $cm^{-1}$ and 1346 $cm^{-1}$ result from vibration from COH, those around 1426 $cm^{-1}$ result from vibration from $CH_2$, those around 1640 $cm^{-1}$ result from vibration from HOH, and those around 2900 $cm^{-1}$ result from vibration from CH and $CH_2$.

As to lithium acetoacetate, it is conceivable that peaks around 829.379 $cm^{-1}$, around 1383.49 $cm^{-1}$ and 1870.82

$cm^{-1}$ result from vibration from $CH_2$, and those around 2937 $cm^{-1}$ result from vibration from $CH_3$ and $CH_2$.

As to β-hydroxybutyric acid, it is conceivable that peaks around 1450.98 $cm^{-1}$ result from vibration from $CH_2$ and vibration from $CO_2$, those around 1587.69 $cm^{-1}$ result from vibration from $CO_2$, those around 1630 $cm^{-1}$ result from vibration from CO, those around 2900 $cm^{-1}$ result from vibration from $CH_2$, and those around 2959 $cm^{-1}$ result from vibration from $CH_3$.

As to acetone, it is conceivable those peaks around 805 $cm^{-1}$, around 1080 $cm^{-1}$, around 1429 $cm^{-1}$ and around 2940 $cm^{-1}$ result from vibration from $CH_3$, those around 1237 $cm^{-1}$ result from vibration from $CH_3C$, and those around 1710 $cm^{-1}$ result from vibration from CO.

As to ditaurobilirubin, it is conceivable that peaks around 690.065 $cm^{-1}$ result from vibration from CC, those around 957.5 $cm^{-1}$ and around 1458.88 $cm^{-1}$ result from vibration from $CH_2$, those around 1263.96 $cm^{-1}$ result from vibration from $CH_2$ and vibration from CO, and those around 1616.29 $cm^{-1}$ result from vibration from CC and vibration from CO.

No Raman peak was attained in relation to urobilin, since fluorescence provided in itself was strong.

As to sodium nitrite, it is conceivable that peaks around 813 $cm^{-1}$ and around 1339.5 $cm^{-1}$ result from vibration from NO.

As to urea, it is conceivable that peaks around 531, 939 $cm^{-1}$, around 1008 $cm^{-1}$ and around 1168.35 $cm^{-1}$ result from vibration from CN, those around 597.248 $cm^{-1}$ result from vibration from CO, and those around 1613.67 $cm^{-1}$ result from vibration from CO and $NH_2$.

When urine is measured as a sample, it is possible to correct uric component concentrations varying with the urine amount by standardizing concentrations of other uric components with reference to the concentration of creatinine having a constant excretal amount per time.

According to the present invention, it is possible to directly determine a sample without through mediational reaction such as enzyme reaction or chemical reaction or intermediate reaction. Since no reagent is employed, influences are hardly exerted by coexistent substances and errors following reaction can be eliminated. No operation such as reaction is required between sampling and measurement, whereby the measurement can be simply and quickly performed.

The present invention is also effective for detection of small change or components of small amounts, due to its high sensitivity. Thus, the present invention is suitable for application to qualitative and quantitative tests of intraurinary microprotein.

According to the present invention, it is possible to quantitatively analyze components in a body fluid by obtaining intensity values of proper wavenumber positions as to a plurality of body fluid components to be measured from spectra obtained by irradiating a body fluid sample with excitation light, whereby expendable items such as test papers and reagents are unnecessary and no problem of disposal after employment is caused.

Even if there is interference by other components in the body fluid, a plurality of components in the body fluid can be simultaneously qualitatively/quantitatively analyzed by utilizing a technique such as multivariate regression analysis.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIGS. 9A and 9B illustrate light scattering spectra obtained from aqueous albumin samples with application of excitation beams of 632.8 nm and 514.5 nm in wavelength emitted from an He—Ne laser unit and an Ar laser unit respectively;

FIGS. 11A and 11B illustrate light scattering spectra obtained from aqueous γ-globulin samples with application of excitation beams of 632.8 nm and 514.5 nm in wavelength emitted from an He—Ne laser unit and an Ar laser unit respectively;

FIG. 62 illustrates measured wavenumbers in components in body fluids; and

FIG. 63 shows correlation diagrams of values of a plurality of components in urine calculated by multivariate regression analysis and measured values.

DESCRIPTION OF THE PREFERRED EMBODIMENTS

Some examples of measuring apparatuses for carrying out the inventive measuring method are shown in FIGS. 2 to 7.

Figure 2:
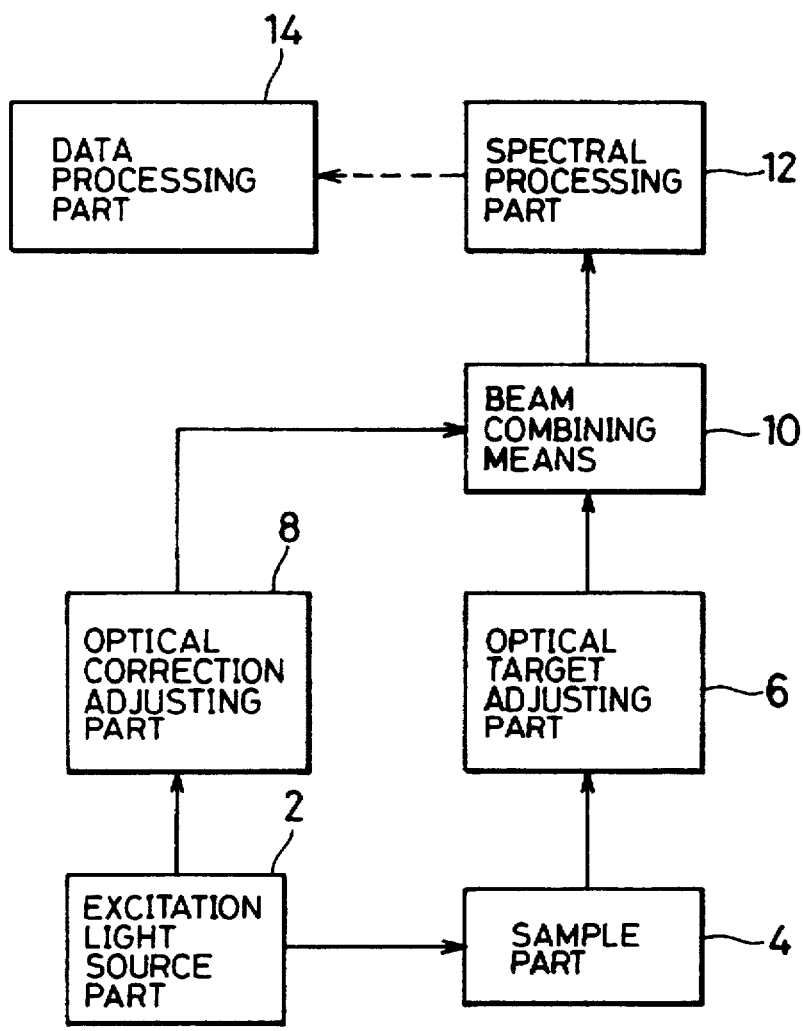
FIG. 2 is a block diagram schematically showing a measuring apparatus for carrying out the present invention.

FIG. 2 schematically illustrates the measuring apparatus, which comprises an excitation light source part 2 provided with an excitation light source and a beam splitter dividing a beam from the excitation light source into a sample beam and a correction beam, a sample part 4 for irradiating a sample with the sample beam, an optical target adjusting part 6 provided with a filter for removing the same wavelength component as the excitation light from scattered light generated from the sample irradiated with the sample beam and selecting target light including fluorescence and Raman scattered light and an optical system for adjusting beams, an optical correction adjusting part 8 for adjusting the correction beam divided by a half mirror in the excitation light source part 2, beam combining means 10 for placing a beam outgoing from the optical target adjusting part 6 and the correction beam outgoing from the optical correction adjusting part 8 on the same optical axis, one spectral processing part 12 provided with a spectroscope for separating a beam outgoing from the beam combining means 10 into its spectral components and a detector for detecting spectral light separated by the spectroscope, and a data processing part 14 having a function of correcting target light intensity on the basis of detected intensity of the excitation light component in spectra detected by the detector of the spectral processing part 12.

The correction beam is adapted to correct fluctuation of the light emission intensity of the light source, and the beam splitter provided in the excitation light source part 2, the optical correction adjusting part 8 and the beam combining means 10 are unnecessary if such correction is not performed.

The filter provided in the optical target adjusting part 6 is preferably any one of a holographic notch filter including the excitation light wavelength in its notch region, a cut filter shielding the excitation light wavelength and a shorter wavelength side therefrom, a bandpass filter having characteristics of removing by transmitting the excitation light wavelength component and reflecting a target light component, and a holographic beam splitter removing the excitation light wavelength by transmission or reflection.

The spectral processing part 12 is preferably a polychrometer comprising a multichannel photodetector for simultaneously detecting wavelength regions to be measured. When the spectral processing part 12 is a polychrometer, it is possible to simultaneously detect wavelength regions to be measured, i.e., to simultaneously detect a target light spectrum of a prescribed region and the excitation light. Consequently, no difference is caused between detection times of the respective wavelengths of the target light and the excitation light. If difference between the detection times of the respective wavelengths of the target light and the excitation light is permitted, a wavelength scanning type spectroscope and a single channel photodetector may be comprised as the spectral processing part 12, for successively detecting the wavelength regions to be measured.

The holographic notch filter is adapted to shield only a desired wavelength region, while transmitting wavelength light of other regions. When a filter which is so set that the excitation light wavelength is included in the shielded region (notch region) is employed, a beam outgoing from the optical target adjusting part 6 includes only the target light component, with no excitation light component. On the other hand, the correction beam includes only the excitation light from the light source and passes through no sample, whereby the same expresses intensity fluctuation from the light source in fidelity with dependence on no sample.

FIGS. 3 to 7 show concrete examples expressing the block diagram of FIG. 2 in detail.

Figure 3:
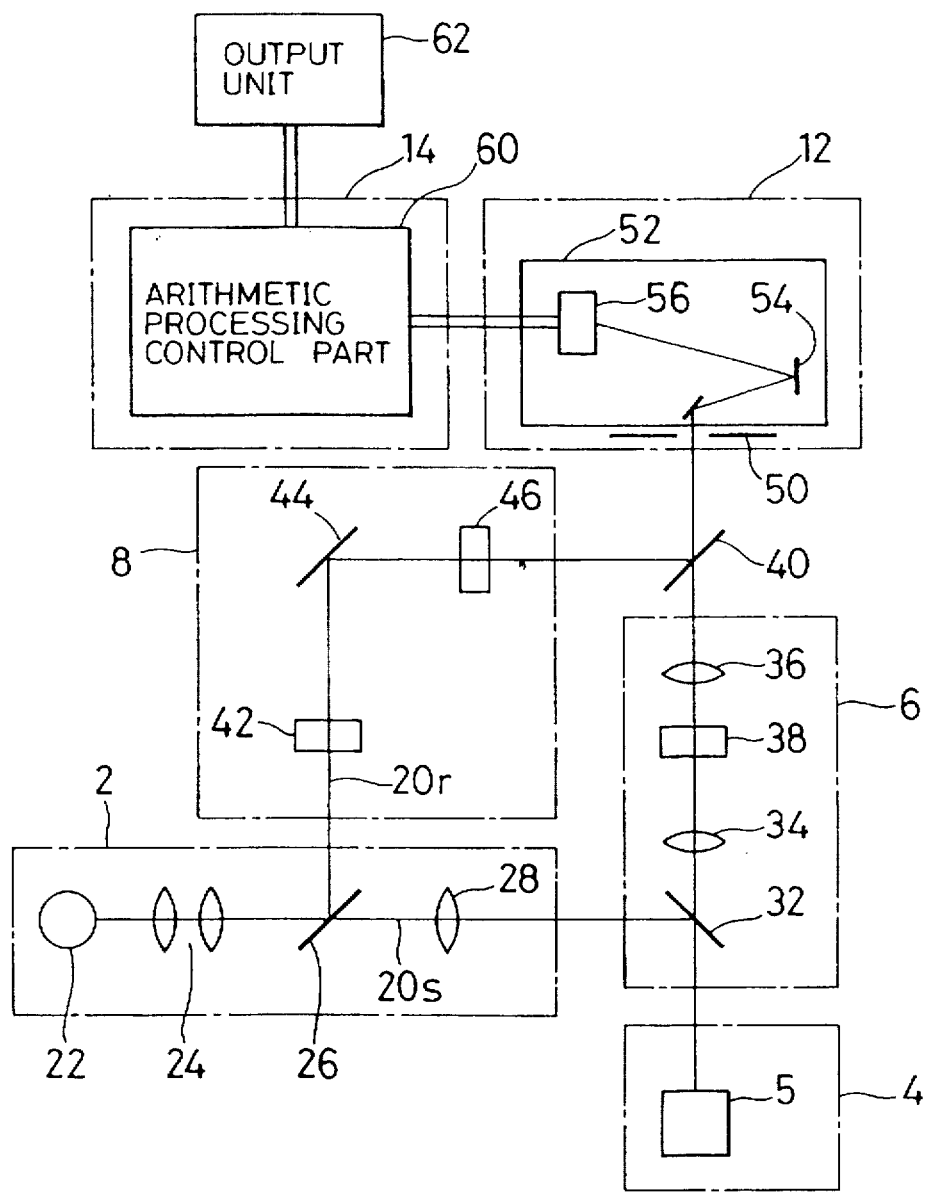
FIG. 3 is an arrangement diagram showing a measuring apparatus employing a holographic notch filter as filter means of an optical target adjusting part for receiving target light in a direction of 180 degrees to excitation light with respect to a sample.

FIG. 3 illustrates an embodiment employing a holographic notch filter including an excitation light wavelength in its notch region or a cut filter shielding the excitation light wavelength and a shorter wavelength side therefrom as filter means of an optical target adjusting part 6, for receiving target light in a direction of 180 degrees to excitation light with respect to a sample. A light source 22 is provided on an excitation light source part 2, and a half mirror 26 is arranged as a beam splitter for dividing excitation light from the light source 22 into a sample beam 20s and a correction bream 20r. The light source 22 can be formed by a laser unit, for example. The laser unit can be selected from laser units of wide wavelength regions over near ultraviolet to near infrared regions such as a continuously oscillating Ar ion laser unit, a Kr ion laser unit, an He—Ne laser unit, an He—Cd laser unit, an Nd:YAG laser unit, a semiconductor laser unit and a pulse laser unit. Alternatively, a light source generating multiwavelength light such as a halogen lamp may be combined with wavelength selection means such as a spectroscope, to be employed as a light source other than the laser unit.

In order to converge the sample beam 20s on a sample 5 of a sample part 4, a light source condenser lens 24 and a convergent lens 28 are arranged in the excitation light source part 2 on both sides of the half mirror 2. The sample 5 is stored in a cell and set in the sample part 4.

The sample beam 20s from the excitation light source part 2 is reflected by a half mirror 32 which is arranged in the optical target adjusting part 6, and applied to the sample 5 of the sample part 4. The optical target adjusting part 6 is provided with condenser lenses 34 and 36, in order to converge scattered light from the sample 5 transmitted through the half mirror 32 on an inlet slit 50 of a spectroscope. A holographic notch filter 38 which is set to include the wavelength of the excitation light in its notch region is arranged on the optical target adjusting part 6 between the condenser lenses 34 and 36, as a filter for removing the same wavelength component as the excitation light and selecting target light. Such a holographic notch filter is available on Kaiser Optical Systems Inc., U.S.A., for example. The holographic notch filter 38 has characteristics of completely shielding wavelength light included in its notch region and transmitting at least 80% of light of a wavelength region other than the notch region, for example.

A half mirror 40 is arranged between the condenser lens 36 of the optical target adjusting part 6 and the inlet slit 50 of the spectroscope as a beam combining means, so that the target light is transmitted through the half mirror 40 and incident upon a spectroscope 52.

An optical correction adjusting part 8 is set for guiding the correction beam 20r which is divided by the half mirror 26 in the excitation light source part 2 to the half mirror 40 of the beam combining means, and an extinction filter 42 for damping the light quantity, a bandpass filter 46 for shielding the wavelength light generated in the half mirror 26 of the excitation light source part 2 for shielding a sideband from a laser beam when the light source 22 is a laser unit, and a mirror 44 for bending an optical path are arranged on the optical correction adjusting part 8. The correction beam 20r which is guided to the inlet slit 50 by the optical correction adjusting part 8 through the half mirror 40 is converged on the inlet slit 50 by the light source condenser lens 24.

The target light outgoing from the optical target adjusting part 6 and the correction beam 20r guided from the optical correction adjusting part 8 are guided onto the same optical axis in the half mirror 40, and guided to a spectroscope 52 of a spectral processing part 12 through the inlet slit 50. The spectroscope 52 is a polychrometer, which comprises a diffraction grating 54 for separating incident light into its spectral components, and a multichannel photodetector 56 provided with a plurality of photodetector elements along a dispersion direction of the diffraction grating 54 in order to simultaneously detect the spectral light components separated by the diffraction grating 54 over a prescribed wavelength region. While the diffraction grating 54 shown in FIG. 3 is a concave diffraction grating, a specthroscope called a Czerny-Turner spectroscope combining a plane diffraction grating with a spherical mirror or that employing a transmission type diffraction grating may alternatively be employed. Numeral 60 denotes an arithmetic processing control part for controlling operations of the respective parts and processing signals detected by the photodetector 56. This arithmetic processing control part 60 also includes a function for serving as a data processing part correcting detected intensity of the target light on the basis of that of the excitation light component among spectra detected by the photodetector 56, for calculating a Raman scattering spectrum in which fluctuation of the light source is corrected and performing qualification and determination of the sample from the target light intensity. Numeral 62 denotes an output unit such as a printer or a display outputting data processed in the arithmetic processing control part 60.

In the embodiment shown in FIG. 3, the holographic notch filter 38 may be replaced with a sharp cut filter having sharp wavelength characteristics, shielding the excitation light wavelength and a shorter wavelength side therefrom.

Describing operations of this embodiment, the sample beam 20s from the light source part 2 is reflected by the half mirror 32 which is arranged on the optical target adjusting part 6, and applied to the sample 5 of the sample part 4. Scattered light from the sample 5 is passed through the optical target adjusting part 6 so that the same wavelength component as the excitation light is removed, and incident upon the spectroscope 52 from the inlet slit 50 through the half mirror 40. On the other hand, the correction beam 20r which is divided by the half mirror 26 in the excitation light source part 2 is passed through the optical correction adjusting part 8 so that its light quantity is adjusted, and incident upon the spectroscope 52 through the inlet slit 50 through the half mirror 40. Fluctuation of spectral light intensity caused by fluctuation of the excitation light intensity is corrected by the correction beam 20r, so that light scattering spectral intensity of each component is detected.

Figure 4:
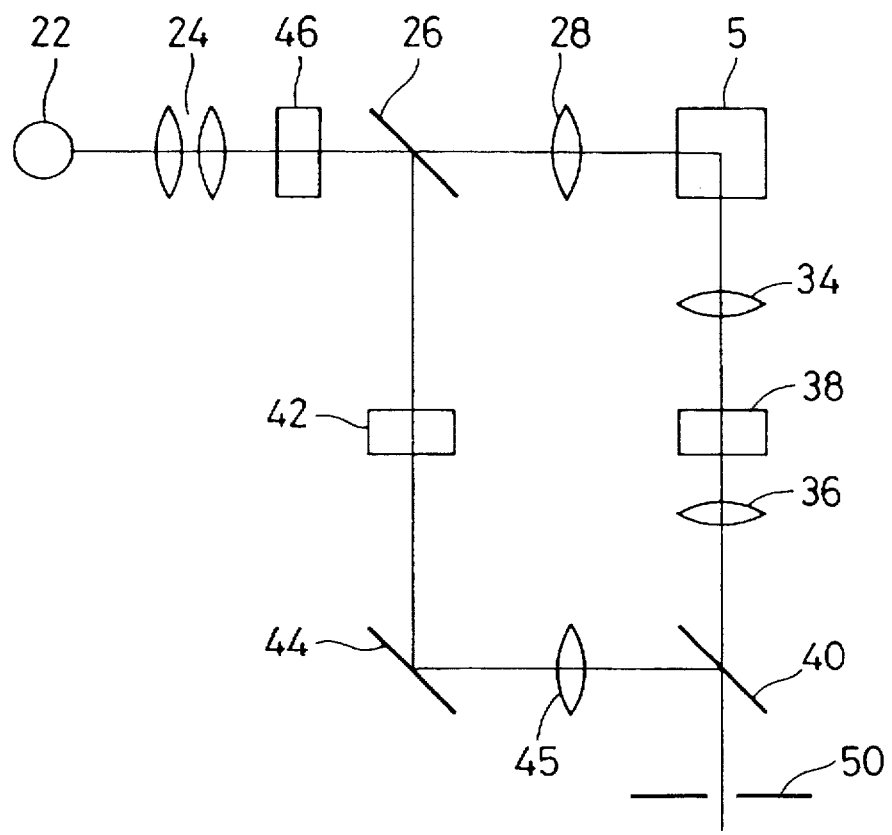
FIG. 4 is an arrangement diagram showing a measuring apparatus employing a holographic notch filter as filter means of an optical target adjusting part for receiving target light in a direction of 90 degrees to excitation light with respect to a sample.

FIG. 4 illustrates an embodiment employing a holographic notch filter or a cut filter as a filter means of an optical target adjusting part 6 similarly to the embodiment shown in FIG. 3, while target light is received in a direction of 90 degrees to excitation light with respect to a sample. In this case, no half mirror 32 in FIG. 3 is necessary for irradiating a sample 5 with a sample beam 20s and introducing scattered light from the sample 5 into a condenser lens 34 of the optical target adjusting part 6. The sample beam 20s is converged by a light source condenser lens 24 and a convergent lens 28 of the excitation light source part 2 and directly applied to the sample 5, so that the scattered light from the sample 5 is directly incident upon the condenser 34 of the optical target adjusting part 6.

While the bandpass filter 46 shown in FIG. 3 is arranged on the optical path of the optical correction adjusting part 8, that in FIG. 4 is arranged on an optical path before the beam splitter 26. It is possible to shield a sideband of a laser beam from both of the sample and correction beams by arranging such a bandpass filter 46 on the position shown in FIG. 4.

While a condenser lens 45 is further arranged on an optical axis of an optical correction adjusting part in FIG. 4, this lens 45 is a light quantity adjusting lens for converging the correction beam to the position of a slit 50, and the same is unnecessary when the light quantity of the correction beam is sufficiently large.

Figure 5A:
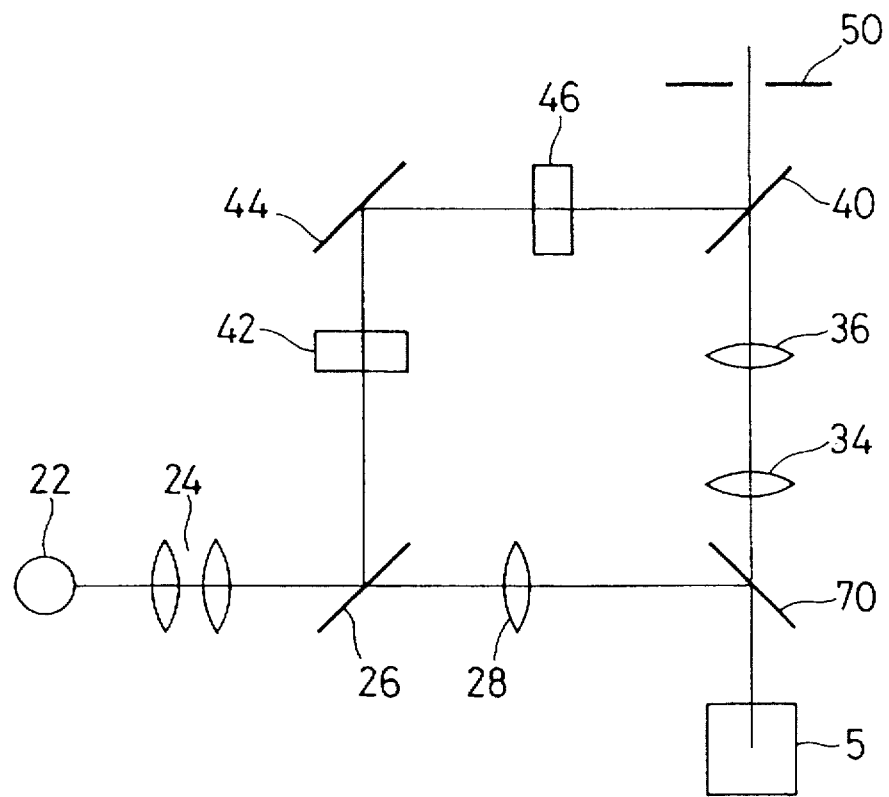
FIG. 5A is an arrangement diagram showing a measuring apparatus employing a holographic beam splitter as filter means of an optical target adjusting part for receiving target light in a direction of 180 degrees to excitation light with respect to a sample.

FIG. 5A illustrates an embodiment employing a holographic beam splitter 70 having characteristics of reflecting excitation light and transmitting Raman light as a filter means of an optical target adjusting part 6, for receiving target light in a direction of 180 degrees to the excitation light with respect to a sample.

Figure 5B:
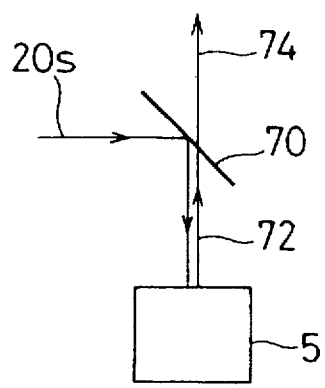
FIG. 5B is a schematic sectional view showing the holographic beam splitter part in FIG. 5A.

As shown in FIG. 5B, the holographic beam splitter 70 reflects a sample beam 20s and applies the same to a sample 5, and transmits only target light 74 in scattered light 72 from the sample 5 including the target light 74 and Rayleigh scattered light for introducing the target light 74 into a condenser lens 34 of the optical target adjusting part 6.

Figure 6A:
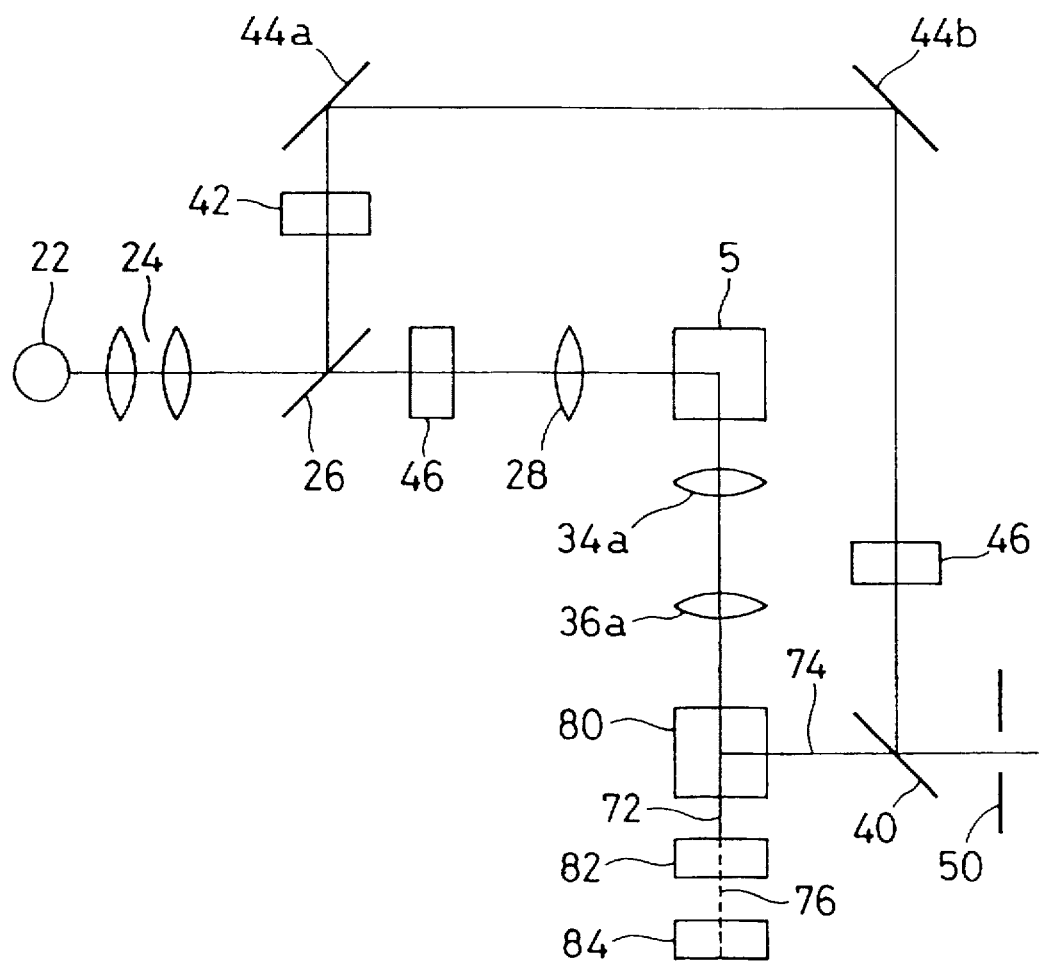
FIG. 6A is an arrangement diagram showing a measuring apparatus employing a bandpass filter as filter means of an optical target adjusting part for receiving target light in a direction of 90 degrees to excitation light with respect to a sample.

FIG. 6A illustrates an embodiment employing a bandpass filter 82 having characteristics of removing by transmitting an excitation light wavelength component and selecting by reflecting a target light component as a filter means of an optical target adjusting part 6, for receiving target light in a direction of 90 degrees to the excitation light with respect to a sample.

Figure 6B:
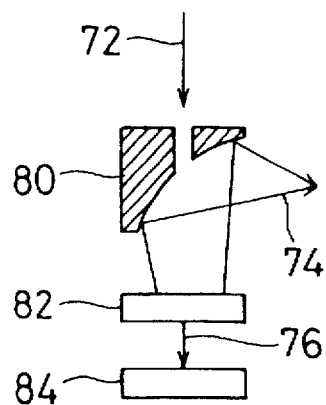
FIG. 6B is a schematic sectional view showing the bandpass filter part.

As shown in FIG. 6B, the bandpass filter 82 is arranged on a mirror surface side of a transmission/converging type mirror 80, while a beam stopper 84 is arranged on a side opposite to the transmission/converging type mirror 80. Scattered light 72 from a sample 5 including target light a n d Rayleigh scattered light is condensed by condenser lenses 34a and 34b, and incident upon the bandpass filter 82 through its incidence hole from a back surface of the transmission/converging type mirror 80. Rayleigh light 76 is transmitted through the bandpass filter 82 and absorbed by the beam stopper 84, while target light 74 is reflected and converged by the mirror surface of the transmission/converging type mirror 80, and incident upon a spectroscope from an inlet slit 50 through a half mirror 40. Two mirrors 44a and 44b are arranged in an optical correct ion adjusting part 8, in order to bend an optical path by 180 degrees.

Figure 7:
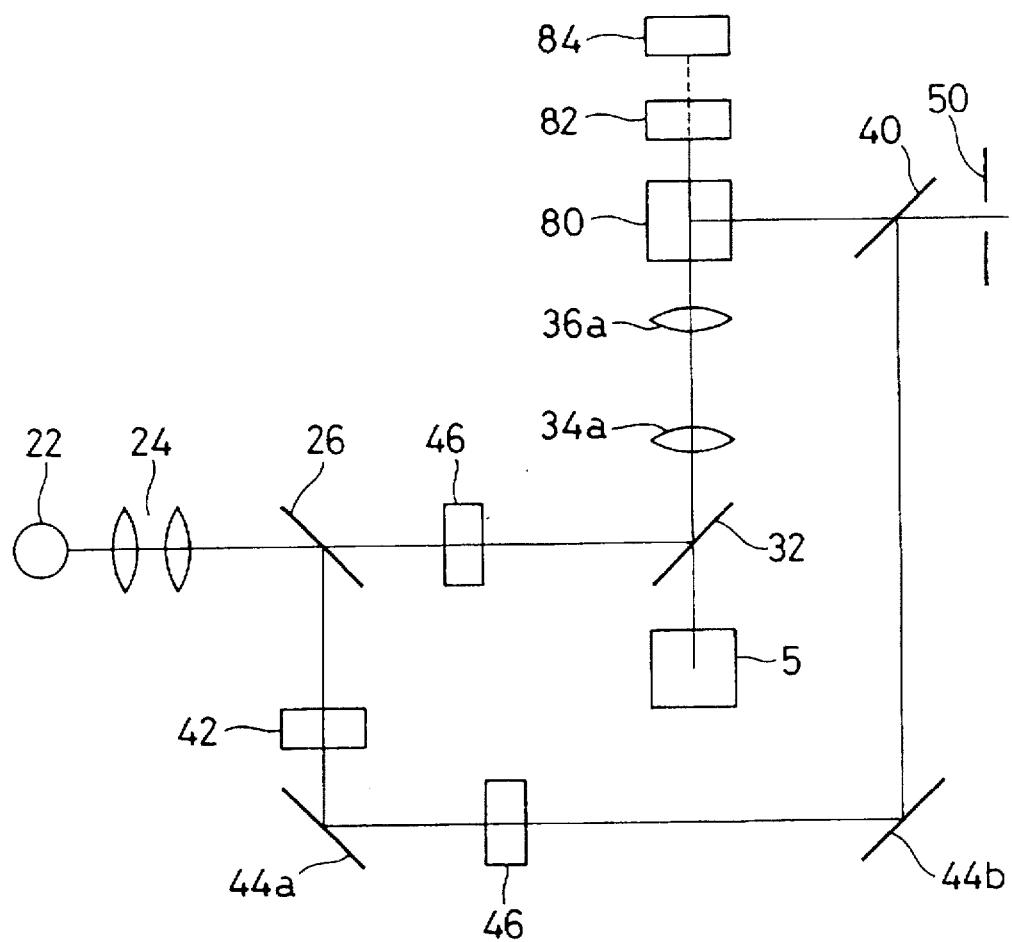
FIG. 7 is an arrangement diagram showing a measuring apparatus employing a bandpass filter as filter means of an optical target adjusting part for receiving target light in a direction of 180 degrees to excitation light with respect to a sample.

FIG. 7 illustrates an embodiment employing a bandpass filter 82 having characteristics of removing by transmitting an excitation light wavelength component and selecting by reflecting a target light component as a filter means of an optical target adjusting part 6 similarly to that shown in FIG. 6A, for receiving target light in a direction of 180 degrees to the excitation light with respect to a sample. A half mirror 32 is arranged for applying a sample beam 20s to a sample 5 and introducing scattered light from the sample 5 into a condenser lens 34a of the optical target adjusting part 6.

Figure 8:
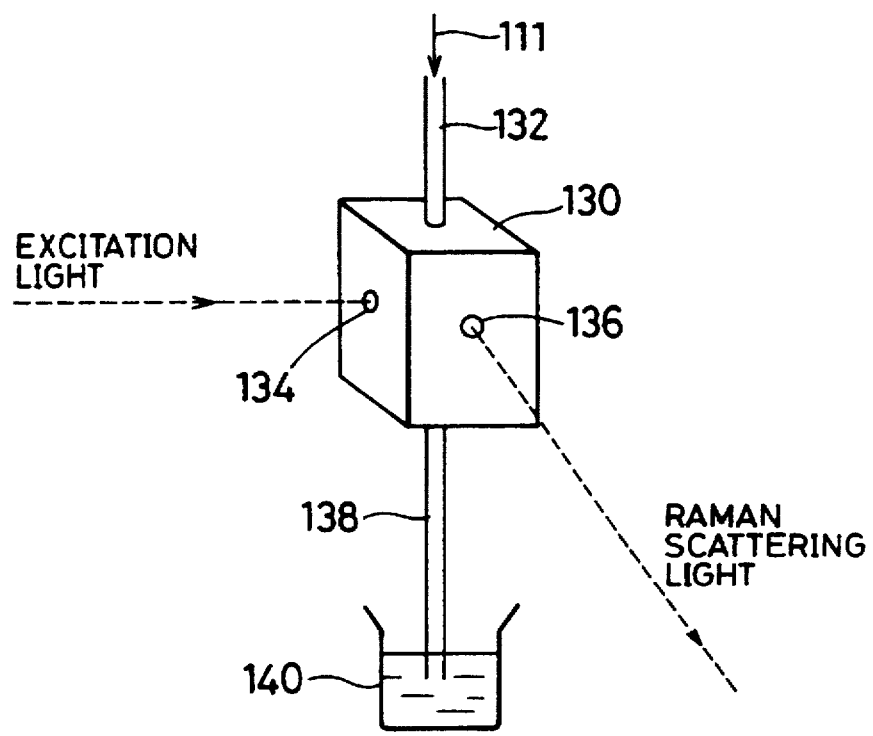
FIG. 8 is a perspective view showing paths for introducing and discharging a target substance in case of employment of a flow cell.

FIG. 8 illustrates exemplary paths for introducing and discharging a target substance 111 in case of employing a flow cell. The target substance 111 flows into a flow cell of a cell holder 130 from a specimen solution inlet line 132 and the flow cell is irradiated with excitation light which is introduced from an excitation light entrance window 134 provided on a side surface of the cell holder 130, so that Raman light excited in the flow cell outgoes from a Raman light outgoing window 136 and enters the optical target adjusting part 6. After measurement, the target substance 111 is discharged in a waste water bottle 140 through a specimen solution discharge line 138. This specimen solution discharge line 138 may directly communicate with a channel for sewage or the like.

While a direction θ for receiving target light is at 90 ° with respect to excitation light in the flow cell shown in FIG. 8, the present invention is not restricted to this but the Raman light outgoing window 136 may be located in any position so far as $0° \leq \theta < 360°$.

FIGS. 9 to 15 show results of measurement made on aqueous solutions of albumin, γ-globulin and hemoglobin, which are intra-urinary protein, respectively.

(EXAMPLE 1)

FIGS. 9A, 9B, 10A and 10B show measurement results as to aqueous albumin solutions (derived from human serums). FIGS. 9A and 9B show light scattering spectra obtained by employing an He—Ne laser unit (output: 7 mW) and an Ar laser unit (output: 10 mW) as excitation light sources and applying beams of 632.8 nm and 514.5 nm in wavelength to sample aqueous solutions as excitation beams respectively. Both spectra have broad shapes over the ranges of 100 to 3100 $cm^{-1}$ or more from the excitation wavelengths.

Figure 10A:
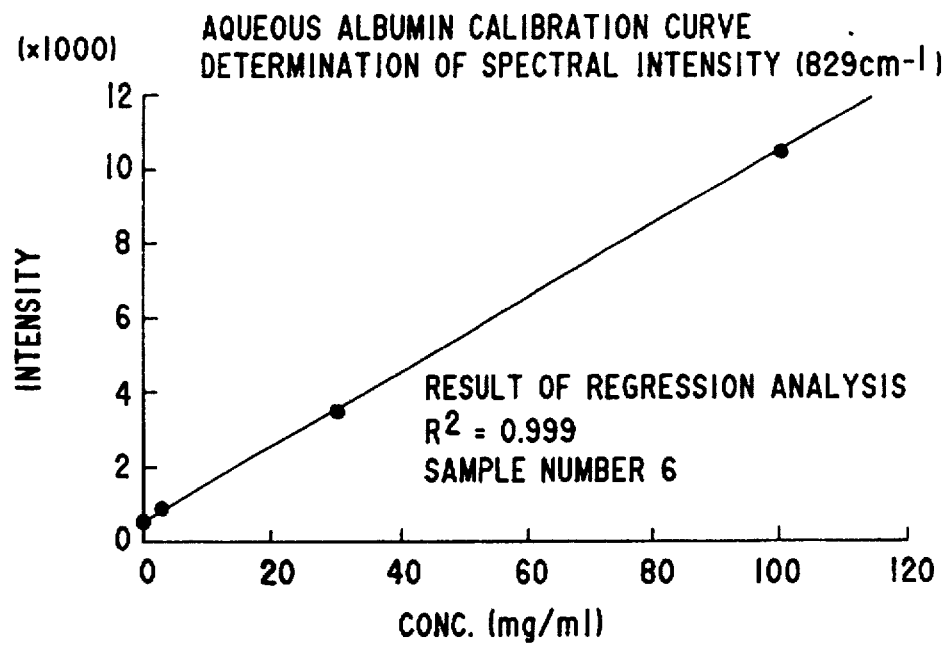
FIGS. 10A and 10B illustrate the correlations between the spectral intensity at a position of a shift wavenumber of 829 $cm^{-1}$ and the area in the range of shift wavenumbers of 256 to 1620 $cm^{-1}$ in the light scattering spectrum shown in FIG. 9A respectively.
Figure 10B:
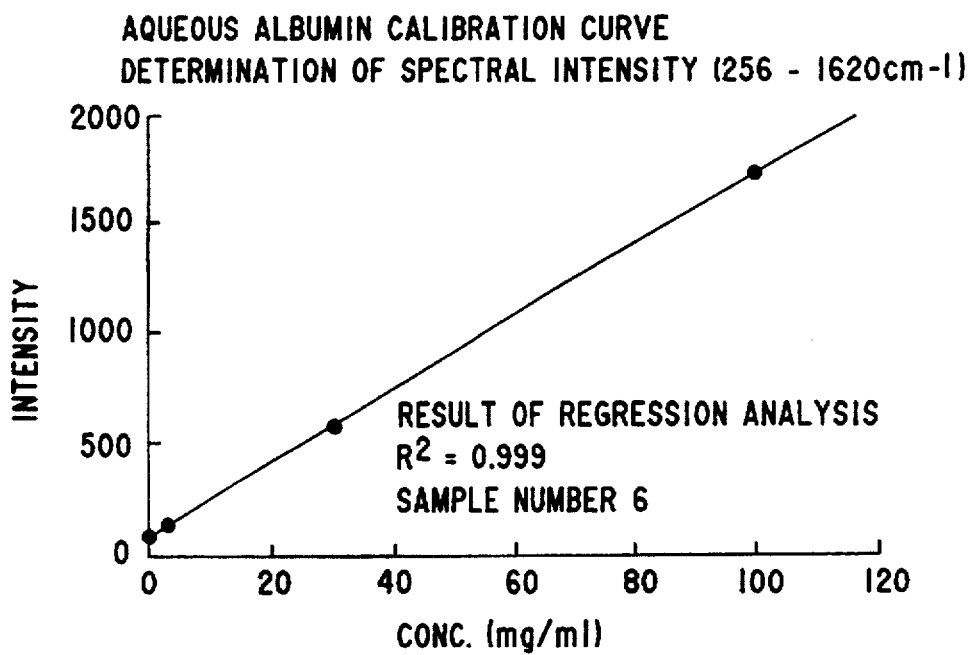

FIG. 10A illustrates a result of measurement of the correlation between spectral intensity at a position of a shift wavenumber of 829 $cm^{-1}$ and the albumin concentration in the sample through the light scattering spectrum of FIG. 9A. FIG. 10B illustrates a result of measurement of the correlation between the area in the range of shift wavenumbers of 256 to 1620 $cm^{-1}$ and the albumin concentration in the sample.

Both of FIGS. 10A and 10B show excellent results with correlation coefficients $R^2$ of at least 0.99. It is possible to quantitatively analyze albumin concentrations in samples by utilizing these correlations as calibration curves.

(EXAMPLE 2)

FIGS. 11A to 12F show measurement results as to aqueous γ-globulin solutions (derived from human serums).

FIGS. 11A and 11B show light scattering spectra obtained by employing an He—Ne laser unit (output: 7 mW) and an Ar laser unit (output: 10 mW) as excitation light sources and applying beams of 632.8 nm and 514.5 nm in wavelength to sample aqueous solutions as excitation beams respectively.

The spectrum shown in FIG. 11A has sharp peaks in positions shifted from the excitation wavelength to 175 to 195 $cm^{-1}$, 425 to 450 $cm^{-1}$, 640 to 670 $cm^{-1}$, 820 to 845 $cm^{-1}$, 845 to 870 $cm^{-1}$, 1370 to 1400 $cm^{-1}$, 1575 to 1620 $cm^{-1}$, 1850 to 1900 $cm^{-1}$, 2000 to 2200 $cm^{-1}$, 2350 to 2400 $cm^{-1}$ and 2400 to 2460 in a spectrum of a broad shape over 100 to 4000 $cm^{-1}$ from the excitation wavelength. The spectrum shown in FIG. 11B has a broad shape over 100 to 4000 $cm^{-1}$ from the excitation wavelength.

FIGS. 12A to 12F show results of measurement of the correlations between spectral intensity levels at positions of shift wavenumbers of 837.257 $cm^{-1}$, 1383.49 $cm^{-1}$, 1592 $cm^{-1}$, 1877 $cm^{-1}$, 2125 $cm^{-1}$ and 2370 $cm^{-1}$ and γ-globulin concentrations in samples through the spectrum shown in FIG. 11A.

Figure 12A:
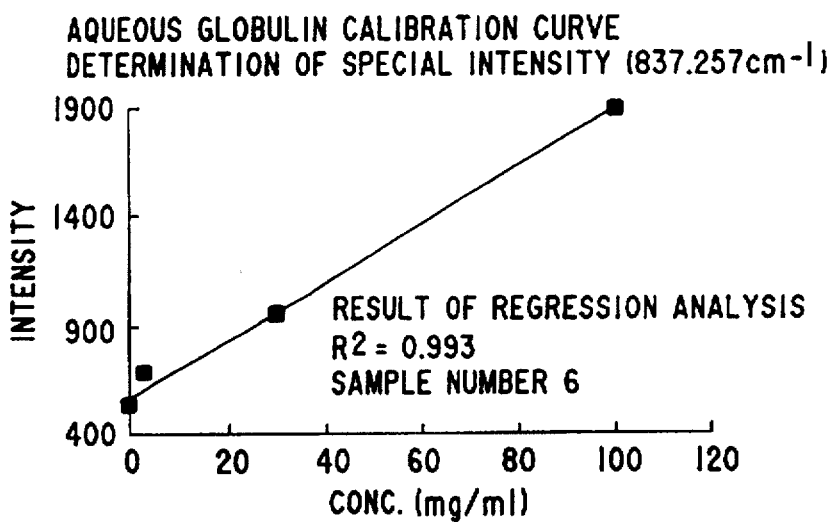
FIGS. 12A to 12F illustrate the correlations between spectral intensity levels at positions of shift wavenumbers of 837.257 $cm^{-1}$, 1383.49 $cm^{-1}$, 1592 $cm^{-1}$, 1877 $cm^{-1}$, 2125 $cm^{-1}$ and 2370 $cm^{-1}$ and γ-globulin concentrations in samples in the light scattering spectrum of FIG. 11A respectively.
Figure 12B:
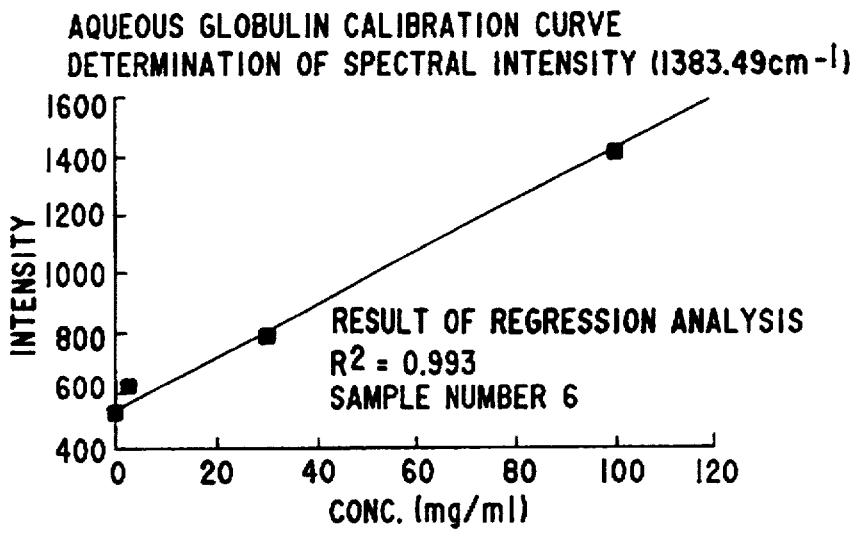
Figure 12C:
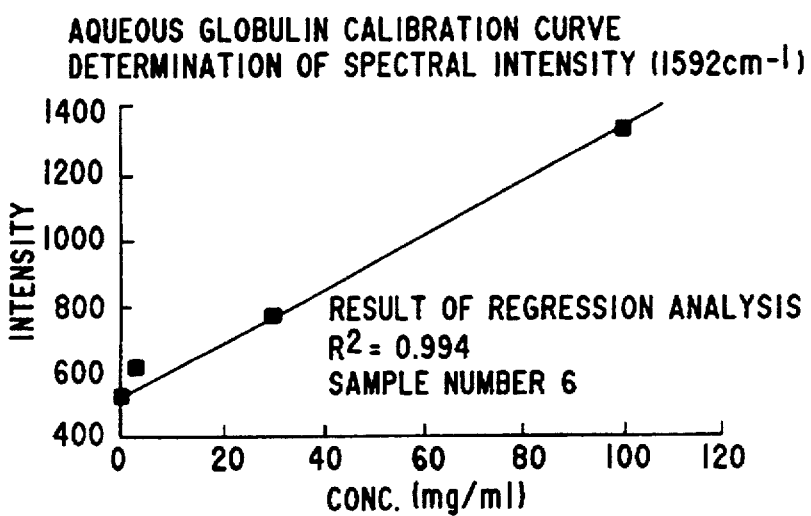
Figure 12D:
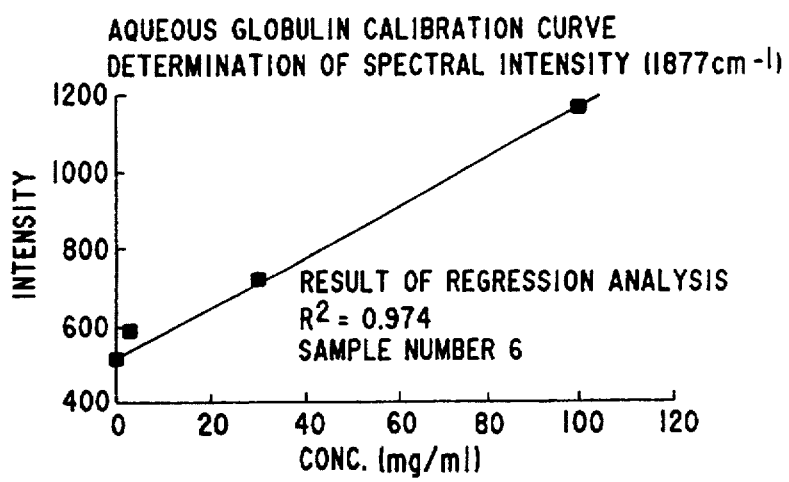
Figure 12E:
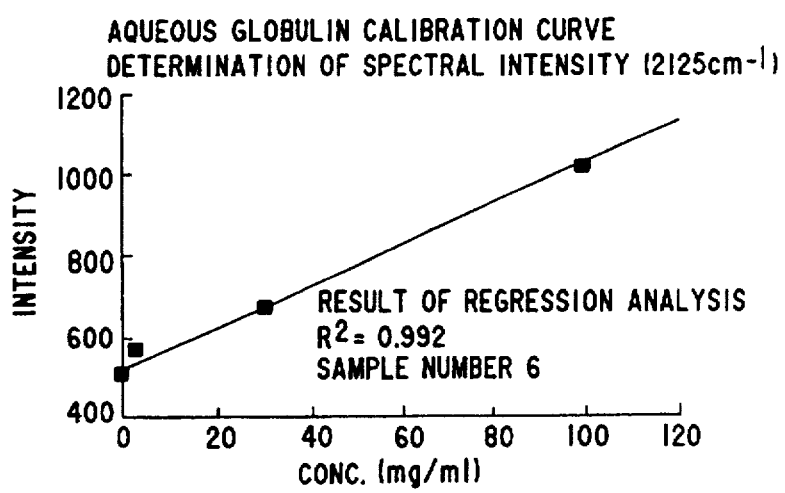
Figure 12F:
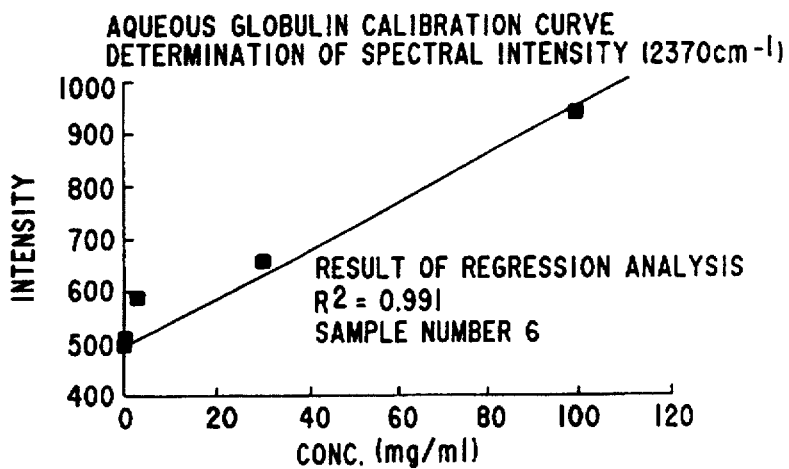

The correlation coefficient $R^2$ of the correlation shown in FIG. 12D is at least 0.97, and the correlation coefficients $R^2$ of the remaining correlations are at least 0.99 in excellent results. Also as to peak intensity values in other shift wavenumber positions and integrated intensity values of proper wavenumber ranges, excellent correlations were obtained as to γ-globulin concentrations.

It is possible to quantitatively analyze γ-globulin concentrations in samples by employing these correlations as calibration curves.

(EXAMPLE 3)

Figure 13A:
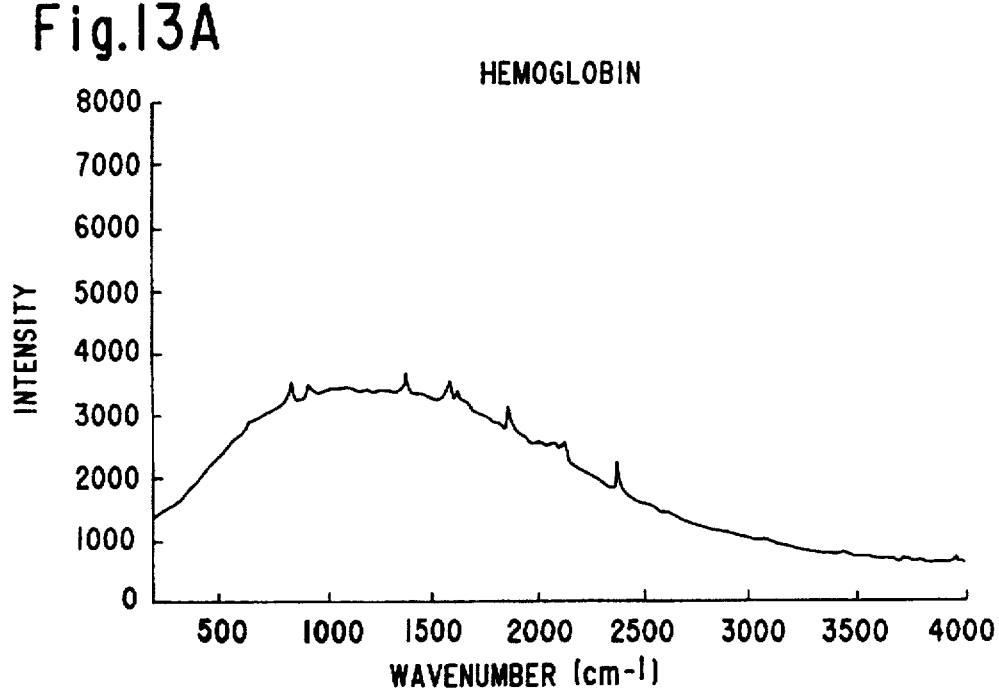
FIGS. 13A and 13B illustrate light scattering spectra obtained from aqueous hemoglobin samples with application of excitation beams of 632.8 nm and 514.5 nm in wavelength emitted from an He—Ne laser unit and an Ar laser unit respectively.
Figure 13B:
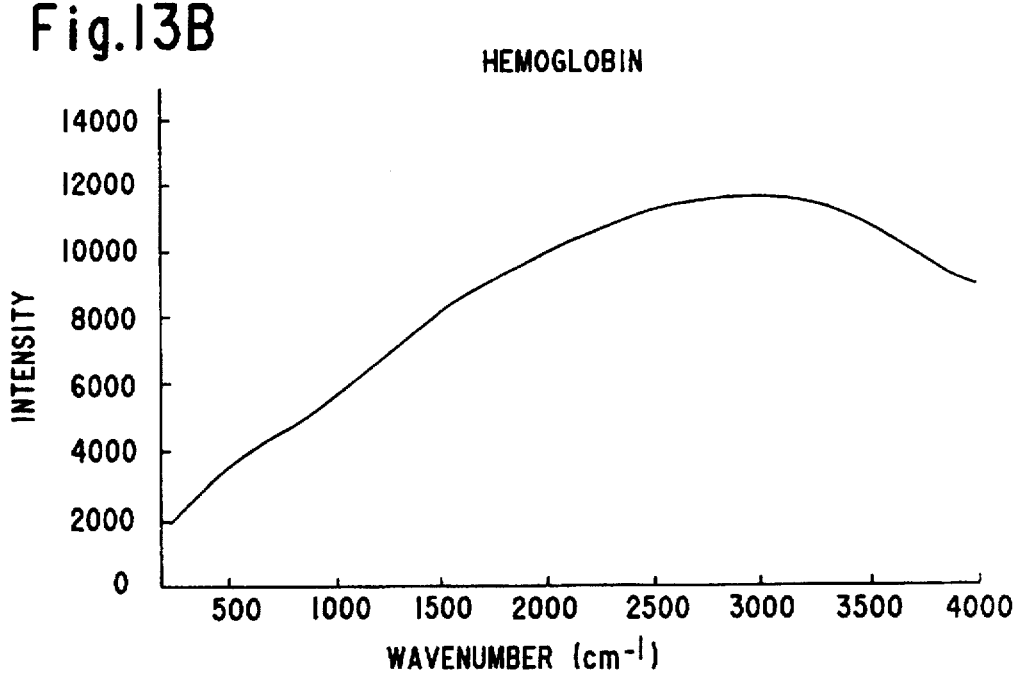

FIGS. 13A to 14C show measurement results as to aqueous hemoglobin solutions (derived from bovine serums). FIGS. 13A and 13B show light scattering spectra obtained by employing an He—Ne laser unit (output: 7 mW) and an Ar laser unit (output: 10 mW) as excitation light sources and applying beams of 632.8 nm and 514.5 nm in wavelength to sample aqueous solutions as excitation beams respectively.

The spectrum shown in FIG. 13A has sharp peaks in positions shifted from the excitation wavelength to 640 to 670 $cm^{-1}$, 820 to 845 $cm^{-1}$, 1370 to 1400 $cm^{-1}$, 1575 to 1620 $cm^{-1}$, 1850 to 1900 $cm^{-1}$, 2000 to 2200 $cm^{-1}$, 2350 to 2400 $cm^{-1}$ and 2400 to 2460 in a spectrum of a broad shape over 100 to 4100 $cm^{-1}$ from the excitation wavelength. The spectrum shown in FIG. 13B has a broad shape over 100 to 4100 $cm^{-1}$ from the excitation wavelength.

Figure 14A:
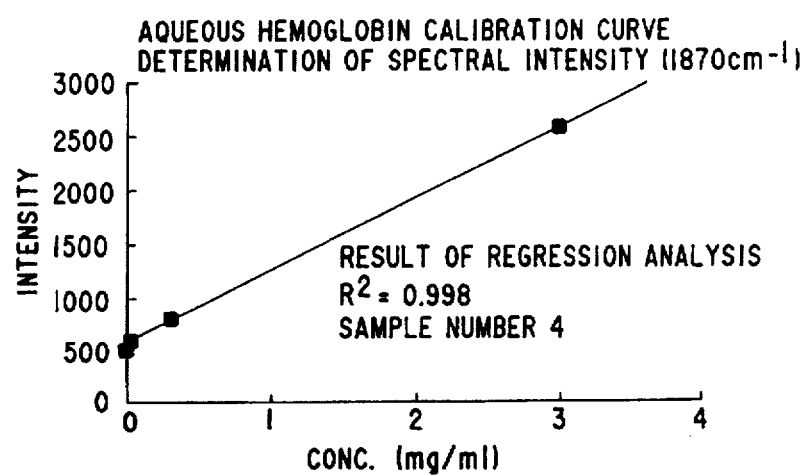
FIGS. 14A to 14C illustrate the correlations between spectral intensity levels at positions of shift wavenumbers of 1870 cm$^{-1}$, 2125 cm$^{-1}$ and 2370 cm$^{-1}$ and hemoglobin concentrations in samples in the light scattering spectrum of FIG. 13A respectively.
Figure 14B:
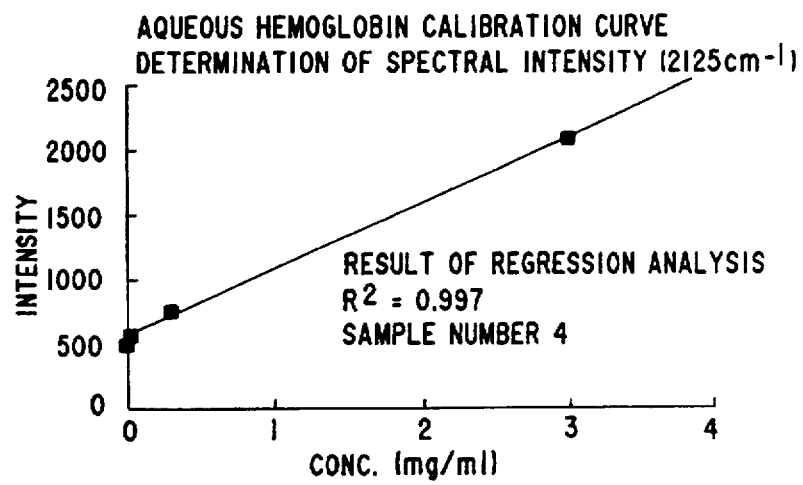
Figure 14C:
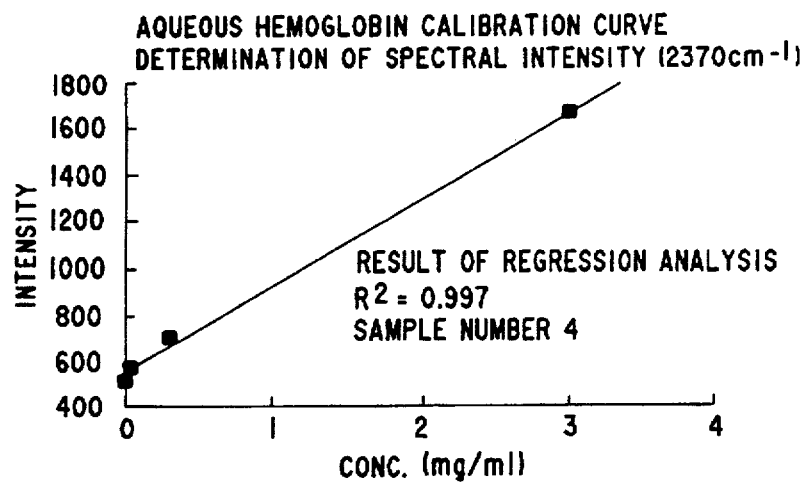

FIGS. 14A to 14C show results of measurement of the correlations between spectral intensity levels at positions of shift wavenumbers of 1870 $cm^{-1}$, 2125 $cm^{-1}$ and 2370 $cm^{-1}$ and hemoglobin concentrations in samples through the light scattering spectrum shown in FIG. 13A.

The correlation coefficients $R^2$ of all correlations exhibit excellent results of at least 0.99. It is possible to quantitatively analyze hemoglobin concentrations in samples by employing these correlations as calibration curves.

(EXAMPLE 4)

Figure 15:
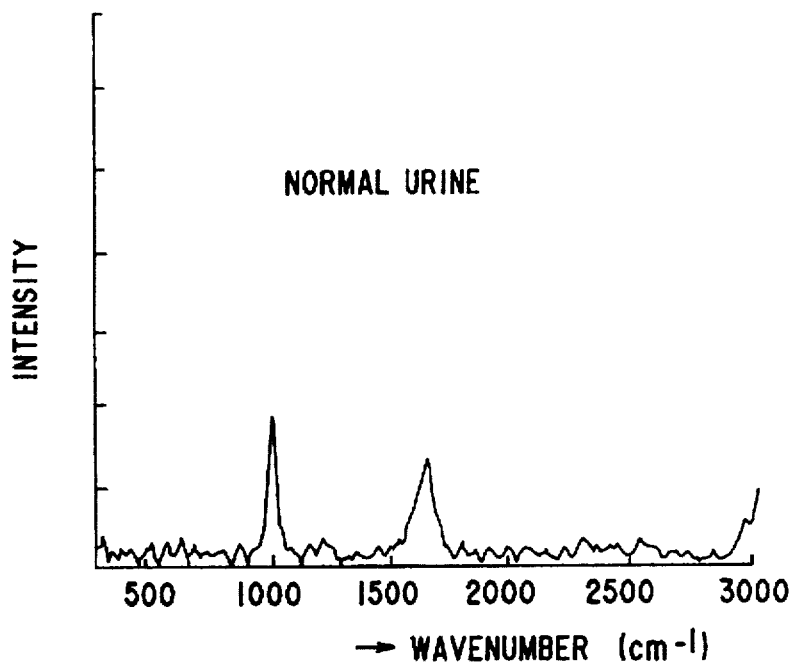
FIG. 15 illustrates the Raman spectrum of normal urine.

Raman Measurement of Normal Urine:

FIG. 15 shows the Raman spectrum of normal urine. A peak around 1000 $cm^{-1}$ was derived from urea, and peaks around 1650 $cm^{-1}$ and more than 3000 $cm^{-1}$ were derived from water serving as a solvent.

(EXAMPLE 5)

Figure 16:
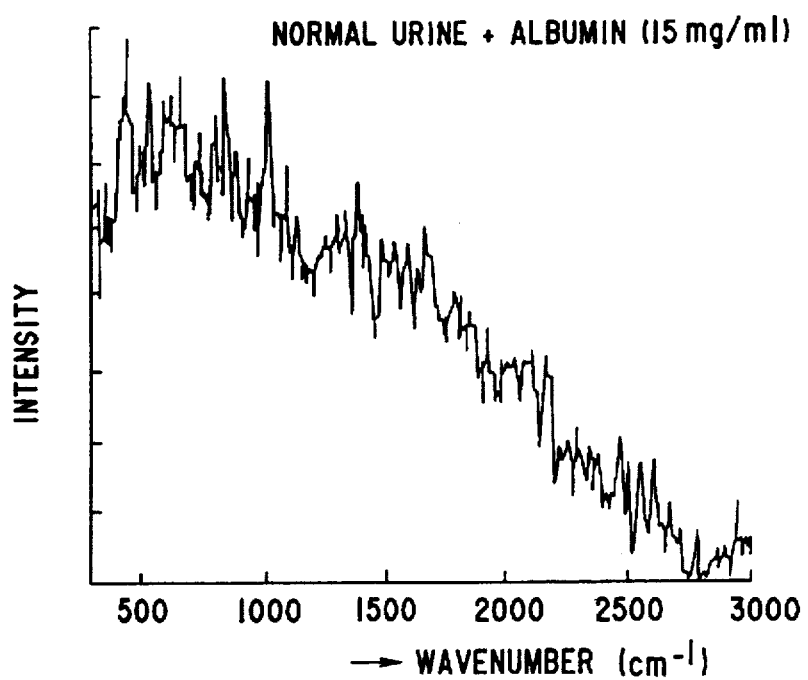
FIG. 16 illustrates the Raman spectrum of a sample prepared by extending the amount of albumin in normal urine by about 15 mg/ml.
Figure 17:
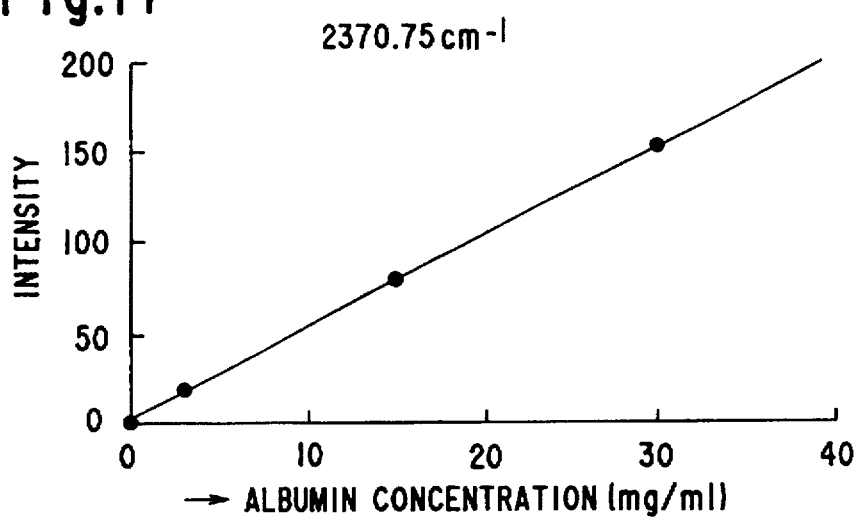
FIG. 17 illustrates the correlation between the albumin concentration in urine and Raman scattered light intensity at a wavenumber of 2370.75 cm$^{-1}$.

Determination of Intra-Urinary Albumin through Raman Spectroscopy:

FIGS. 16 and 17 show results of measurement made by adding albumin to a normal urine. FIG. 16 illustrates the spectrum of a sample prepared by extending albumin in normal urine by about 15 mg/ml. This spectrum is a composite one since a plurality of components were present at different concentrations in the urine. FIG. 17 shows a result of investigation as to the correlation between intensity of 2370 cm$^{-1}$ of this spectrum and the concentrations.

(EXAMPLE 6)

Figure 18:
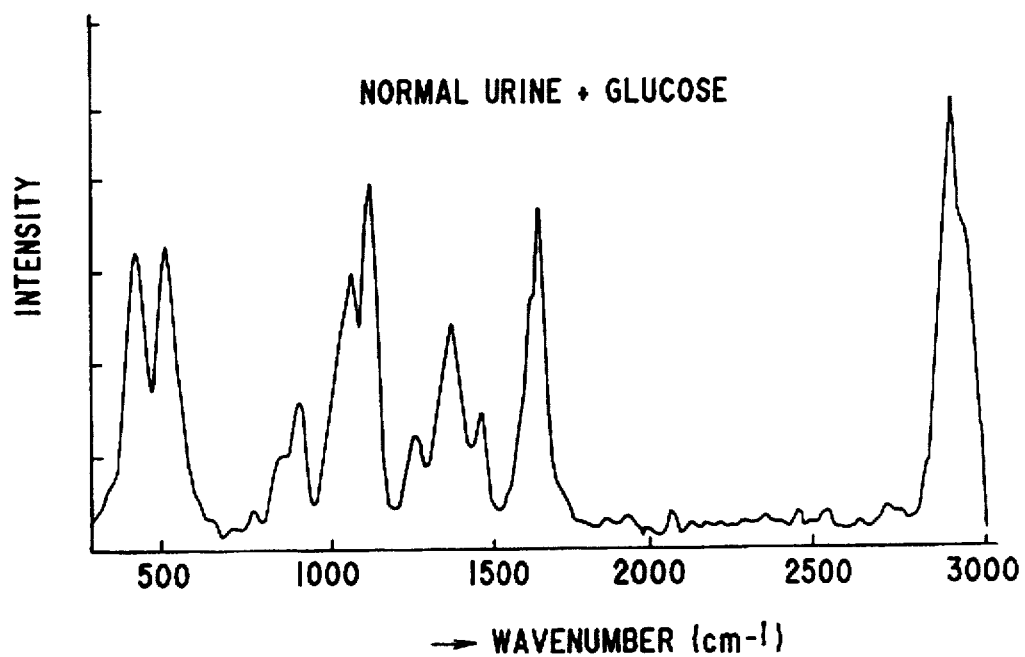
FIG. 18 illustrates the Raman spectrum of a sample prepared by extending the amount of glucose in normal urine by a saturation amount.
Figure 19:
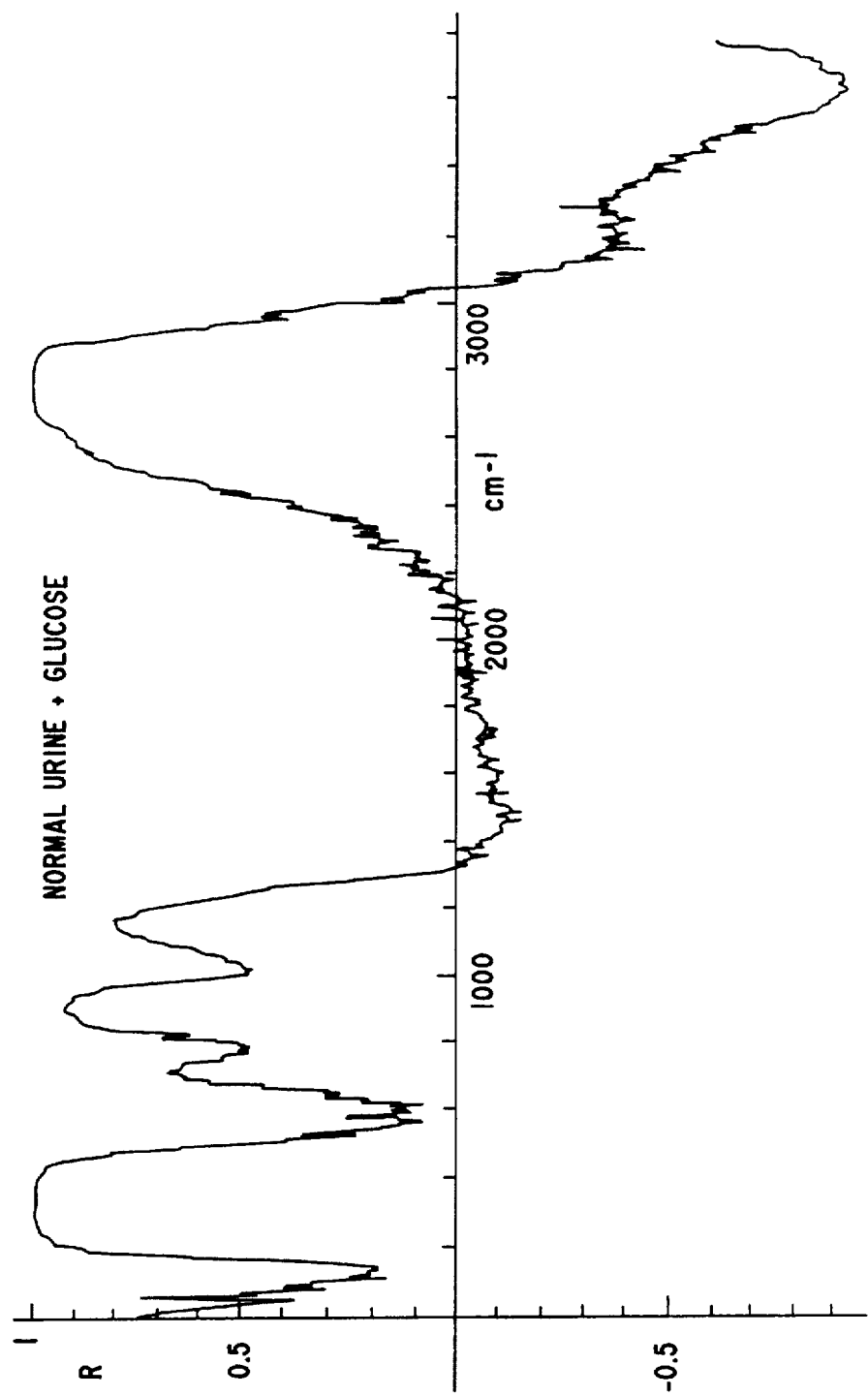
FIG. 19 illustrates the correlations between glucose concentrations in urine and Raman scattered light intensity levels at wavenumbers of 0 to 4000 cm$^{-1}$.

Determination of Intra-Urinary Glucose through Raman Spectroscopy:

FIGS. 18 and 19 show results of measurement made by adding glucose to a normal urine. FIG. 18 illustrates the spectrum of a sample prepared by extending glucose in normal urine by a saturation amount. FIG. 19 shows a result of investigation on the correlation between Raman spectral intensity at wavenumbers of 0 to 4000 cm$^{-1}$ and the concentrations.

(EXAMPLE 7)

Figure 20:
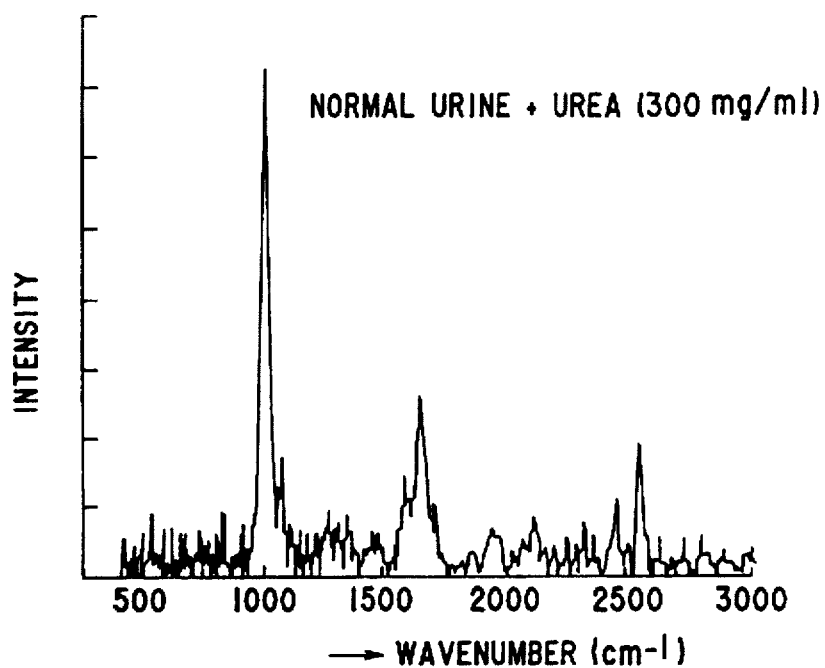
FIG. 20 illustrates the Raman spectrum of a sample prepared by extending the amount of urea in normal urine by about 300 mg/ml.
Figure 21:
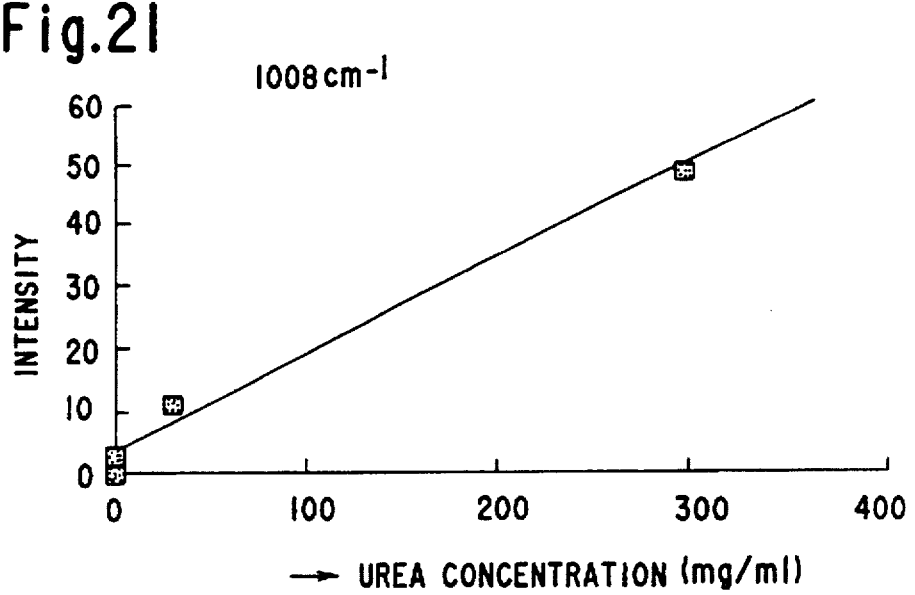
FIG. 21 illustrates the correlation between the urea concentration in urine and Raman scattered light intensity at a wavenumber of 1008 cm$^{-1}$.

Determination of Intra-Urinary Urea through Raman Spectroscopy:

FIGS. 20 and 21 show results of measurement made by adding urea to a normal urine. FIG. 20 illustrates the spectrum of a sample prepared by extending glucose in normal urine by 300 mg/ml. FIG. 21 shows a result of investigation on the correlation between intensity at 1008 cm$^{-1}$ and the concentrations.

(EXAMPLE 8)

Figure 22:
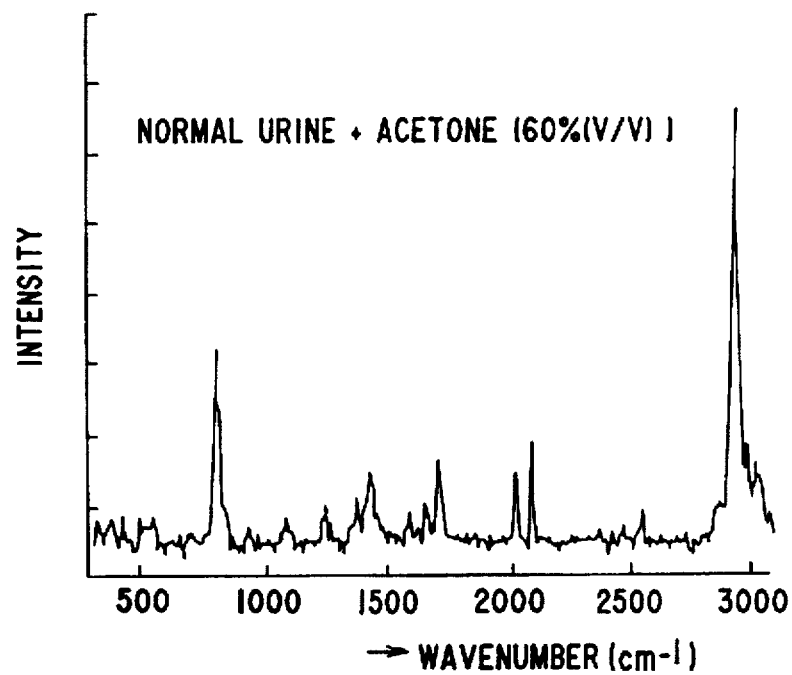
FIG. 22 illustrates the Raman spectrum of a sample prepared by extending the amount of acetone in normal urine to be about 60% (V/V)
Figure 23:
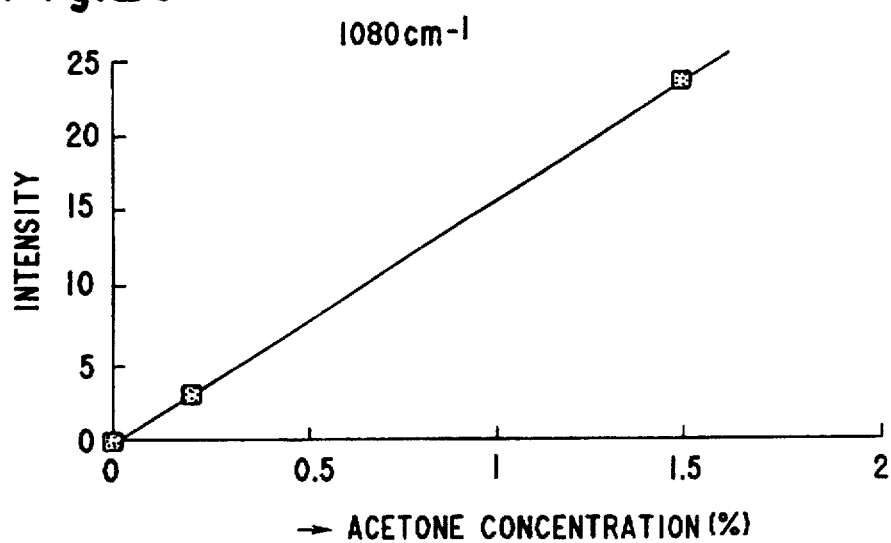
FIG. 23 illustrates the correlation between the acetone concentration in urine and Raman scattered light intensity at a wavenumber of 1080 cm$^{-1}$.

Determination of Intra-Urinary Acetone through Raman Spectroscopy:

FIGS. 22 and 23 show results of measurement made by adding acetone to a normal urine. FIG. 22 illustrates the spectrum of a sample prepared by extending acetone in normal urine by 60% (V/V). FIG. 23 shows a result of investigation on the correlation between intensity at 1080 cm$^{-1}$ and the concentrations.

(EXAMPLE 9)

Figure 24:
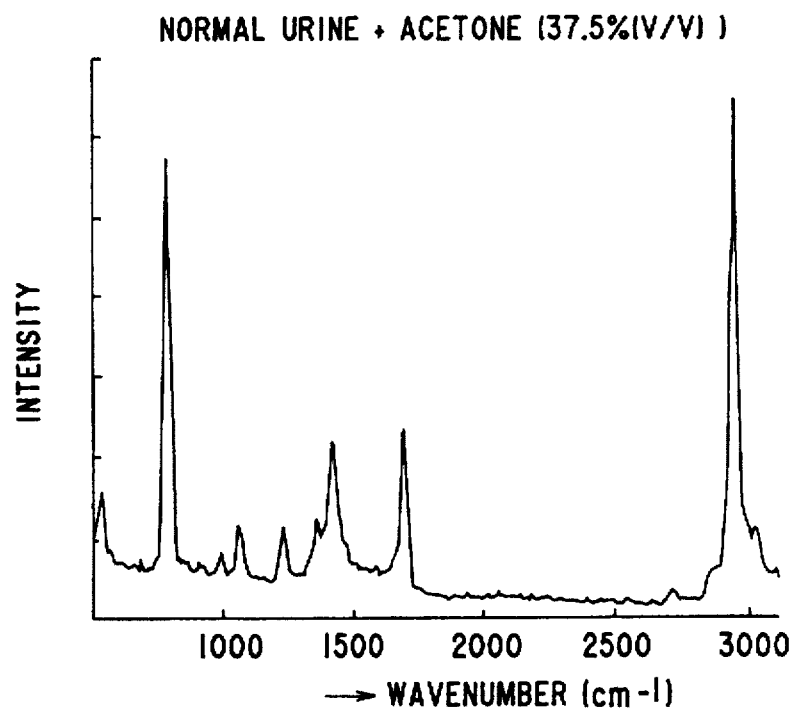
FIG. 24 illustrates the Raman spectrum of a sample prepared by extending the amount of acetone in normal urine to be 37.5% (V/V)
Figure 25:
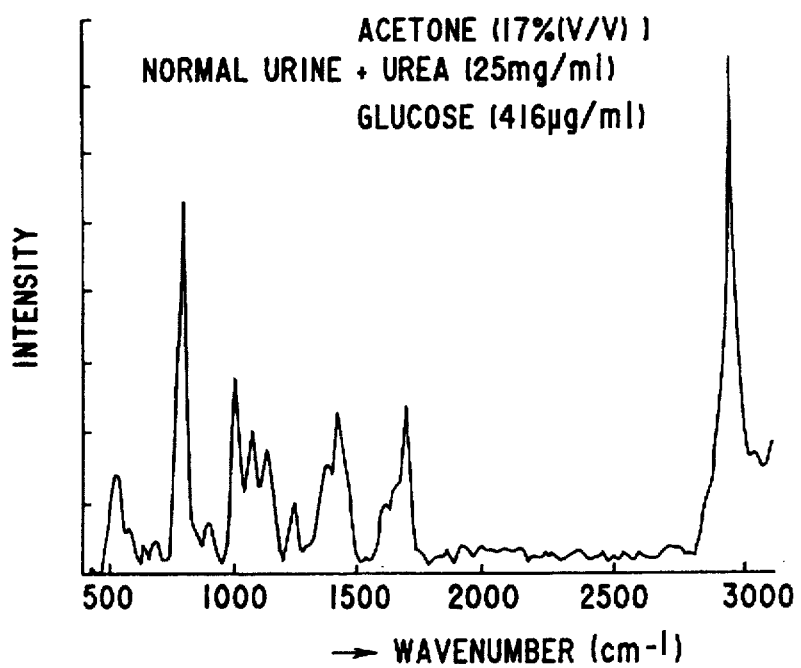
FIG. 25 illustrates the Raman spectrum of a sample prepared by extending the amounts of acetone, urea and glucose in normal urine to be 17% (V/V), 25 mg/ml and 416 μg/ml respectively.
Figure 26:
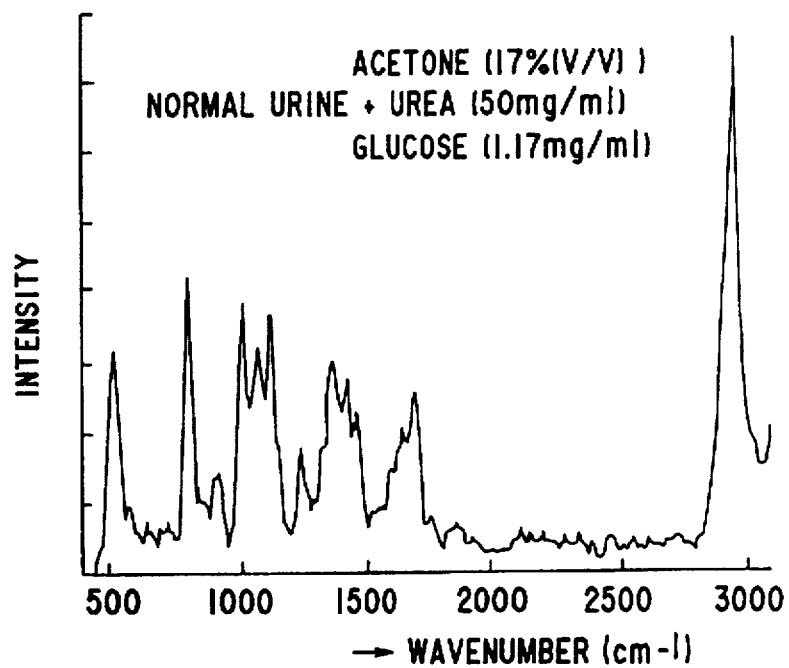
FIG. 26 illustrates the Raman spectrum of a sample prepared by extending the amounts of acetone, urea and glucose in normal urine to be 17% (V/V), 50 mg/ml and 1.17 mg/ml respectively.
Figure 27:
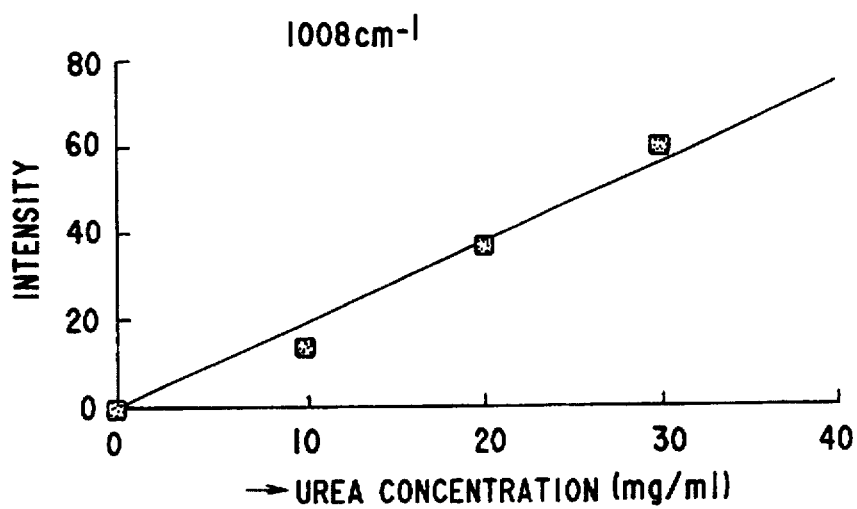
FIG. 27 illustrates the correlation between the urea concentration in urine and Raman scattered light intensity at a wavenumber of 1008 cm$^{-1}$.
Figure 28:
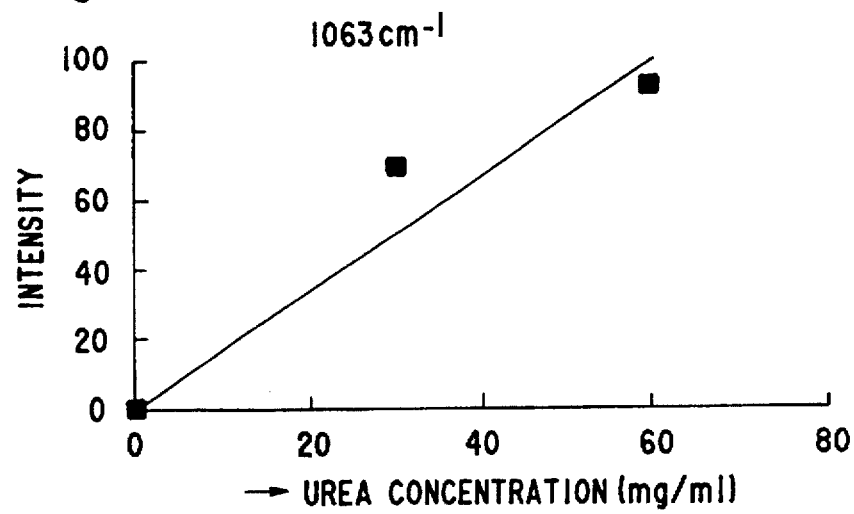
FIG. 28 illustrates the correlation between the urea concentration in urine and Raman scattered light intensity at a wavenumber of 1063 cm$^{-1}$.
Figure 29:
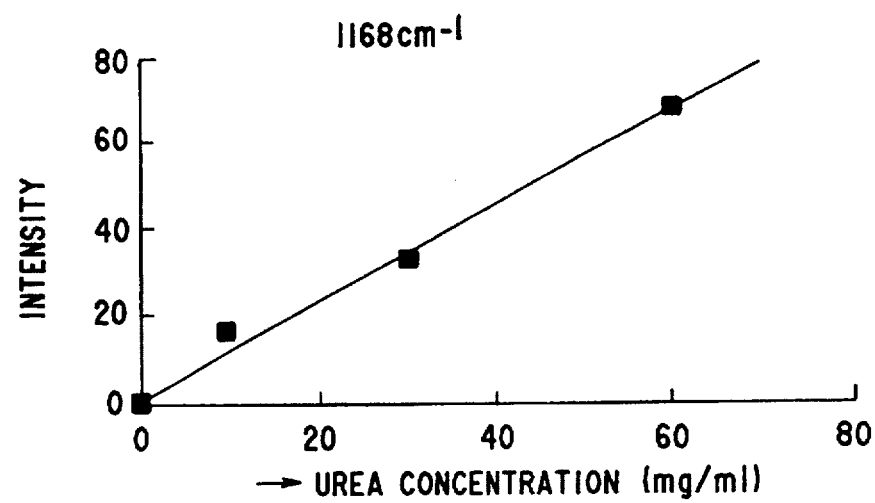
FIG. 29 illustrates the correlation between the urea concentration in urine and Raman scattered light intensity at a wavenumber of 1168 cm$^{-1}$.
Figure 30:
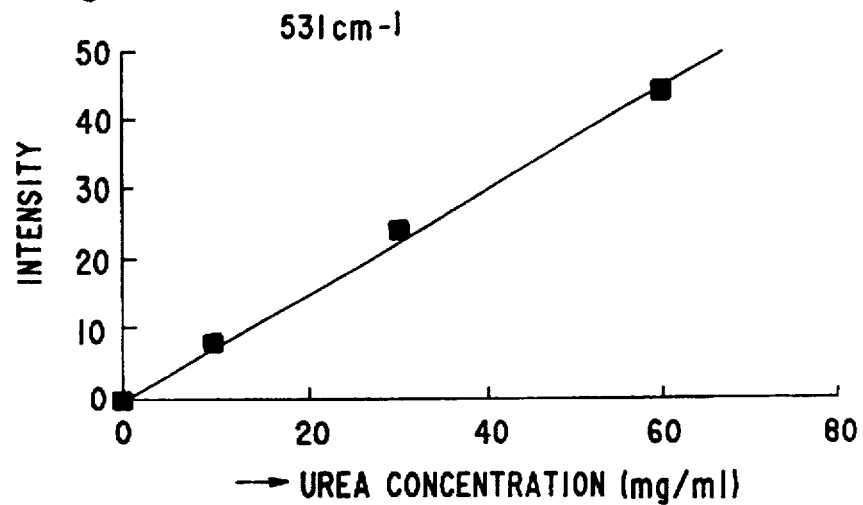
FIG. 30 illustrates the correlation between the urea concentration in urine and Raman scattered light intensity at a wavenumber of 531 cm$^{-1}$.
Figure 31:
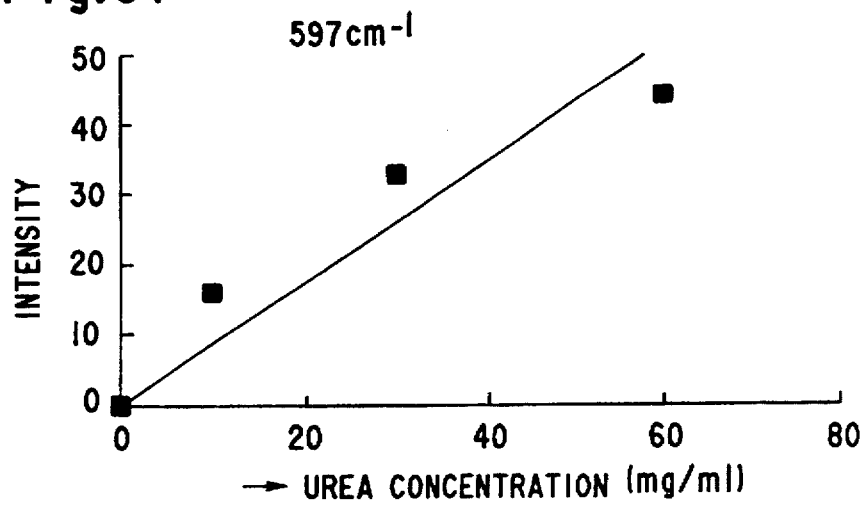
FIG. 31 illustrates the correlation between the urea concentration in urine and Raman scattered light intensity at a wavenumber of 597 cm$^{-1}$.
Figure 32:
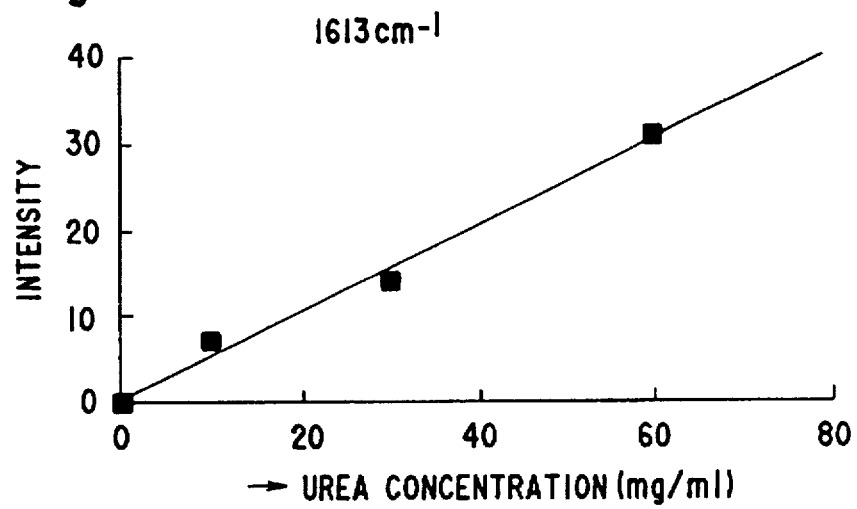
FIG. 32 illustrates the correlation between the urea concentration in urine and Raman scattered light intensity at a wavenumber of 1613 cm$^{-1}$.
Figure 33:
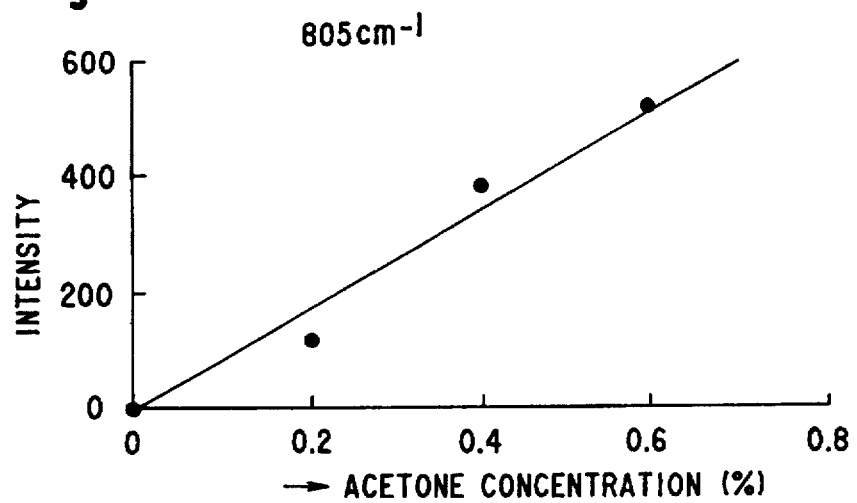
FIG. 33 illustrates the correlation between the acetone concentration in urine and Raman scattered light intensity at a wavenumber of 805 cm$^{-1}$.
Figure 34:
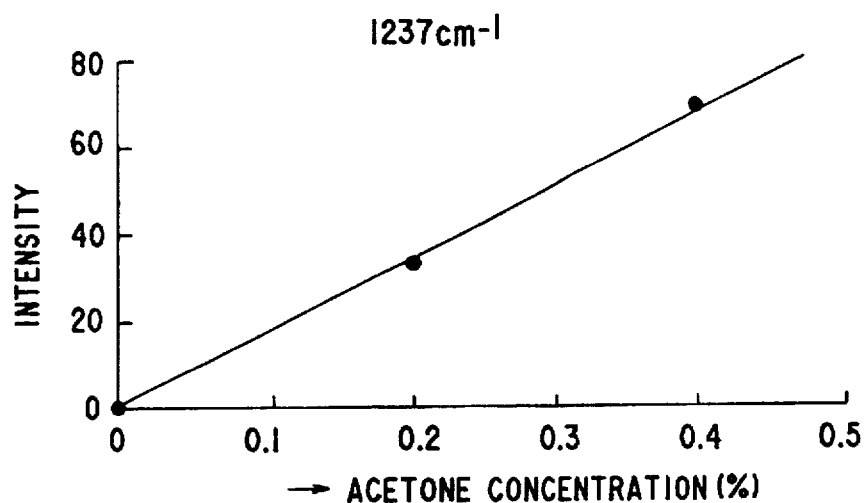
FIG. 34 illustrates the correlation between the acetone concentration in urine and Raman scattered light intensity at a wavenumber of 1237 cm$^{-1}$.
Figure 35:
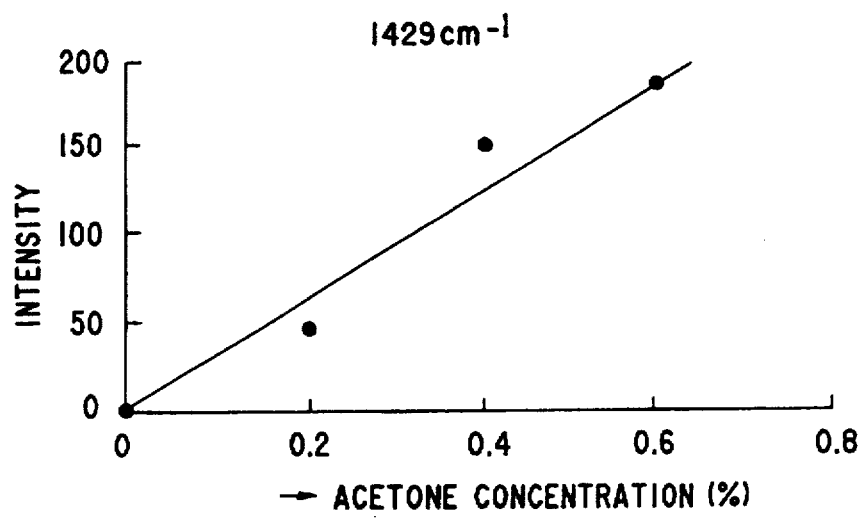
FIG. 35 illustrates the correlation between the acetone concentration in urine and Raman scattered light intensity at a wavenumber of 1429 cm$^{-1}$.
Figure 36:
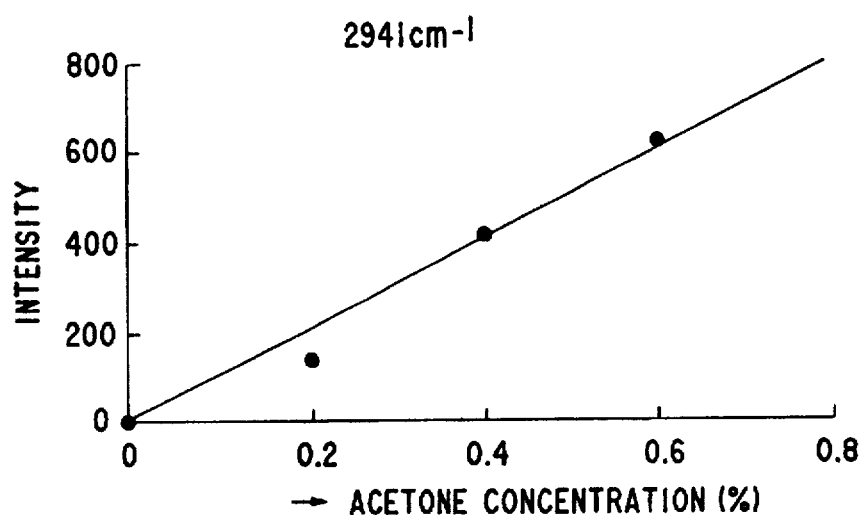
FIG. 36 illustrates the correlation between the acetone concentration in urine and Raman scattered light intensity at a wavenumber of 2941 cm$^{-1}$.

Simultaneous Determination of Intra-Urinary Acetone, Urea and Glucose through Raman Spectroscopy:

FIGS. 24 to 26 show results of measurement made by adding acetone, urea and glucose to a normal urine in different concentrations respectively. FIG. 24 shows the spectrum of a sample prepared by adding acetone to normal urine to be 37.5% (V/V). FIG. 25 shows the spectrum of a sample prepared by adding acetone, urea and glucose to normal urine to be 17% (V/V), 25 mg/ml and 416 µg/ml respectively, and FIG. 26 shows the spectrum of a sample prepared by adding acetone, urea and glucose to be 17% (V/V), 50 mg/ml and 1.17 mg/ml respectively.

FIGS. 27 to 32 show results of correlations between Raman spectral intensity values and concentrations taken at wavenumber positions of 1008 cm$^{-1}$, 1063 cm$^{-1}$, 1168 cm$^{-1}$, 531 cm$^{-1}$, 597 cm$^{-1}$ and 1613 cm$^{-1}$ respectively in relation to urea.

Figure 37:
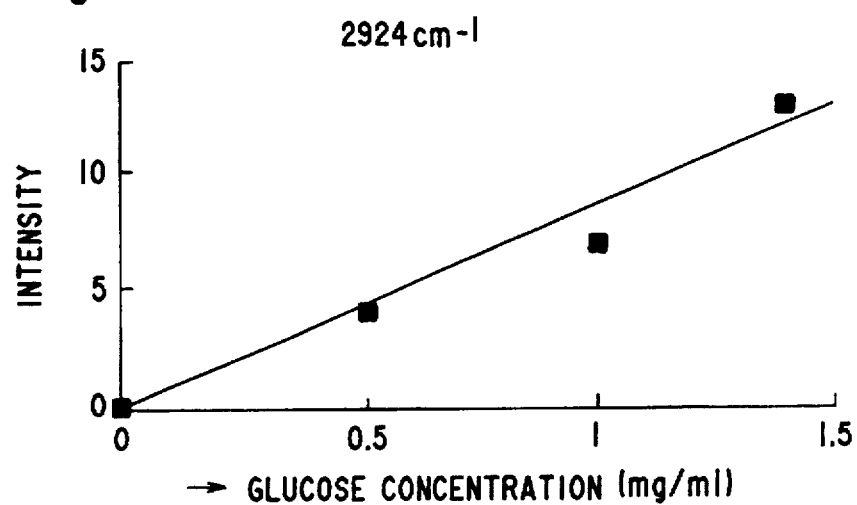
FIG. 37 illustrates the correlation between the glucose concentration in urine and Raman scattered light intensity at a wavenumber of 2924 cm$^{-1}$.

FIGS. 33 to 36 show results of correlations similarly taken at wavenumbers of 805 cm$^{-1}$, 1237 cm$^{-1}$, 1429 cm$^{-1}$ and 2941 cm$^{-1}$ in relation to acetone, and FIG. 37 shows a result of a correlation similarly taken at a wavenumber position of 2924 cm$^{-1}$ in relation to glucose. The correlation coefficients $R^2$ of all these correlations were at least 0.9, to attain excellent results.

(EXAMPLE 10)

Figure 38:
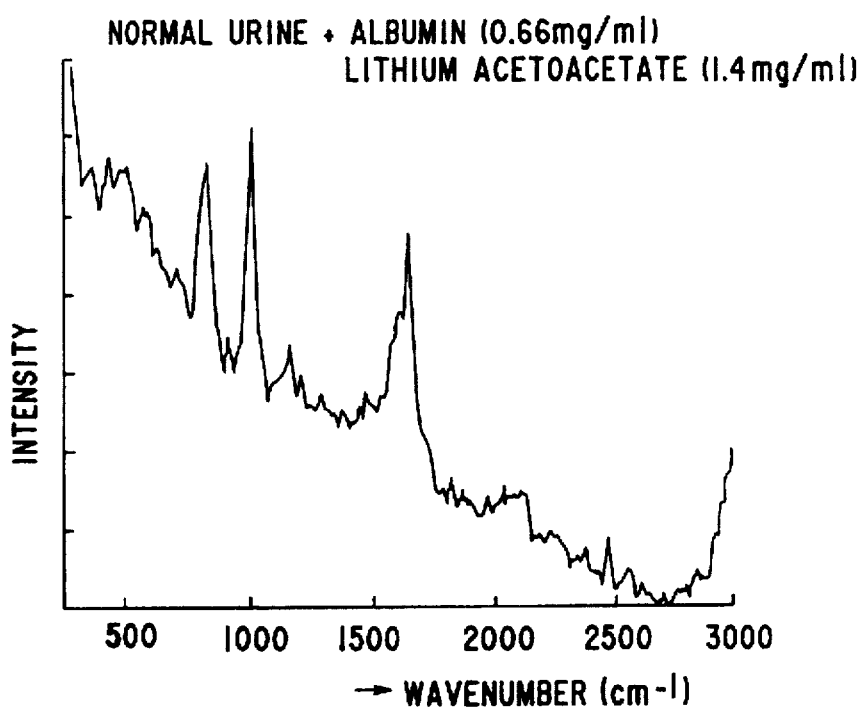
FIG. 38 illustrates the Raman spectrum of a sample prepared by extending the amounts of albumin and lithium acetoacetate in normal urine by about 0.66 mg/ml and about 1.4 mg/ml respectively.
Figure 39:
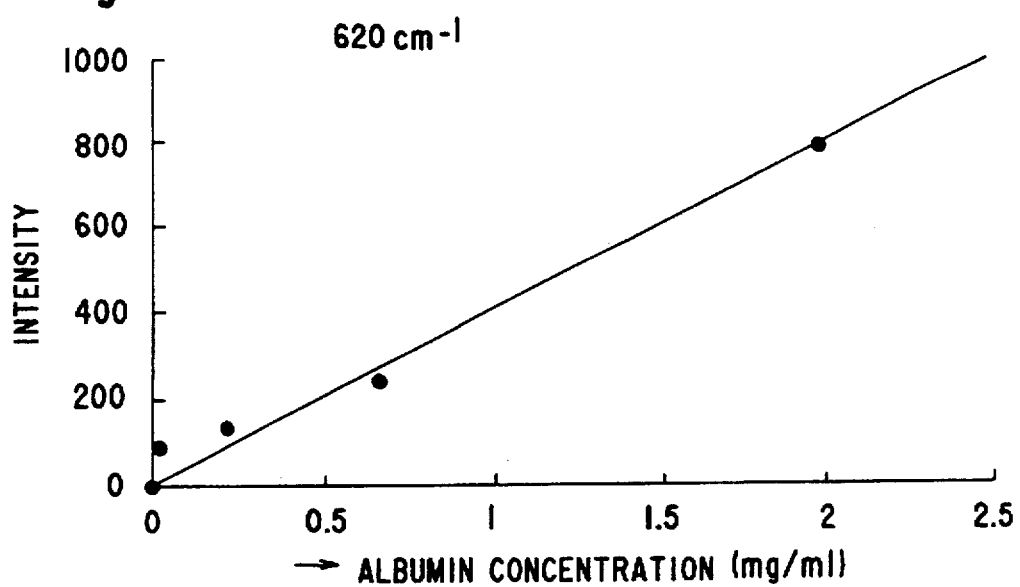
FIG. 39 illustrates the correlation between the albumin concentration in urine and Raman scattered light intensity at a wavenumber of 620 cm$^{-1}$.
Figure 40:
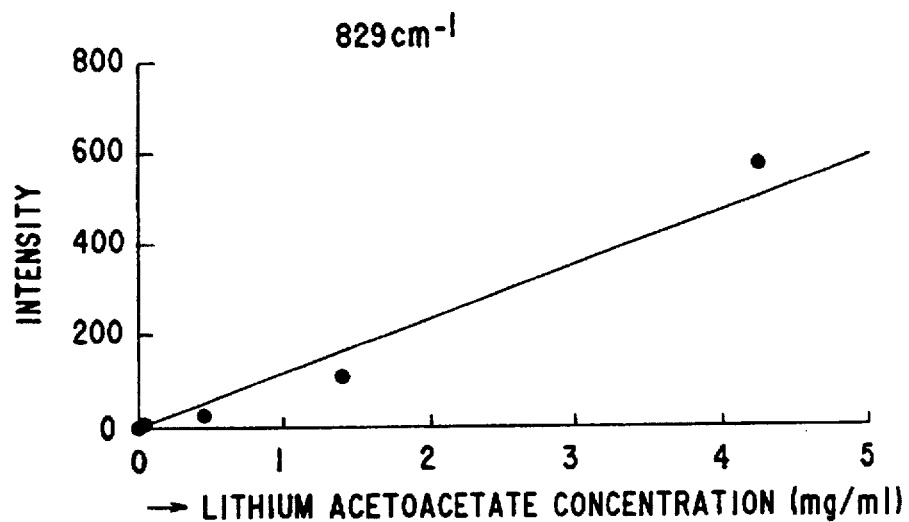
FIG. 40 illustrates the correlation between the lithium acetoacetate concentration in urine and Raman scattered light intensity at a wavenumber of 829 cm$^{-1}$.

Simultaneous Determination of Intra-Urinary Protein and Lithium Acetoacetate through Raman Spectroscopy:

FIGS. 38 to 40 show results of measurement made by adding albumin and lithium acetoacetate to a normal urine in different concentrations respectively. FIG. 38 shows the spectrum of a sample prepared by adding albumin and lithium acetoacetate to be 0.66 mg/ml and 1.4 mg/ml respectively.

FIG. 39 shows a result of investigation on the correlation between intensity of 620 cm$^{-1}$ and concentrations in relation to albumin.

FIG. 40 shows a result of investigation on the correlation between intensity of 829 cm$^{-1}$ and concentrations in relation to lithium acetoacetate. The correlation coefficients $R^2$ of both correlations were at least 0.9, to attain excellent results.

(EXAMPLE 11)

Figure 41:
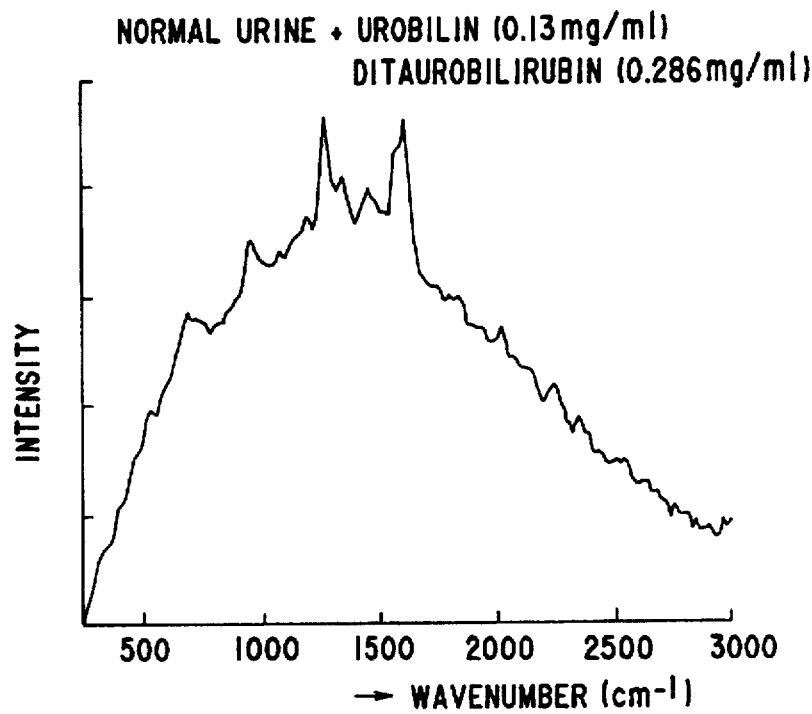
FIG. 41 illustrates the Raman spectrum of a sample prepared by extending the amounts of urobilin and ditaurobilirubin in normal urine by about 0.13 mg/ml and about 0.286 mg/ml respectively.
Figure 42:
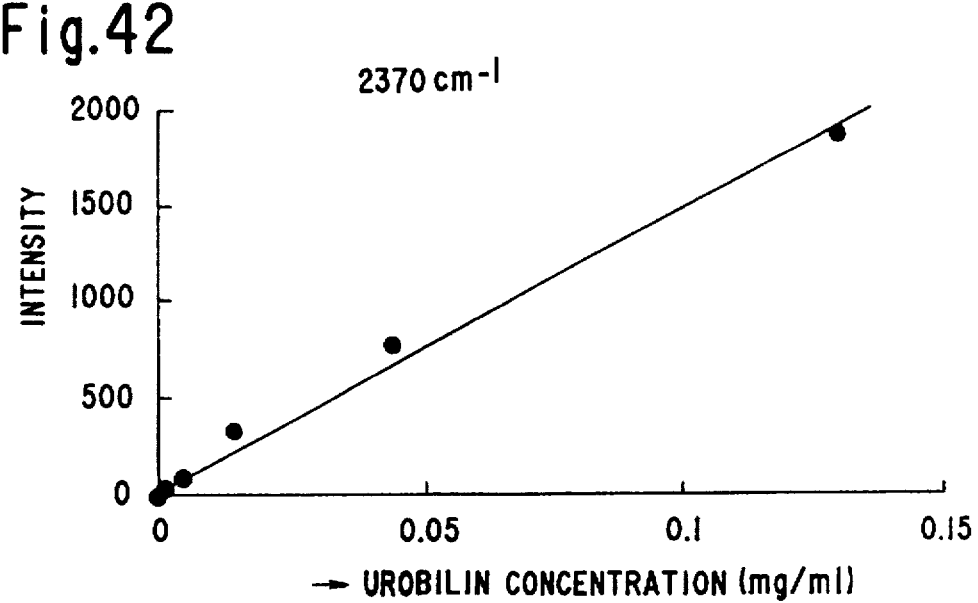
FIG. 42 illustrates the correlation between the urobilin concentration in urine and Raman scattered light intensity at a wavenumber of 2370 cm$^{-1}$.
Figure 43:
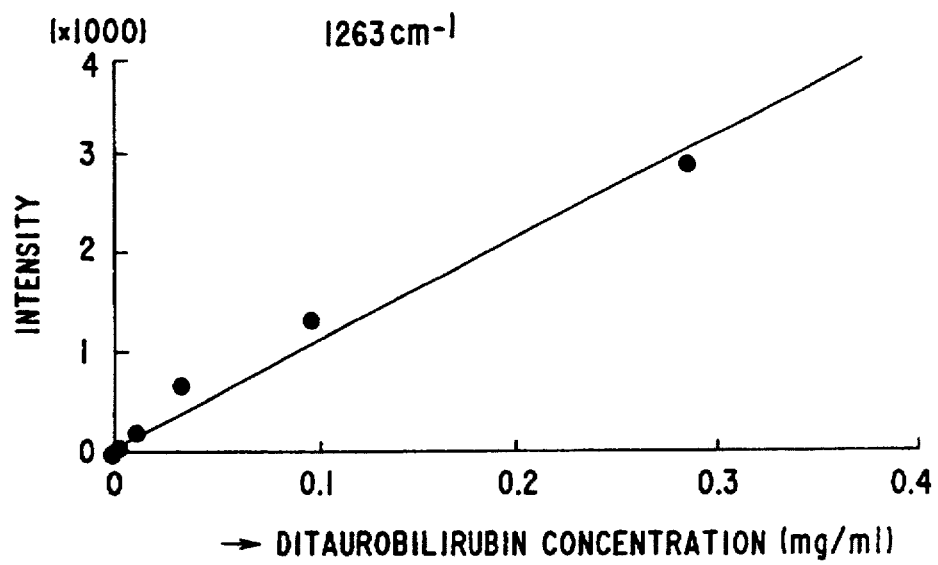
FIG. 43 illustrates the correlation between the ditaurobilirubin concentration in urine and Raman scattered light intensity at a wavenumber of 1263 cm$^{-1}$.
Figure 44:
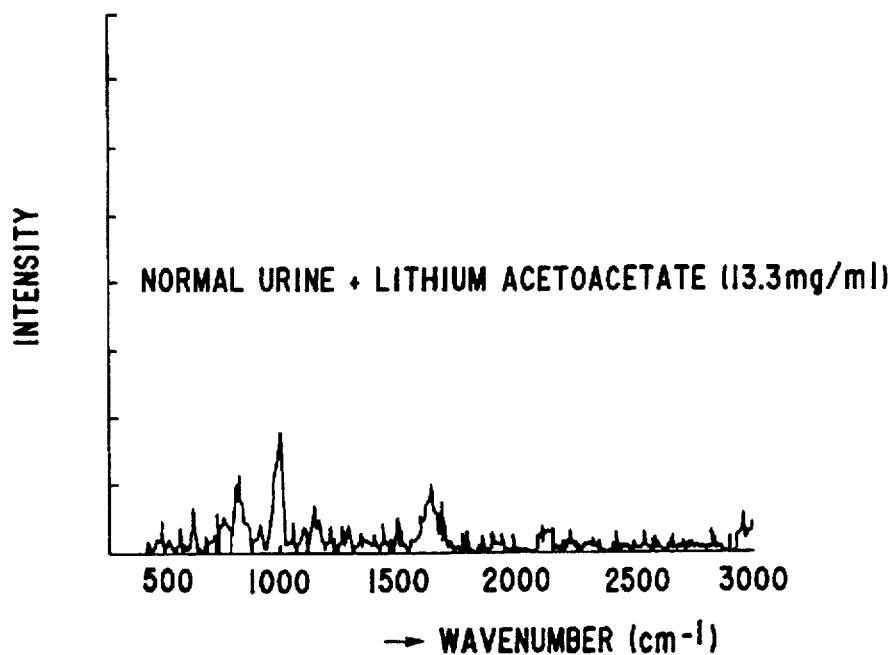
FIG. 44 illustrates the Raman spectrum of a sample prepared by extending the amount of lithium acetoacetate in normal urine by 13.3 mg/ml.
Figure 45:
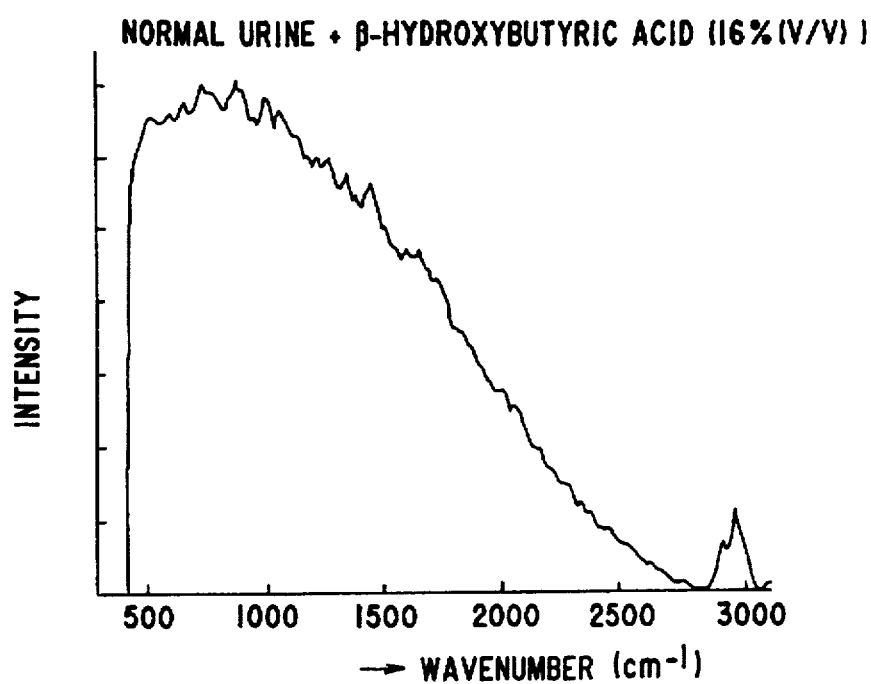
FIG. 45 illustrates the Raman spectrum of a sample prepared by extending the amount of β-hydroxybutyric acid in normal urine to be 16% (V/V)
Figure 46:
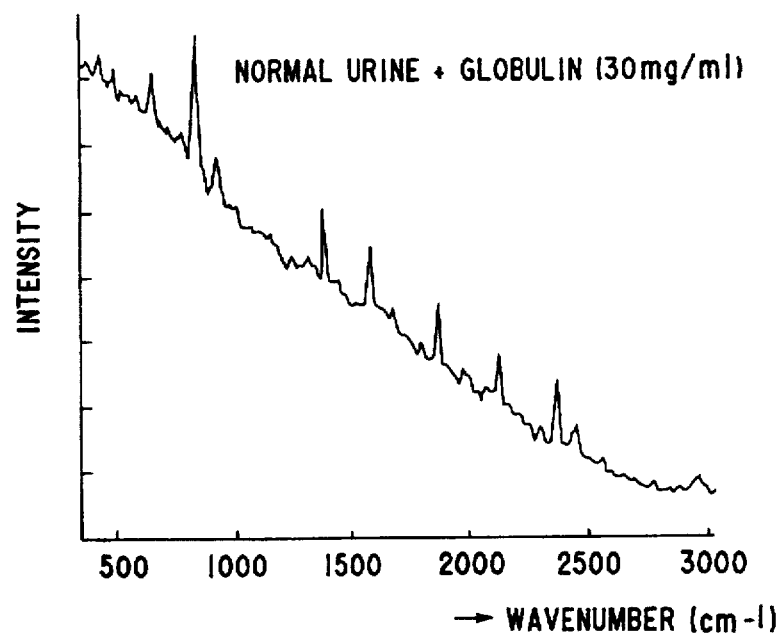
FIG. 46 illustrates the Raman spectrum of a sample prepared by extending the amount of globulin in normal urine by 30 mg/ml.
Figure 47:
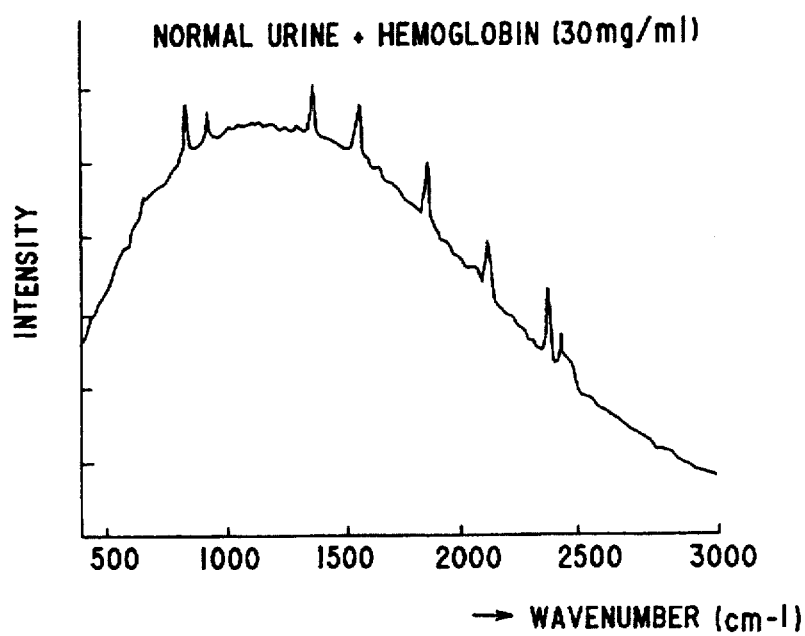
FIG. 47 illustrates the Raman spectrum of a sample prepared by extending the amount of hemoglobin in normal urine by 30 mg/ml.
Figure 48:
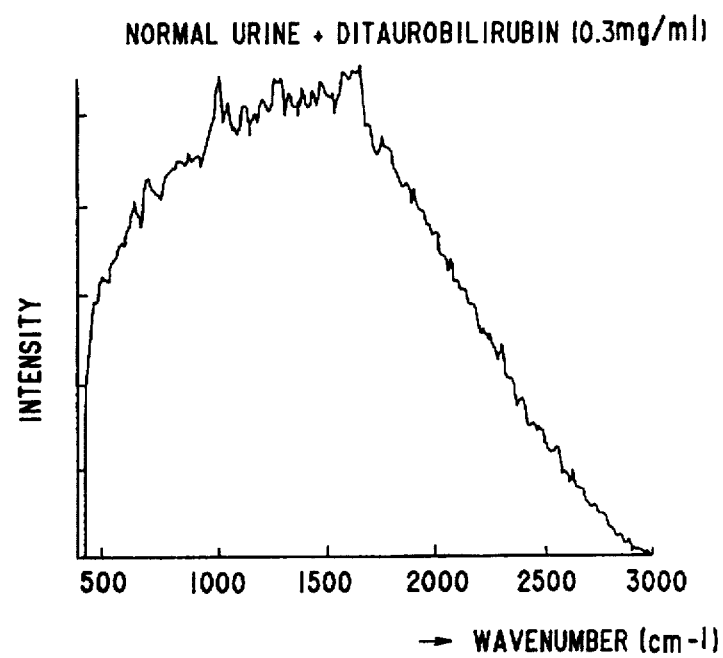
FIG. 48 illustrates the Raman spectrum of a sample prepared by extending the amount of ditaurobilirubin in normal urine by 0.3 mg/ml.
Figure 49:
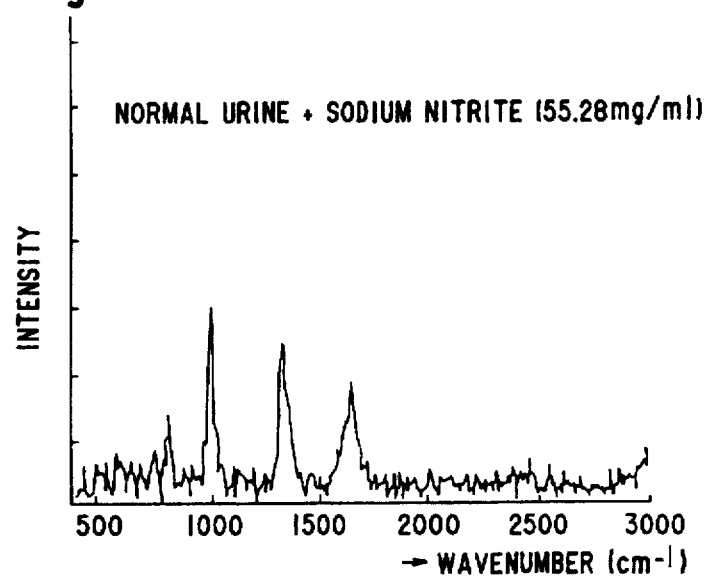
FIG. 49 illustrates the Raman spectrum of a sample prepared by extending the amount of sodium nitrite in normal urine by 55.28 mg/ml.
Figure 50:
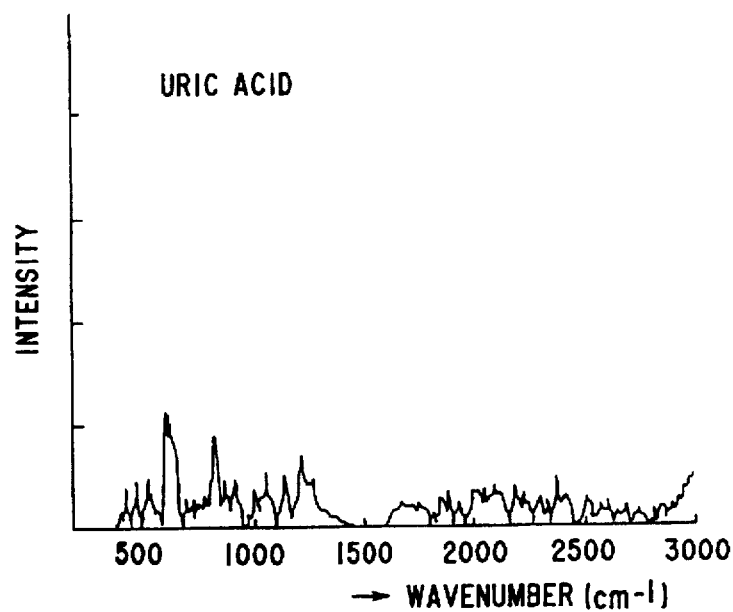
FIG. 50 illustrates the Raman spectrum of a sample prepared by extending the amount of uric acid in distilled water by a saturation amount.
Figure 51:
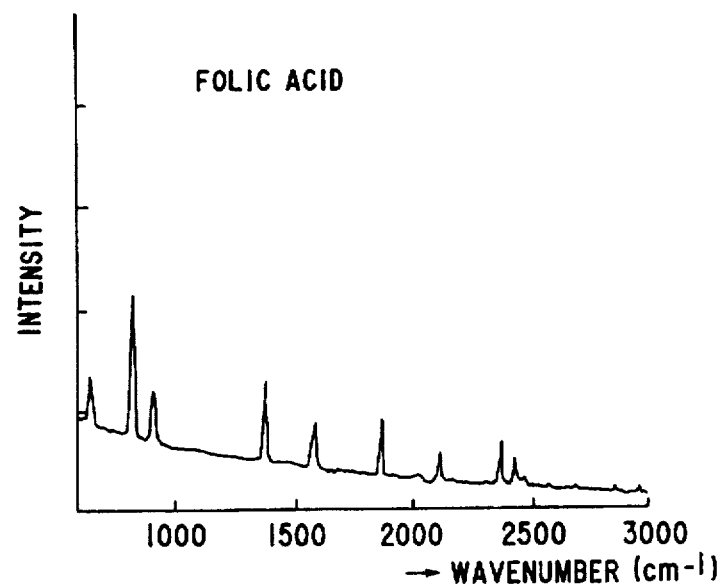
FIG. 51 illustrates the Raman spectrum of a sample prepared by extending the amount of folic acid in distilled water by a saturation amount.
Figure 52:
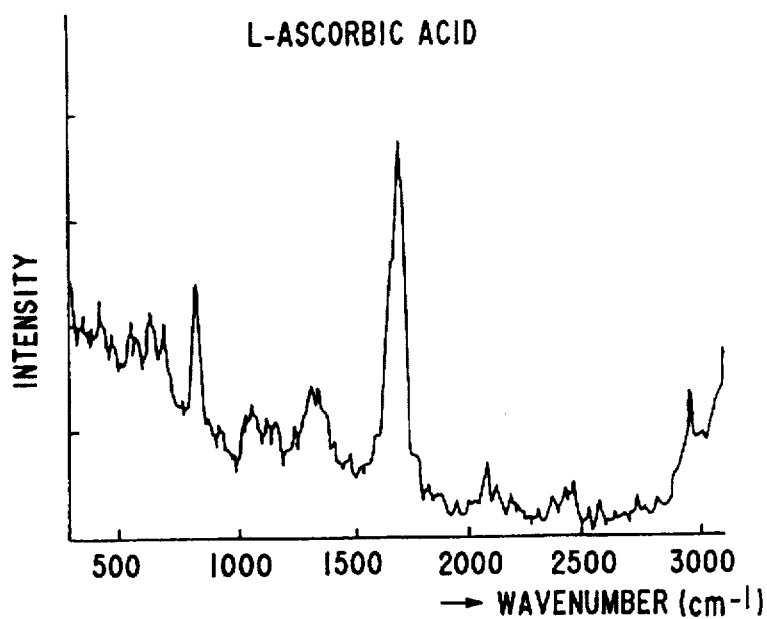
FIG. 52 illustrates the Raman spectrum of a sample prepared by extending the amount of L-ascorbic acid in distilled water by a saturation amount.
Figure 53:
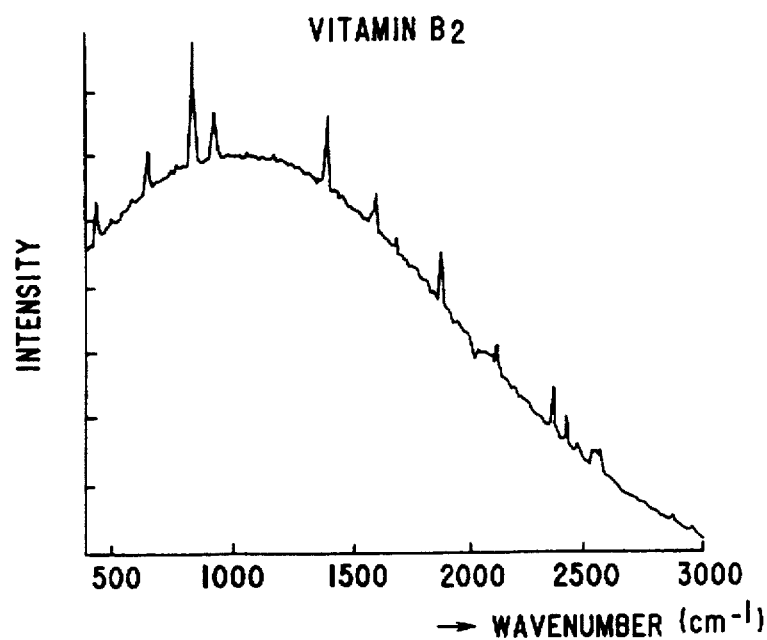
FIG. 53 illustrates the Raman spectrum of a sample prepared by extending the amount of vitamin $B_2$ in distilled water by a saturation amount.
Figure 54:
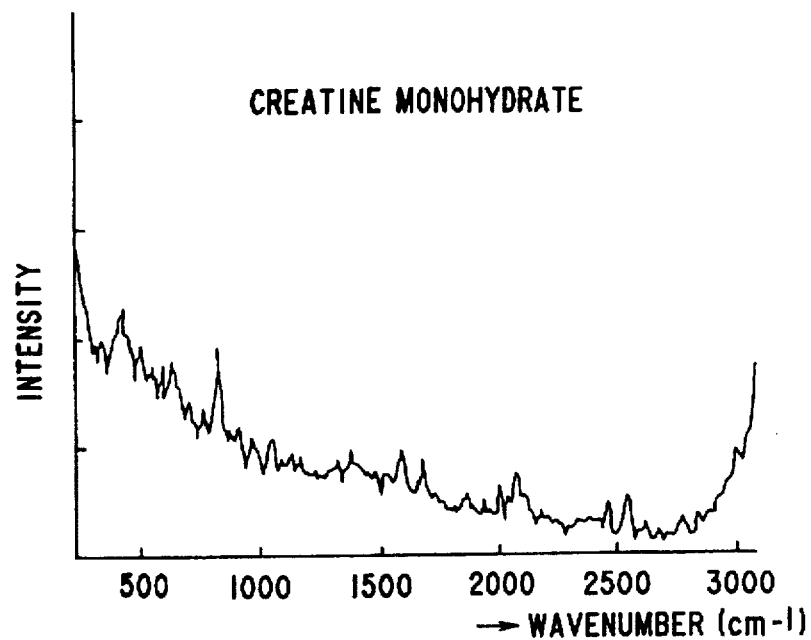
FIG. 54 illustrates the Raman spectrum of a sample prepared by extending the amount of creatine monohydrate in distilled water by a saturation amount.
Figure 55:
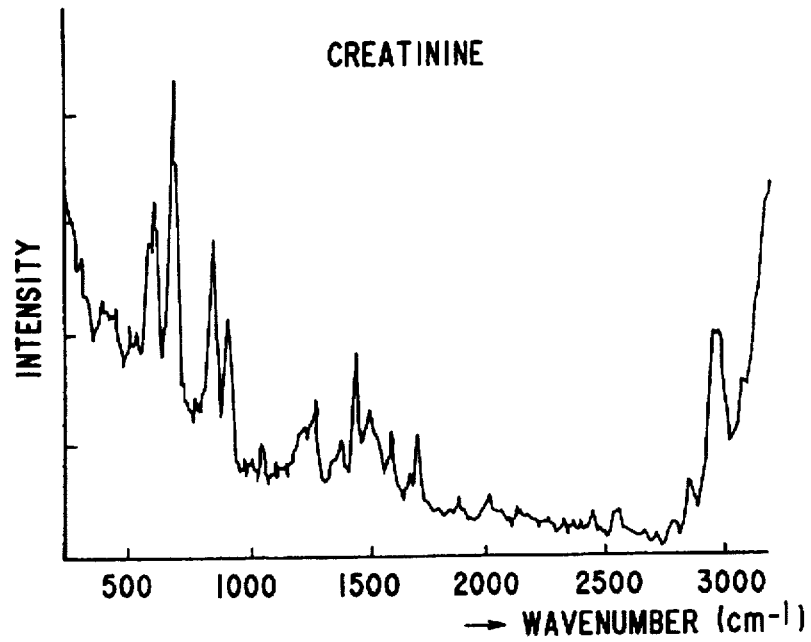
FIG. 55 illustrates the Raman spectrum of a sample prepared by extending the amount of creatinine in distilled water by a saturation amount.
Figure 56:
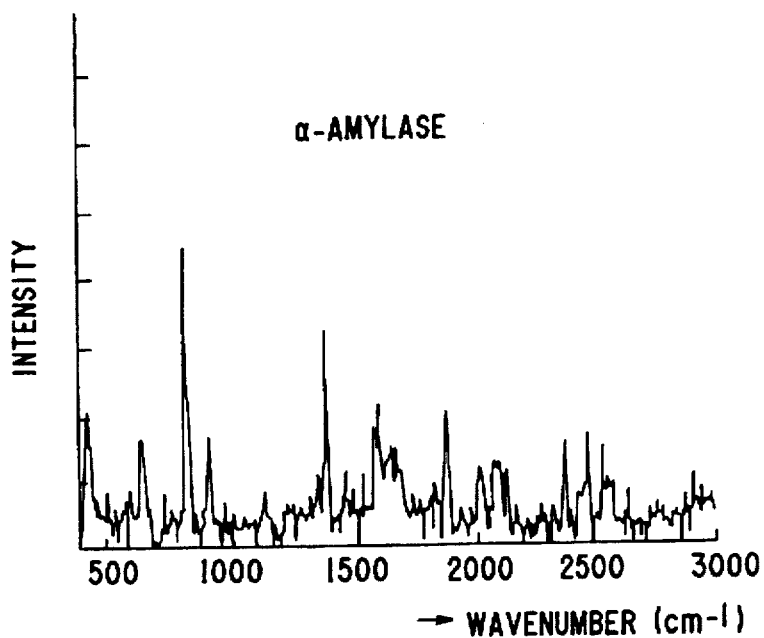
FIG. 56 illustrates the Raman spectrum of a sample prepared by extending the amount of α-amylase in distilled water by a saturation amount.
Figure 57:
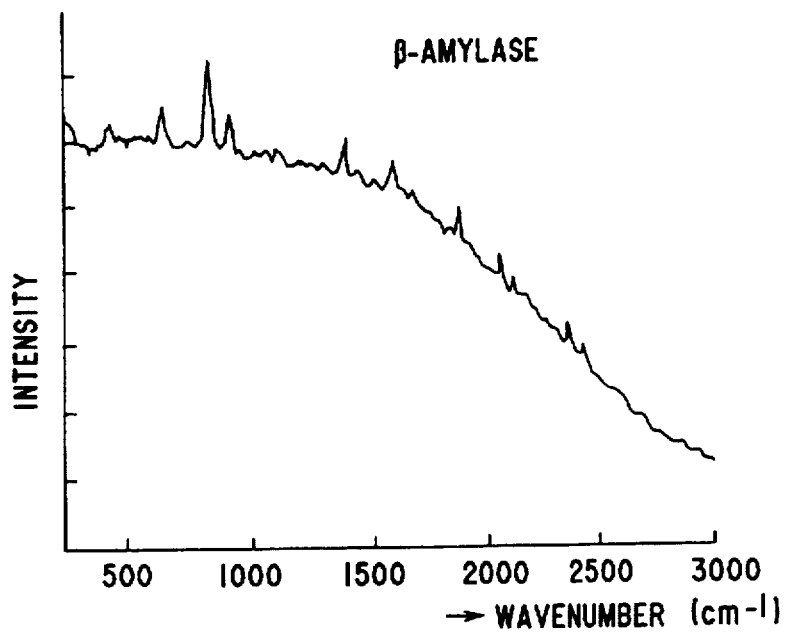
FIG. 57 illustrates the Raman spectrum of a sample prepared by extending the amount of β-amylase in distilled water by a saturation amount.
Figure 58:
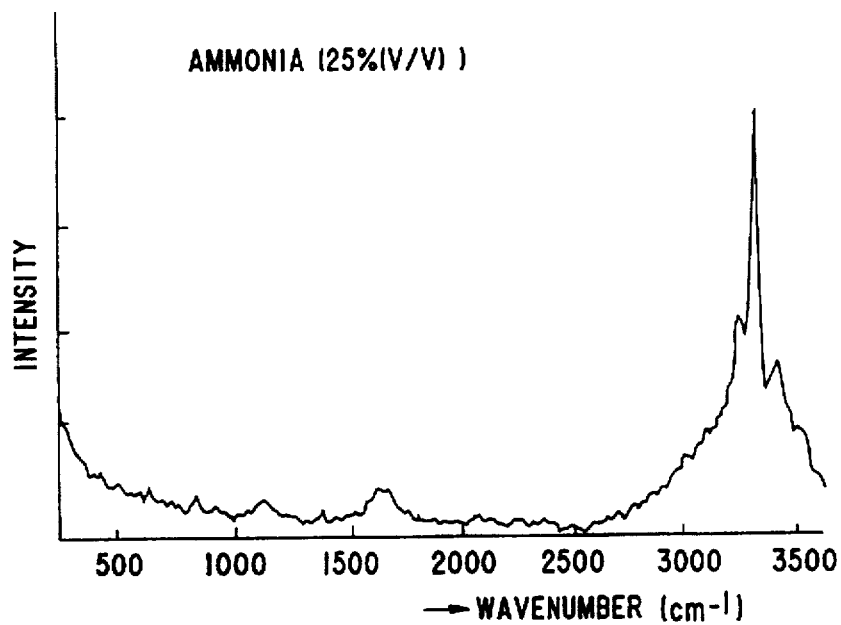
FIG. 58 illustrates the Raman spectrum of a sample prepared by extending the amount of ammonia in distilled water to be 25% (V/V)
Figure 59:
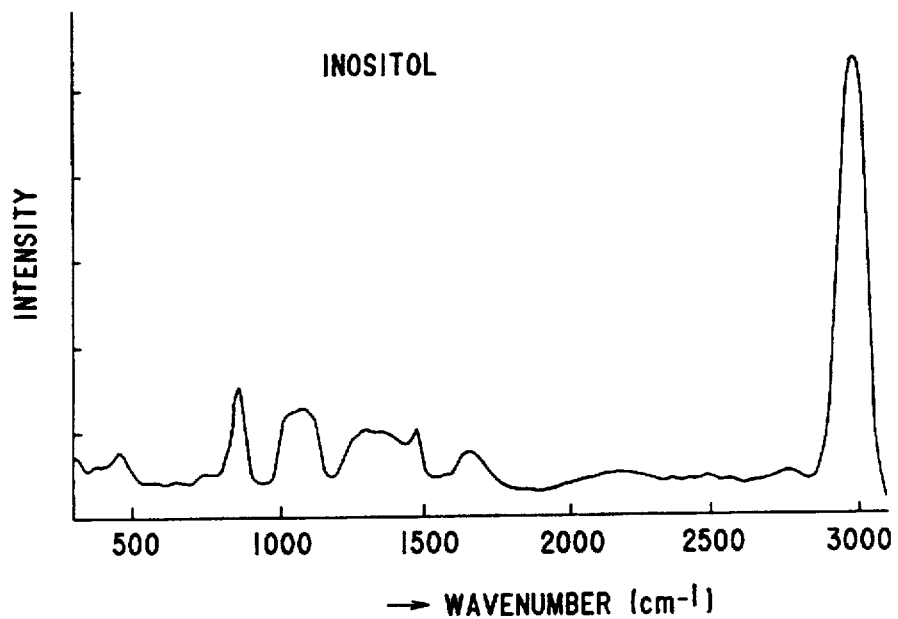
FIG. 59 illustrates the Raman spectrum of a sample prepared by extending the amount of inositol in distilled water by a saturation amount.
Figure 60:
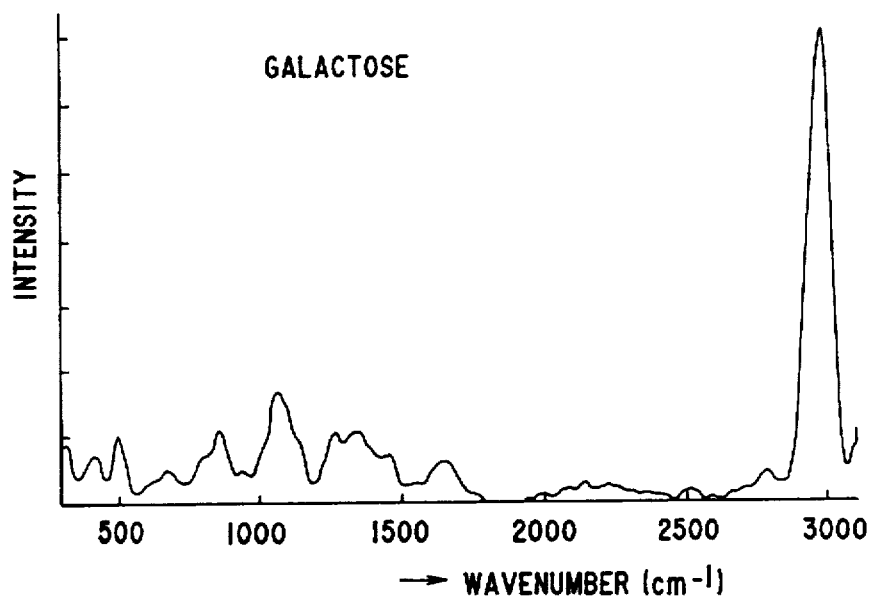
FIG. 60 illustrates the Raman spectrum of a sample prepared by extending the amount of galactose in distilled water by a saturation amount.
Figure 61:
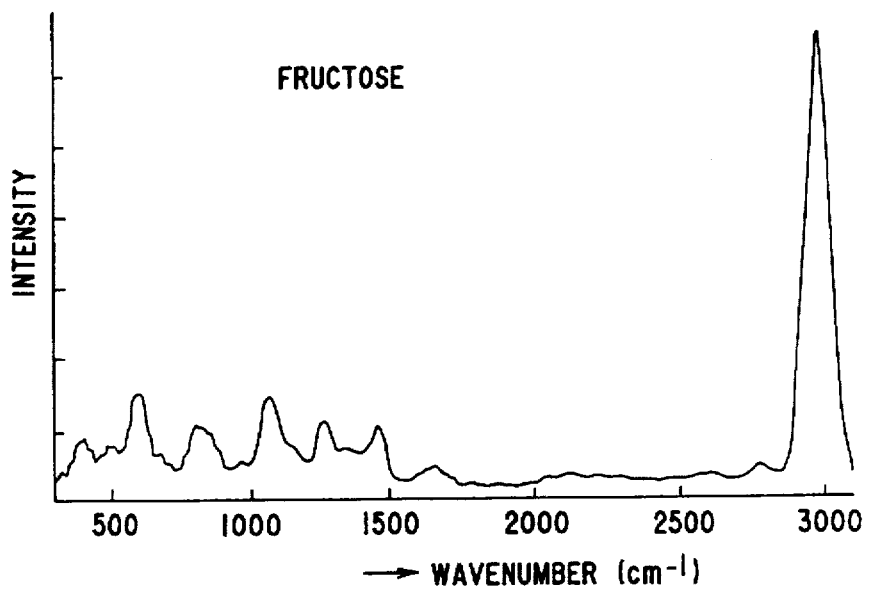
FIG. 61 illustrates the Raman spectrum of a sample prepared by extending the amount of fructose in distilled water by a saturation amount.

Simultaneous Determination of Intra-Urinary Urobilin and Ditaurobilirubin through Raman Spectroscopy:

FIGS. 41 to 43 show results of measurement made by adding urobilin and ditaurobilirubin to a normal urine in different concentrations respectively. FIG. 41 shows the spectrum of a sample prepared by adding urobilin and ditaurobilirubin to be 0.13 mg/ml and 0.286 mg/ml respectively.

FIG. 42 shows a result of investigation on the correlation between intensity of 2370 cm$^{-1}$ and concentrations in relation to urobilin. FIG. 43 shows a result of investigation on the correlation between intensity of 1263 cm$^{-1}$ and concentrations in relation to ditaurobilirubin. The correlation coefficients $R^2$ of both correlations were at least 0.9, to attain excellent results.

(EXAMPLE 12)

Detection of Intra-Urinary Components through Raman Spectroscopy:

FIGS. 44 to 49 show results of measurement made by adding 13.3 mg/ml of lithium acetoacetate, 16% (V/V) of β-hydroxybutyric acid, 30 mg/ml of globulin, 30 mg/ml of hemoglobin, 0.3 mg/ml of ditaurobilirubin and 55.28 mg/ml of sodium nitrite to normal urine respectively.

It is possible to confirm presence/absence by confirming intensity changes of arbitrary peaks. In lithium acetoacetate shown in FIG. 44, for example, a Raman peak, which has been impossible to obtain in the spectrum of normal urine, appears at 829 cm$^{-1}$. Thus, presence of lithium acetoacetate can be confirmed. When it is confirmed that peaks of 1630 cm$^{-1}$, 852 cm$^{-1}$ in particular, 1592 cm$^{-1}$, 1616 cm$^{-1}$ and 813 cm$^{-1}$ appear for β-hydroxybutyric acid of FIG. 45, globulin of FIG. 46, hemoglobin of FIG. 47, ditaurobilirubin of FIG. 48 and sodium nitrite of FIG. 49 respectively, presence/absence thereof can be confirmed.

(EXAMPLE 13)

Detection of Body Fluid Components through Raman Spectroscopy:

FIGS. 50 to 61 show results of measurement made by adding uric acid, folic acid, L-ascorbic acid, vitamin B$_2$, creatine monohydrate, creatinine, α-amylase and β-amylase to distilled water by saturation amounts, adding ammonia by 25% (V/V) and adding inositol, galactose and fructose to be saturation amounts respectively.

Similarly to Example 12, presence/absence can be confirmed by confirming intensity changes of arbitrary peaks. It is possible to confirm presence/absence by confirming that peaks of 670 $cm^{-1}$, 661 $cm^{-1}$, 1703 $cm^{-1}$, 890 $cm^{-1}$, 830 $cm^{-1}$, 695 $cm^{-1}$, 1864 $cm^{-1}$, 893 $cm^{-1}$, 3407 $cm^{-1}$, 443 $cm^{-1}$, 495 $cm^{-1}$ and 599 $cm^{-1}$ appear for uric acid of FIG. 50, for folic acid of FIG. 51, for ascorbic acid of FIG. 52, for vitamin $B_2$ of FIG. 53, for creatine monohydrate of FIG. 54, for creatinine of FIG. 55, for α-amylase of FIG. 56, for β-amylase of FIG. 57, for ammonia of FIG. 58, for inositol of FIG. 59, for galactose of FIG. 60 and for fructose of FIG. 61 respectively.

FIG. 62 is a Table showing measured wavenumbers of the respective components. It is possible to avoid superposition and mixing of peaks by selecting wavenumber positions enclosed with broken lines. Around 2370 $cm^{-1}$ may be selected in case of measuring the total protein amount, while around 2940 $cm^{-1}$ may be selected in case of measuring a total ketone body.

Correlation coefficients obtained as to some types of target substances are shown in Table 1. From the result of the correlation coefficients, the accuracy of the present invention can be confirmed.

TABLE 1

| COMPONENT | CORRELATION COEFFICIENT |
|---|---|
| albumin | 0.999 |
| globulin | 0.994 |
| hemoglobin | 0.986 |
| glucose | 0.964 |
| lithium acetoacetate | 0.998 |
| β-hydroxybutyric acid | 0.997 |
| acetone | 0.999 |
| ditaurobilirubin | 0.994 |
| urobilin | 0.994 |
| sodium nitrite | 0.998 |
| urea | 0.998 |

Measurement can be made in higher accuracy by employing an analytical technique such as multivariate regression analysis.

(EXAMPLE 14)

Simultaneous Measurement of Plural Intra-Urinary Components through Multivariate Regression Analysis:

150 mg/dl, 300 mg/dl and 450 mg/dl of urine, 600 mg/dl, 1.2 g/dl and 1.8 g/dl of sodium nitrite and 300 mg/dl, 600 mg/dl and 900 mg/dl of acetone were added to normal urine in arbitrary combinations respectively for making spectral measurement, thereby determining concentrations through multivariate regression analysis.

The concentration C of an arbitrary substance which is present in urine can be approximated in the following equation:

$$C = \sum_{i=1}^{n} k(\lambda i) \cdot A(\lambda i)$$

where k (λi) represents the proportional constant at a wavenumber λi, and A (λi) represents Raman light intensity at the wavenumber λi.

The proportional constant k (λi) is decided in the procedure of multivariate regression analysis so that the correlation between the concentration of a sample having a known analytical value and an estimated concentration is maximized. This calculation is previously integrated into commercially available processing software and automatically carried out, so that this equation is formed every intra-urinary substance whose concentration is to be obtained.

Figure 1:
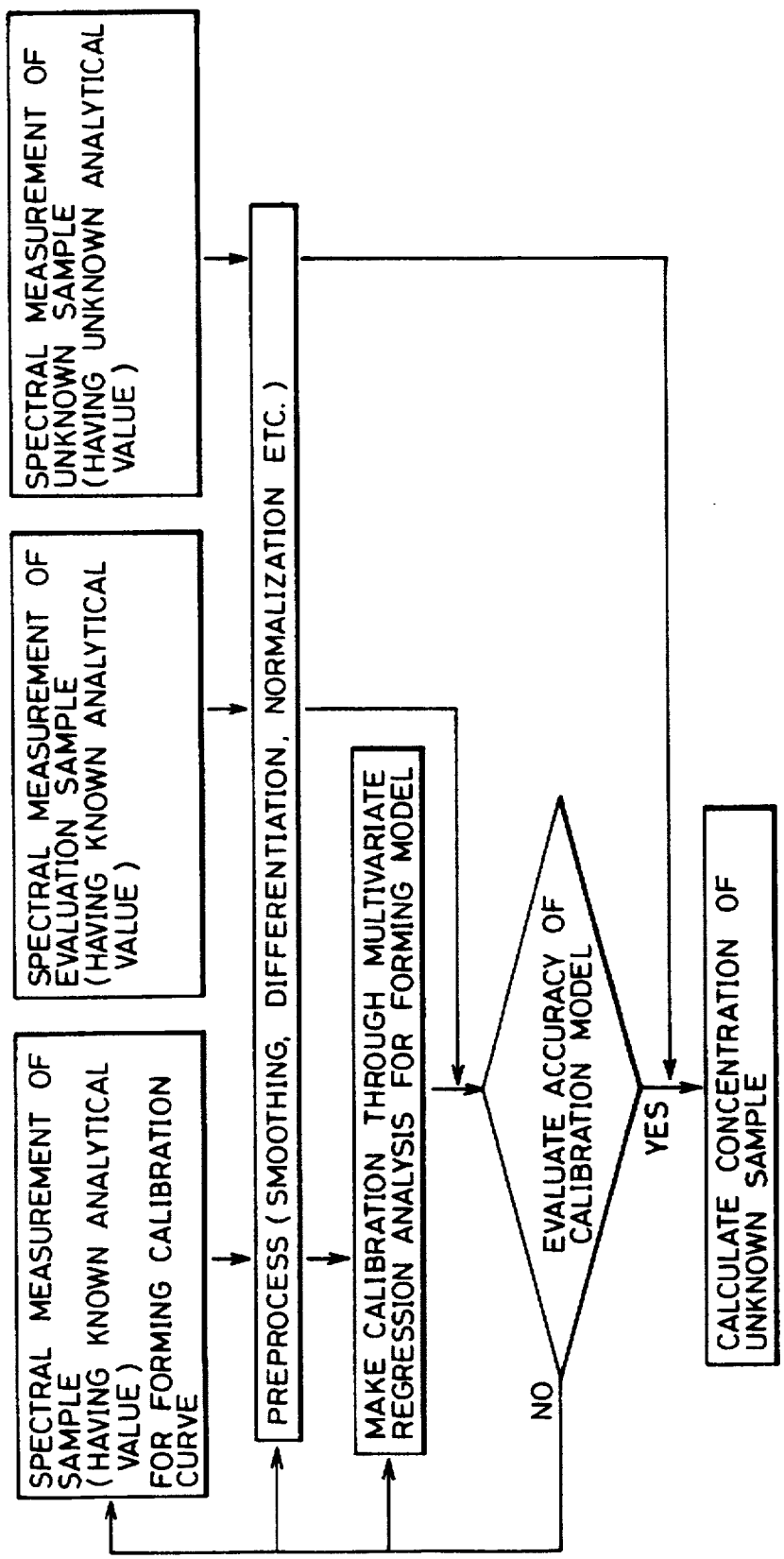
FIG. 1 is a flow chart showing steps from spectrum measurement to concentration determination with application of multivariate regression analysis.

Processes from spectral measurement to concentration determination were carried out along the flow chart of FIG. 1. In this example, no preprocess was made and QUANT+ by Perkin Elmer Co., Ltd. was employed as processing software. The PCR method was employed as the processing method. When full cross validation is performed, evaluation of accuracy of a calibration model can be omitted.

FIG. 63 shows correlation diagrams of calculated values and measured values (reference values) obtained in this Example. The correlation coefficients $R^2$ and predictive standard deviations (SEP) were 0.986 and 18.13 as to urea, 0.992 and 57.17 as to sodium nitrite, and 0.956 and 69.74 as to acetone respectively. The predictive standard deviation SEP is calculated as follows:

$$SEP = \sqrt{\sum_{i=1}^{n} (di - D)^2/(n-1)^2}$$

where di represents the difference between a calculated value by a calibration model and a measured value, D represents an average value of di, and n represents the number of evaluation samples.

It means that accuracy of a calibration model is increased as SEP is reduced.

Although the present invention has been described and illustrated in detail, it is clearly understood that the same is by way of illustration and example only and is not to be taken by way of limitation, the spirit and scope of the present invention being limited only by the terms of the appended claims.

We claim:

1. A measuring method comprising the steps of:

for a plurality of components of a body fluid to be measured, previously selecting a wavenumber having an excellent correlation between the concentration of a component and light scattering spectral intensity as a measuring wavenumber which is specific to said component;

irradiating a body fluid sample with excitation light for measuring light scattering spectral intensity at each said measuring wavenumber as to said each component to be measured or light scattering spectral cumulative intensity in each measuring wavenumber range; and simultaneously qualitatively/quantitatively analyzing respective said components in said body fluid through a calibration curve being previously prepared as to said light scattering spectral intensity at each said measuring wavenumber or said light scattering spectral cumulative intensity in said each measuring wavenumber range and the concentration of said component.

2. The measuring method in accordance with claim 1, wherein a plurality of components in said body fluid sample are simultaneously qualitatively/quantitatively analyzed by multivariate regression analysis.

3. In the measuring method in accordance with claim 1, wherein said wavenumber having an excellent correlation between the concentration of said each component and said light scattering spectral intensity has a correlation coefficient R of at least 0.8.

said correlation coefficient R being calculated as follows:

$$R = \frac{\sum_{i=1}^{n}\{(xi-X)(yi-Y)\}}{\sqrt{\left[\sum_{i=1}^{n}(xi-X)^2\right]\left[\sum_{i=1}^{n}(yi-Y)^2\right]}}$$

where xi represents the concentration of each point of said component in said body fluid, yi represents Raman scattering spectral intensity with respect to xi, X represents an average value of the concentration of each point of said component in said body fluid, and Y represents an average value of said Raman scattering spectral intensity.

4. The measuring method in accordance with claim 3, wherein the correlation coefficient R is at least 0.9.

5. In the measuring method in accordance with claim 1, wherein at least one of albumin, globulin, hemoglobin, glucose, lithium acetoacetate, β-hydroxybutyric acid, acetone, ditaurobilirubin, urobilin, sodium nitrite, urea, uric acid, folic acid, ascorbic acid, vitamin $B_2$, creatine monohydrate, creatinine, α-amylase, β-amylase and ammonia is contained as a body fluid component to be measured, measuring wavenumbers or measuring wavenumber ranges for respective said components being selected from around 590 to 650 $cm^{-1}$, around 800 to 860 $cm^{-1}$, and around 2342 to 2402 $cm^{-1}$ for albumin, selected from around 158 to 218 $cm^{-1}$, around 402 to 462 $cm^{-1}$, around 623 to 683 $cm^{-1}$, around 807 to 867 $cm^{-1}$, around 822 to 862 $cm^{-1}$, around 1353 to 1413 $cm^1$, around 1562 to 1622 $cm^{-1}$, around 1847 to 1907 $cm^{-1}$, around 2095 to 2155 $cm^{-1}$, around 2340 to 2400 $cm^{-1}$ and around 2403 to 2463 $cm^{-1}$ for globulin, selected from around 807 to 867 $cm^{-1}$, around 893 to 953 $cm^{-1}$, around 1353 to 1413 $cm^{-1}$, around 1562 to 1622 $cm^{-1}$, around 1840 to 1900 $cm^{-1}$, around 2095 to 2155 $cm^{-1}$, around 2340 to 2400 $cm^{-1}$, and around 2403 to 2463 $cm^{-1}$ for hemoglobin, selected from around 200 to 554 $cm^{-1}$, around 810 to 944 $cm^{-1}$, and around 2590 to 2940 $cm^{-1}$ for glucose, selected from around 799 to 859 $cm^{-1}$, around 1353 to 1413 $cm^{-1}$, around 1840 to 1900 $cm^{-1}$, around 2347 to 2407 $cm^{-1}$, and around 2907 to 2967 $cm^{-1}$ for lithium acetoacetate, selected from around 1420 to 1480 $cm^{-1}$, around 1557 to 1617 $cm^{-1}$, around 1600 to 1660 $cm^{-1}$, and around 2870 to 2971 $cm^{-1}$ for β-hydroxybutyric acid, selected from around 775 to 845 $cm^{-1}$, around 1050 to 1110 $cm^{-1}$, around 1207 to 1267 $cm^{-1}$, around 1399 to 1459 $cm^{-1}$, 1680 to 1740 $cm^{-1}$, and around 2911 to 2971 $cm^{-1}$ for acetone, selected from around 927 to 987 $cm^{-1}$, around 1233 to 1293 $cm^{-1}$, and around 1586 to 1616 $cm^{-1}$ for ditaurobilirubin, selected as an arbitrary position from 332 to 2900 $cm^{-1}$ for urobilin, selected from around 783 to 843 $cm^{-1}$, and around 1318 to 1378 $cm^{-1}$ for sodium nitrite, selected from around 501 to 561 $cm^{-1}$, around 567 to 627 $cm^{-1}$, around 978 to 1048 $cm^{-1}$, around 1033 to 1093 $cm^{-1}$, around 1138 to 1198 $cm^{-1}$, and around 1583 to 1643 $cm^{-1}$ for urea, selected from around 640 to 700 $cm^{-1}$ for uric acid, selected from around 631 to 691 $cm^{-1}$, around 816 to 876 $cm^{-1}$, around 901 to 961 $cm^{-1}$, around 1355 to 1415 $cm^{-1}$, around 1562 to 1622 $cm^{-1}$, around 1847 to 1907 $cm^{-1}$, around 2093 to 2153 $cm^{-1}$, around 2339 to 2399 $cm^{-1}$, and around 400 to 2460 $cm^{-1}$ for folic acid, selected from around 800 to 860 $cm^{-1}$, around 1673 to 1733 $cm^{-1}$, and around 2919 to 2979 $cm^{-1}$ for ascorbic acid, selected from around 404 to 464 $cm^{-1}$, around 626 to 686 $cm^{-1}$, around 798 to 858 $cm^{-1}$, around 860 to 920 $cm^{-1}$, around 1317 to 1377 $cm^{-1}$, around 1546 to 1606 $cm^{-1}$, around 1834 to 1894 $cm^{-1}$, around 2106 to 2166 $cm^{-1}$, around 2360 to 2420 $cm^{-1}$, and around 2419 to 2479 $cm^{-1}$ for vitamin $B_2$, selected from around 800 to 860 $cm^{-1}$, and around 1563 to 1623 $cm^{-1}$ for creatine monohydrate, selected from around 538 to 598 $cm^{-1}$, 580 to 640 $cm^{-1}$, around 665 to 725 $cm^{-1}$, around 817 to 877 $cm^{-1}$, around 868 to 928 $cm^{-1}$, around 1021 to 1081 $cm^{-1}$, around 1550 to 1610 $cm^{-1}$, around 2868 to 2900 $cm^{-1}$, around 2900 to 2950 $cm^{-1}$, and around 2950 to 2996 $cm^{-1}$ for creatinine, selected from around 393 to 453 $cm^{-1}$, around 631 to 691 $cm^{-1}$, around 792 to 852 $cm^{-1}$, around 868 to 928 $cm^{-1}$, around 1333 to 1393 $cm^{-1}$, around 1546 to 1606 $cm^{-1}$, around 1834 to 1894 $cm^{-1}$, and around 2334 to 2394 $cm^{-1}$ for β-amylase, selected from around 376 to 436 $cm^{-1}$, around 622 to 682 $cm^{-1}$, around 783 to 843 $cm^{-1}$, around 868 to 928 $cm^{-1}$, around 1334 to 1394 $cm^{-1}$, around 1546 to 1606 $cm^{-1}$, around 1834 to 1894 $cm^{-1}$, and around 2665 to 2725 $cm^{-1}$ for β-amylase, selected from around 3190 to 3250 $cm^{-1}$, around 3292 to 3350 $cm^{-1}$, and 3377 to 3437 $cm^{-1}$ for ammonia, selected from around 404 to 464 $cm^{-1}$, around 805 to 865 $cm^{-1}$, around 1014 to 1074 $cm^{-1}$, around 1438 to 1498 $cm^{-1}$, and around 2966 to 3026 $cm^{-1}$ for inositol, selected from around 466 to 526 $cm^{-1}$, 835 to 895 $cm^{-1}$, around 1032 to 1092 $cm^{-1}$, 1237 to 1297 $cm^{-1}$, around 1332 to 1392 $cm^{-1}$, around 1438 to 1498 $cm^{-1}$, and around 2946 to 3006 $cm^{-1}$ for galactose, and selected from around 569 to 629 $cm^{-1}$, around 772 to 832 $cm^{-1}$, around 1044 to 1106 $cm^{-1}$, around 1237 to 1297 $cm^{-1}$, around 1438 to 1498 $cm^{-1}$, and around 2966 to 2996 $cm^{-1}$ for fructose.

6. A method of measuring albumin by irradiating a sample solution containing albumin with excitation light of a single wavelength, receiving scattered light from said sample solution and separating the same into its spectral components for obtaining light scattering spectra, and quantitatively measuring albumin through peak intensity of a spectrum being shifted from said excitation wavelength to 810 to 840 $cm^{-1}$, or an integral value of a proper range of a spectrum being shifted from an excitation wavelength of 632.8 nm to 256 to 1620 $cm^{-1}$ or from an excitation wavelength of 514.5 nm to 837 to 3060 $cm^{-1}$.

7. A method of measuring γ-globulin by irradiating a sample solution containing γ-globulin with excitation light of a single wavelength, receiving scattered light from said sample solution and separating the same into its spectral components for obtaining light scattering spectra, and quantitatively measuring γ-globulin through peak intensity of a spectrum being shifted from said excitation wavelength to 175 to 195 $cm^{-1}$, 425 to 450 $cm^{-1}$, 640 to 670 $cm^{-1}$, 820 to 845 $cm^{-1}$, 845 to 870 $cm^{-1}$, 1370 to 1400 $cm^{-1}$ 1575 to 1620 $cm^{-1}$, 1850 to 1900 $cm^{-1}$, 2000 to 2200 $cm^{-1}$, 2350 to 2400 $cm^{-1}$ or 2400 to 2460 $cm^{-1}$.

8. A method of measuring hemoglobin by irradiating a sample solution containing hemoglobin with excitation light of a single wavelength, receiving scattered light from said sample solution and separating the same into its spectral components for obtaining light scattering spectra, and quantitatively measuring hemoglobin peak intensity of a spectrum being shifted from said excitation wavelength to 640 to 670 $cm^{-1}$, 820 to 845 $cm^{-1}$, 1370 to 1400 $cm^{-1}$, 1575 to 1620 $cm^{-1}$, 1850 to 1900 $cm^{-1}$, 2000 to 2200 $cm^{-1}$, 2350 to 2400 $cm^{-1}$ or 2400 to 2460 $cm^{-1}$.

* * * * *